(12) United States Patent
Matsunami

(10) Patent No.: US 11,225,258 B2
(45) Date of Patent: Jan. 18, 2022

(54) SAFE DRIVING ASSISTANCE SYSTEM

(71) Applicant: SOSAIKOUSEIKAI CLINICAL FOUNDATION MATSUNAMI RESEARCH PARK, Gifu (JP)

(72) Inventor: Hidetoshi Matsunami, Gifu (JP)

(73) Assignee: SOSAIKOUSEIKAI CLINICAL FOUNDATION MATSUNAMI RESEARCH PARK, Gifu (JP)

( * ) Notice: Subject to any disclaimer, the term of this patent is extended or adjusted under 35 U.S.C. 154(b) by 0 days.

(21) Appl. No.: 17/099,149

(22) Filed: Nov. 16, 2020

(65) Prior Publication Data

US 2021/0197832 A1 Jul. 1, 2021

Related U.S. Application Data

(63) Continuation of application No. PCT/JP2019/019557, filed on May 16, 2019.

(51) Int. Cl.
*B60Q 1/00* (2006.01)
*B60W 40/08* (2012.01)
(Continued)

(52) U.S. Cl.
CPC ......... *B60W 40/08* (2013.01); *A61B 5/02055* (2013.01); *A61B 5/14532* (2013.01);
(Continued)

(58) Field of Classification Search
CPC ...... B60W 40/08; B60W 50/12; B60W 50/14; B60W 2540/221; B60W 2540/26;
(Continued)

(56) References Cited

U.S. PATENT DOCUMENTS

2013/0070043 A1\* 3/2013 Geva .................... B60K 28/066
348/14.02
2016/0363931 A1\* 12/2016 Yang ...................... G07C 5/008
(Continued)

FOREIGN PATENT DOCUMENTS

EP 3482678 A1 5/2019
JP 200256500 A 2/2002
(Continued)

OTHER PUBLICATIONS

International Search Report and Written Opinion for International Application No. PCT/JP2019/019557, filed May 16, 2018, dated Aug. 20, 2019.
(Continued)

*Primary Examiner* — Anh V La
(74) *Attorney, Agent, or Firm* — Fox Rothschild LLP

(57) ABSTRACT

A safe driving assistance system includes a wearable terminal having a terminal identification information, a first and a second sensor acquiring a biometric information of a driver, a safe driving assistance in-vehicle device having a criteria determination unit. The criteria determination unit determines that a blood glucose level is a predetermined number or less and at least one selected the group consisting of that a heart rate is more than a predetermined number, a skin temperature change is more than a predetermined number and an increase in sweat rate is more than a predetermined number, a safe driving assistance in-vehicle device is connected to a vehicle control unit controlling a vehicle driven by the driver, and an operating state of the vehicle is controlled based on a determination result by the criteria determination unit.

13 Claims, 25 Drawing Sheets

(51) Int. Cl.
  *A61B 5/0205* (2006.01)
  *A61B 5/145* (2006.01)
  *A61B 5/00* (2006.01)
  *B60Q 1/46* (2006.01)
  *B60Q 5/00* (2006.01)
  *B60W 50/12* (2012.01)
  *B60W 50/14* (2020.01)

(52) U.S. Cl.
  CPC .............. *A61B 5/4266* (2013.01); *B60Q 1/46* (2013.01); *B60Q 5/005* (2013.01); *B60W 50/12* (2013.01); *B60W 50/14* (2013.01); *B60W 2540/221* (2020.02); *B60W 2540/26* (2013.01)

(58) Field of Classification Search
  CPC ............. B60W 40/09; B60W 2540/22; B60W 2040/0872; B60W 50/16; B60W 2040/0809; B60W 2040/0863; B60W 2050/0095; B60Q 1/46; B60Q 5/005; B60Q 1/52; B60Q 1/50; B60Q 1/525; B60Q 9/008; B60K 28/06; B60K 28/063; G08B 21/00; G08B 25/04; G08G 1/09; G08G 1/16
  USPC ........ 340/439, 438, 435, 436, 426.11, 426.3, 340/573.1
  See application file for complete search history.

(56) References Cited

U.S. PATENT DOCUMENTS

2017/0105104 A1* 4/2017 Ulmansky .............. G08B 21/02
2017/0364070 A1    12/2017 Oba
2018/0043901 A1    2/2018  Kim et al.
2018/0229674 A1*   8/2018  Heinrich ............ G06K 9/00845

FOREIGN PATENT DOCUMENTS

| JP | 2007188 A    | 1/2007 |
| JP | 2008137639 A | 6/2008 |
| JP | 2016018474 A | 2/2016 |
| JP | 2016115356 A | 6/2016 |
| JP | 201826109 A  | 2/2018 |
| JP | 201870029 A  | 5/2018 |
| WO | 2018008666 A1 | 1/2018 |

OTHER PUBLICATIONS

Study Session in Ministry of Land, Infrastructure, Transport and Tourism on Study Session On Utilization Of Biological Data For Driver Abnormality Detection And Automatic Control Technology Through Medical-engineering Collaboration, Nov. 17, 2017.
Study Session in Ministry of Land, Infrastructure, Transport and Tourism on Study Session on Driver-wearable Biological Data Measurement/Transmission Device Utilization Through Medical-engineering Collaboration , Jan. 30, 2018.
The Council Ministry of Land, Infrastructure, Transport and Tourism, on 2018 Accident Countermeasures Council Due to Health in Commercial Vehicles, Feb. 22, 2019.
Office Action dated Jul. 7, 2020 for corresponding JP Appl. No. 2018-094852.
Written Opinion for International Application No. PCT/JP2019/019557, filed May 16, 2018, dated Aug. 20, 2019 (translation).

* cited by examiner (c)

SAFE DRIVING ASSISTANCE SYSTEM

CROSS REFERENCES TO RELATED APPLICATIONS

This application is based upon and claims the benefit of priority from the prior International Application PCT/JP2019/019557, filed on May 16, 2019, and the prior Japanese Patent Application No. 2018-094852, filed on May 16, 2018, No. 2018-094863, filed on May 16, 2018, No. 2018-094864, filed on May 16, 2018, No. 2018-094853, filed on May 16, 2018, and No. 2018-094854, filed on May 16, 2018. The entire contents of these applications are incorporated herein by reference.

FIELD

The present invention relates to a safe driving assistance system for supporting vehicle operation considering the driver's health condition. One embodiment of the present invention relates, in particular, to the safe driving assistance system for supporting the driving of a vehicle by a patient with hypoglycemia, epilepsy, heart disease or dementia, or the driving of a vehicle considering the mental condition of the driver.

BACKGROUND

Recently, under the cooperation of public administration and automobile manufacturers, automobiles equipped with automatic brakes and pedal improper acceleration suppression devices, etc. (safe driving support vehicles) are becoming popular. The safe driving support vehicle was developed as a countermeasure to the increase in the number of fatal accidents caused by elderly drivers over 75 years old, and it was given a function to cope with an erroneous operation, etc. by drivers. Though various attempts to the autonomous cruising of the automobile have been made, the practical application has not been achieved.

On the other hand, in recent years, in addition to fatal accidents caused by elderly drivers, fatal accidents caused by disturbance of consciousness of driver have also become a social problem. Under these circumstances, Section 2 of Article 3 (Dangerous Driving Causing Death or Injury) of the Act on Punishment of Acts Inflicting Death or Injury on Others by Driving a Motor Vehicle, etc., which was enforced on Nov. 27, 2013 stipulates that a person who drives a motor vehicle in a state where the person is likely to hinder safe driving under the influence of a disease specified by Cabinet Order as those which are likely to hinder the safe driving of motor vehicles, thereby comes to have difficulty in driving safely under the influence of the disease, is subject to punishment by imprisonment with work for not more than 12 years when the person thereby causes injury of another; or imprisonment with work for not more than 15 years when the person thereby causes death of another (so-called charges of driving while sick resulting in deaths and injuries).

Article 3 of the Order for Enforcement of the Act on Punishment of Acts Inflicting Death or Injury on Others by Driving a Motor Vehicle, etc., which was enforced on May 20, 2014 stipulates that diseases specified by Cabinet Order influenceable on safe driving are schizophrenia when it presents symptoms which are likely to cause the driver to lack any of the capacities of reasoning, prediction, decision making or operation which are necessary for driving a motor vehicle safely; epilepsy when the recurrence of seizures causing impaired consciousness or impaired mobility of the driver is likely to occur (excluding those in which the recurrence of seizures occurs only during sleep); recurrent syncope (meaning the disease inflicting transient impaired consciousness on a person due to ischemia of the whole brain where the recurrence of seizures is likely to occur); hypoglycemia when it presents symptoms which are likely to cause the driver to lack any of the capacities of reasoning, prediction, decision making or operation which are necessary for driving a motor vehicle safely; manic-depressive disorder (including mania and depression) when it presents symptoms which are likely to cause the driver to lack any of the capacities of reasoning, prediction, decision making or operation which are necessary for driving a motor vehicle safely; and sleep disorder when it presents symptoms of serious drowsiness.

Here, hypoglycemia is a disorder characterized by low blood glucose levels and the presence of sympathetic symptoms and central nervous system manifestations. Sympathetic symptoms are symptoms such as sweating, palpitations, and tremor in a hand. Central nervous system manifestations are symptoms such as dizziness, sleepiness, weakness, loss of concentration, convulsions, and coma which may cause permanent damage to the brain when a treatment is delayed. Since the blood glucose threshold at which sympathetic symptoms appear is higher than the blood glucose threshold at central nervous system manifestations, the patient generally becomes aware of sympathetic symptoms prior to the onset of central nervous system manifestations. However, in elderly patients, patients with autonomic neuropathy, patients with repeated hypoglycemia, and infants, syncope, and coma may occur without sympathetic symptoms, which is called unconscious hypoglycemia. In the case of unconscious hypoglycemia, glycemic control is often difficult, and in the case of inability to artificially regulate glycemia, a driver's license may not be granted or may be withheld. In the meantime, it is possible to suppress the onset, even in the hypoglycemia patient, by intake of the sugar and proper dose of the drug in many cases. Therefore, in the case of hypoglycemic patient who is not unconscious hypoglycemia or a hypoglycemic patient whose blood glucose level can be artificially adjusted, the driver's license of the automobile can be acquired or updated.

Hypoglycemia is particularly frequent in diabetic patients using insulin, a sulfonylurea agent, and fast-acting insulin secretagogues, and the number of diabetic patients tends to increase year by year. It is estimated that there are currently 10 million diabetic patients in Japan as a whole. It is also known that hypoglycemia occurs even with some antiarrhythmic drugs and quinolone antimicrobial, even when they are not antidiabetes agent. Since automobiles are one of the main means of transportation, prohibiting the driving of automobiles in hypoglycemic patients who sufficiently suppresses the onset can be a major obstacle to the self-reliant life of hypoglycemic patients. Therefore, it is desired to develop a safe driving assistance system capable of coping with the sudden onset of hypoglycemia during driving.

Epilepsy is a chronic brain disorder caused by various origins and characterized by recurrent seizures (epileptic seizures) derived from excessive cerebral neuronal discharge. Patients with epilepsy can obtain or renew their driver's license by satisfying certain conditions stipulated by laws and regulations. However, there is no end to fatal and injured accidents caused by epilepsy patients during driving of automobiles.

However, even in patients with epilepsy, in many cases, it is possible to suppress epileptic seizures with the proper use of antiepileptic drugs and surgical treatments. Since it is estimated that there are 600,000 to 1 million epileptic patients in Japan as a whole, and automobiles are one of the main means of transportation, prohibiting the driving of automobiles in epileptic patients with sufficiently suppressed epileptic seizures can be a major obstacle to the self-reliant life of epileptic patients. For this reason, it is desired to develop a safe driving assistance system capable of coping with sudden epileptic seizures during driving.

Arrhythmias can be exemplified as diseases that cause recurrent syncope. Arrhythmias are conditions that indicate abnormal heart rhythmicity and are characterized by extrasystole, tachycardia, and bradycardia. Patients after implantable cardioverter-defibrillator (ICD) implantation and cardiac resynchronization therapy defibrillator (CRT-D) implantation are prohibited from driving in principle at the time of implantation, and in order to permit driving and maintain a driver's license, it is required to submit to the Prefectural Public Safety Commissions a certificate written by a physician who has completed ICD training sponsored by the Japan Heart Rhythm Society or the Japan Heart Failure Society.

However, even in patients with arrhythmias or after implantable cardioverter-defibrillator (ICD) implantation and cardiac resynchronization therapy defibrillator (CRT-D) implantation, extrasystole, tachycardia, and bradycardia can often be controlled with the appropriate use of therapeutic agents or surgical treatment. Since it is estimated that there are more than 1.7 million patients with heart disease in Japan as a whole, and automobiles are one of the main means of transportation, prohibiting the driving of automobiles in patients with sufficiently controlled extrasystole, tachycardia, and bradycardia can be a major obstacle to obstacle to the self-reliant life patients with heart disease. Therefore, it is desired to develop a safe driving assistance system capable of coping with sudden extrasystole, tachycardia, and bradycardia during driving.

Elderly drivers aged 75 years or older are required to undergo cognitive function test at the time of renewal of their driver's license every three years, and when they receive results that indicate that their memory and judgment are low, they need to undergo examinations by medical specialists (temporary aptitude tests) or submit a medical certificate by physicians. When an elderly driver aged 75 years or older is diagnosed as having dementia, he or she is subject to a disposition to suspend or revoke his or her license. On the other hand, when the result of the judgment that the memory ability and judgment ability are slightly lowered is received in cognitive function test, or when it is diagnosed as not being dementia by the diagnosis by the doctor, the driver's license renewal procedure is carried out by taking the training for the elderly.

However, since a cognitive function test is conducted only at the renewal of the driver's license every three years, elderly drivers may develop dementia prior to the renewal of the driver's license. Even patients with dementia do not always have symptoms of dementia, and there is a fluctuation between cognitively normal and cognitively impaired conditions in the day. Therefore, even in the elderly who developed dementia, the driver's license is renewed when the cognitive function is normal at the time of the cognitive function test. For this reason, there is a constant stream of the automobile accidents in which the elderly drivers develop dementia or in the state where the cognitive function is deteriorating. Therefore, a vehicle control system that controls vehicle according to the health status of elderly drivers, particularly cognitive functions, is required.

In recent years, accidents associated with dangerous vehicle driving, such as tailgating, have become a social phenomenon. Article 2 of the Order for Enforcement of the Act on Punishment of Acts Inflicting Death or Injury on Others by Driving a Motor Vehicle, etc. stipulates that an act of, while driving a motor vehicle, cutting in directly in front of another running motor vehicle or otherwise approaching in close proximity to a passing person or vehicle, with the intent to obstruct the passage of another person or vehicle, at a speed that can cause serious danger to traffic is subjected to punishment as dangerous driving causing death or injury.

Therefore, it is desired to develop a safe driving assistance system capable of coping with diseases such as schizophrenia, manic depressive psychosis and sleep disorder, and psychiatric conditions of a driver such as sleepiness, which do not extend to sleep disorder and dangerous driving.

As a vehicle control system for controlling vehicle considering the driver's health condition, for example, in the Japanese Laid-Open Patent Application Publication No. 2016-18474, it is described that a vehicle control system includes a wearable terminal that acquires a driver's biometric information by wearing on the driver's body, an in-vehicle device having a communication unit controls the vehicle mounted of the vehicle, the in-vehicle device includes a permissible information storage unit that stores permissible information for determining whether or not the biometric information is normal, a biometric information reception unit that acquires the biometric information from the wearable terminal, a reference determination unit which determines whether the biological information received by the biometric information reception unit is within an permissible range, using the permission information stored in the permission information storage unit, and a vehicle control unit which slows down and stops the running vehicle in response to the determination that determines the biometric information is out of the permissible range by the reference determination unit.

In addition, Japanese Laid-Open Patent Application Publication No. 2016-18474 discloses that when it is determined that biometric information is out of the permissible range, the warning information is transmitted to a vehicle located in the vicinity of the vehicle of which the driver cannot drive. Furthermore, Japanese Laid-Open Patent Application Publication No. 2016-18474 also describes that the running position of the vehicle is specified from the car navigation system mounted on the vehicle, and the vehicle is stopped by determining whether or not the traveling position of the specified vehicle is capable of slowing and stopping.

Although Japanese Laid-Open Patent Application Publication No. 2016-18474 is a system that slows down and stops running vehicles on the basis of the driver's biometric information or alerts the surrounding vehicle, it is a system that assumes the prevention of drive dozing or the countermeasure at the time of cardiopulmonary arrest. Therefore, it operates when the driver is in an undrivable state, and it is difficult to say that it is a system that is sufficient to support the driving of a car by a patient with hypoglycemia, epilepsy, or cardiac disease, or dementia disability. Although a sensor or the like for acquiring biometric information of the driver has been described in Japanese Laid-Open Patent Application Publication No. 2016-18474, a clear standard for biometric information standard of the driver used for controlling vehicle has not been described, and it is difficult to say that the system is sufficient for supporting safe driving by sufficiently considering the individual differences of the driver's biometric information. Japanese Laid-Open Patent Application Publication No. 2016-18474 does not have a means for specifying a driver and does not have a means for preventing an oblique driving by borrowing a wearable device of another person.

SUMMARY

The present invention solves the above-mentioned problems, and the present invention provides a safe driving assistance system for supporting a vehicle driving while considering a healthy condition or a cognitive function of a driver. In one embodiment, a safe driving assistance system is provided for supporting driving of a vehicle by a hypoglycemic patient, an epilepsy patient, a heart disease patient, or a dementia patient, or driving of a vehicle responsive to a psychiatric condition of a driver. In one embodiment, a safe driving assistance system is provided that identifies a driver and prevents him or her from driving the vehicle illegally.

According to an embodiment of the present invention, a safe driving support system comprises a wearable device including a terminal identification information; a first sensor and a second sensor capable of acquiring a biometric information of a driver; and a safe driving assistance in-vehicle device including a criteria determination unit comparing at least one of permissible information for the driver with a first biometric information received from the first sensor and a second sensor to determine whether the driver is ready to drive, wherein the permissible information are that a blood glucose level is a predetermined number or more and at least one selected a group consisting of that a heart rate is less than a predetermined number, a skin temperature change is less than a predetermined number, and an increase in sweat rate is less than a predetermined number, the first sensor includes at least one selected a group consisting of a pulse meter, a thermometer and a diaphoremeter and the second sensor includes an interstitial fluid glucose concentration meter, the first biometric information includes the blood glucose level and one or more selected from a group consisting of the heart rate, the skin temperature change and a sweat rate change, the criteria determination unit determines whether a blood glucose level measured by the interstitial fluid glucose concentration meter is a predetermined number or more and at least one selected a group consisting of whether a heart rate measured by the pulse meter is less than a predetermined number, a skin temperature change measured by the thermometer is less than a predetermined number, and an increase in sweat rate measured by the diaphoremeter is less than a predetermined number, the safe driving assistance in-vehicle device is connected to a vehicle control unit controlling a vehicle driven by the driver, and the operating state of the vehicle is controlled based on a determination result of the criteria determination unit.

The safe driving assistance in-vehicle device alerts the driver to sugar supplementation when the criteria determination unit determines that the blood glucose level is less than the predetermined number measured by the interstitial fluid glucose concentration meter and at least one selected a group consisting of that the heart rate measured by the pulse meter is the predetermined number or more, the skin temperature change measured by the thermometer is the predetermined number or more, and the increase in sweat rate measured by the diaphoremeter is the predetermined number or more.

The safe driving assistance in-vehicle device alerts the driver to stop when the criteria determination unit determines that the blood glucose level measured by the interstitial fluid glucose concentration meter is less than the predetermined number and at least one selected a group consisting of that the heart rate measured by the pulse meter is the predetermined number or more, the skin temperature change measured by the thermometer is the predetermined number or more, and the increase in sweat rate measured by the diaphoremeter is the predetermined number or more.

The permissible information is blood glucose level of 50 mg/dL or more, the safe driving assistance in-vehicle device may transmit a stop signal to the vehicle control unit when the criteria determination unit determines that the blood glucose level measured by the interstitial fluid glucose concentration meter is less than 50 mg/dL, and the vehicle control unit stops the vehicle.

The safe driving assistance in-vehicle device further includes an output unit having a display unit and an audio output unit, wherein the display unit indicates a display prompting the driver to supplement sugar or stop the vehicle, and the audio output unit outputs a voice prompting the driver to supplement sugar or stop the vehicle to alert the driver to stop.

The safe driving assistance system further includes a location information receiver capable of communicating with in-vehicle devices; and the server arranged outside a vehicle and capable of communicating with the safe driving assistance in-vehicle device, wherein the safe driving assistance in-vehicle device transmits an information of the driver, a location information of the vehicle received by the location information receiver, and a signal notifying the server of abnormality of the driver when the criteria determination unit determines that the blood glucose level measured by the interstitial fluid glucose concentration meter is less than the predetermined number and at least one selected a group consisting of that the heart rate measured by the pulse meter is the predetermined number or more, the skin temperature change measured by the thermometer is the predetermined number or more, and the increase in sweat rate measured by the diaphoremeter is the predetermined number or more.

The safe driving assistance system further includes a location information receiver capable of communicating with in-vehicle devices, wherein the vehicle control unit slows down the vehicle and adjusts an inter-vehicle distance from the leading vehicle according to an operating conditions received from the safe driving assistance in-vehicle device when the criteria determination unit determines that the blood glucose level measured by the interstitial fluid glucose concentration meter is less than the predetermined number and at least one selected a group consisting of that the heart rate measured by the pulse meter is the predetermined number or more, the skin temperature change measured by the thermometer is the predetermined number or more, and the increase in sweat rate measured by the diaphoremeter is the predetermined number or more, the location information receiver acquires a location information of the vehicle and searches for a location information at which the vehicle can stop, the display unit indicates the location information at which the vehicle can stop when acquiring the location information at which the vehicle can stop, the audio output unit outputs a voice for guiding the vehicle to the driver.

The safe driving assistance in-vehicle device further includes an output unit having a display unit and an audio output unit, wherein the audio output unit outputs a voice notifying that the vehicle is urgently stopped to the outside of the vehicle, and the vehicle control unit blinks the hazard lamp of the vehicle.

The safe driving assistance system further includes a location information receiver capable of communicating with in-vehicle devices; and the server arranged outside a vehicle and capable of communicating with the safe driving assistance in-vehicle device, wherein the safe driving assistance in-vehicle device transmits an information of the driver, the location information of the vehicle received by the location information receiver, and a rescue signal to the server when the criteria determination unit determines that a blood glucose level measured by the interstitial fluid glucose concentration meter is less than 50 mg/dL.

The vehicle control unit slows down the vehicle and adjusts an inter-vehicle distance from the leading vehicle according to an operating conditions received from the safe driving assistance in-vehicle device when the criteria determination unit determines that the blood glucose level measured by the interstitial fluid glucose concentration meter is less than 50 mg/dL, the location information receiver acquires a location information of the vehicle and searches for a location information at which the vehicle can stop, and the vehicle control unit stops the vehicle based on the position information at which the vehicle can be stopped when acquiring the location information at which the vehicle can stop.

The safe driving assistance system further includes a third sensor capable of acquiring a third biometric information of the driver; and a certification unit included in the safe driving assistance in-vehicle device and certificating the driver, wherein the certification unit carries out a first certification process certificates the driver based on the terminal identification information of the wearable device, and a second certification process certificates the driver by comparing a second biometric information included in a certification information of the driver with the third biometric information received from the third sensor.

The safe driving assistance in-vehicle device may transmit a signal permitting an engine to start to the vehicle control unit when the criteria determination unit determines that the blood glucose level is more than the predetermined number measured by the interstitial fluid glucose concentration meter, and the vehicle control unit starts the engine in response to an engine starting operation by the driver.

The safe driving assistance in-vehicle device may not transmit a signal permitting an engine to start to the vehicle control unit when the criteria determination unit determines that the blood glucose level is less than the predetermined number measured by the interstitial fluid glucose concentration meter and at least one selected a group consisting of that the heart rate measured by the pulse meter is the predetermined number or more, the skin temperature change measured by the thermometer is the predetermined number or more, and the increase in sweat rate measured by the diaphorometer is the predetermined number or more.

According to an embodiment of the present invention, a safe driving assistance system comprises a wearable terminal including a terminal identification information and a first sensor capable of acquiring a biometric information of a driver, a second sensor capable of acquiring a biometric information of the driver, and a safe driving assistance in-vehicle device including a criteria determination unit comparing at least one permissible information for the driver with the first biometric information received from the first sensor and/or the second sensor to determine whether the driver is ready to drive, wherein the permissible information is that a brain wave pattern specific to epileptic seizures, which are one selected from a group consisting of a sharp wave, a spike, a polyspikes, a spike-and-slow-wave complex, a polyspike-and-slow-wave complex, and a fourteen and six Hz positive spikes, etc. and a heart rate less than a predetermined number are not detected, the first sensor includes a pulse meter, the second sensor includes a brain wave measurement unit, the first biometric information is a heart rate and the brain wave, the criteria determination unit determines whether the heart rate measured by the pulse meter is equal to or higher than a predetermined number, and/or whether a brain wave pattern specific to epileptic seizures, which are one selected from the group consisting of the sharp wave, the spike, the polyspikes, the spike-and-slow-wave complex, the polyspike-and-slow-wave complex, and the fourteen and six Hz positive spikes, etc. is detected or not in the brain wave measured by the brain wave measurement unit, the safe driving assistance in-vehicle device is connected to a vehicle control unit controlling a vehicle driven by the driver, the operation state of the vehicle is controlled based on the determination result of the criteria determination unit.

The safe driving assistance in-vehicle device may alert the driver when the criteria determination unit determines that the heart rate measured by the pulse meter is equal to or more than a predetermined number.

The safe driving assistance in-vehicle device may transmit a stop signal to the vehicle control unit, and the vehicle control unit may stop the vehicle when the criteria determination unit determines that a brain wave pattern specific to epileptic seizures, which are one selected from a group consisting of a sharp wave, a spike, polyspikes, a spike-and-slow-wave complex, a polyspike-and-slow-wave complex and a fourteen and six Hz positive spikes is detected in the brain wave measured by the brain wave measurement unit.

The safe driving assistance in-vehicle device further includes an output unit having a display unit and an audio output unit, wherein the display unit may indicate a display prompting the driver to stop, and the audio output unit may output a voice prompting the driver to stop the vehicle to alert the driver to stop.

The safe driving assistance system further includes a location information receiver capable of communicating with the safe driving assistance in-vehicle device and a server arranged outside the vehicle capable of communicating of the safe driving assistance in-vehicle device, wherein the safe driving assistance in-vehicle device may transmit an information of the driver, a location information of the vehicle received by the location information receiver, and a signal notifying the server of abnormality of the driver when the criteria determination unit determines that the heart rate measured by the pulse meter is the predetermined number or more.

The safe driving assistance system further includes a location information receiver capable of communicating with the safe driving assistance in-vehicle device, wherein the vehicle control unit may slow down the vehicle and adjust an inter-vehicle distance from the leading vehicle according to an operating condition received from the safe driving assistance in-vehicle device when the criteria determination unit determines that the heart rate measured by the pulse meter is more than a predetermined number, the location information receiver may acquire a location information of the vehicle and search for a location information at which the vehicle can stop, the display unit may indicate the location information at which the vehicle can stop, the audio output unit may output a voice for guiding the vehicle to the driver.

The safe driving assistance in-vehicle device further includes an output unit having a display unit and an audio output unit, wherein the audio output unit may output a voice notifying that the vehicle is urgently stopped to the outside of the vehicle, the vehicle control unit may blink the hazard lamp of the vehicle.

The safe driving assistance system further includes a location information receiver capable of communicating with the safe driving assistance in-vehicle device, and a server arranged outside the vehicle and capable of communicating with the safe driving assistance in-vehicle device, wherein the safe driving assistance in-vehicle device may transmit an information of the driver, a location information of the vehicle received by the location information receiver, and a rescue signal to the server when the criteria determination unit determines that a brain wave pattern specific to epileptic seizures, which are one selected from a group consisting of a sharp wave, spike, a polyspikes, a spike-and-slow-wave complex, a polyspike-and-slow-wave complex, and a fourteen and six Hz positive spikes, etc. is detected in the brain wave measured by the brain wave measurement unit.

When the criteria determination unit determines that a brain wave measured by the brain wave measurement unit is detected a brain wave pattern specific to epileptic seizures, which are one selected from a group consisting of a sharp wave, a spike, a polyspikes, a spike-and-slow-wave complex, a polyspike-and-slow-wave complex, and a fourteen and six Hz positive spikes, etc., the vehicle control unit may slow down the vehicle and adjust an inter-vehicle distance from the leading vehicle according to an operating condition received from the safe driving assistance in-vehicle device, the location information receiver may acquire a location information of the vehicle and searches for a location information at which the vehicle can stop, the vehicle control unit may stop the vehicle based on a location information at which the vehicle can stop when acquiring the location information at which the vehicle can stop.

The safe driving assistance system further includes third sensor capable of acquiring a third biometric information of the driver and a certification unit included in the safe driving assistance in-vehicle device and certificating the driver, wherein the certification unit may carry out a first certification process to certificate the driver based on the terminal identification information of the wearable device, and a second certification process to certificate the driver by comparing a second biometric information included in a certification information of the driver with the third biometric information received from the third sensor.

The safe driving assistance in-vehicle device may transmit a signal permitting an engine to start to the vehicle control unit, when the criteria determination unit determines that the heart rate measured by the pulse meter is less than a predetermined number, the vehicle control unit may start the engine in response to an engine starting operation by the driver.

The safe driving assistance in-vehicle device may not transmit a signal permitting an engine to start to the vehicle control unit when the criteria determination unit determines that the heart rate measured by the pulse meter is the predetermined number or more, or when the criteria determination unit determines that a brain wave pattern specific to epileptic seizures, which are one selected from a group consisting of a sharp wave, a spike, a polyspikes, a spike-and-slow-wave complex, a polyspike-and-slow-wave complex, and a fourteen and six Hz positive spikes, etc. is detected in the brain wave measured by the brain wave measurement unit.

According to an embodiment of the present invention, a safe driving assistance system comprises a wearable terminal including a terminal identification information and a first sensor capable of acquiring a biometric information of a driver, a second sensor capable of acquiring a biometric information of the driver, and a safe driving assistance in-vehicle device including a criteria determination unit comparing at least one permissible information for the driver with the first biometric information received from the first sensor and/or the second sensor to determine whether the driver is ready to drive, wherein the permissible information is that the heart rate is in a predetermined range and the electrocardiographic complex is not classified as ventricular tachycardia or ventricular fibrillation, the first sensor includes a pulse meter, the second sensor includes an electrocardiograph, the first biometric information includes a heart rate and an electrocardiographic complex, and the criteria determination unit determines that the heart rate measured by the pulse meter is in a first range and/or the electrocardiographic complex acquired by the electrocardiograph is not classified as ventricular tachycardia or ventricular fibrillation, the safe driving assistance in-vehicle device is connected to a vehicle control unit controlling a vehicle driven by the driver, the operation state of the vehicle is controlled based on the determination result of the criteria determination unit.

The safe driving assistance in-vehicle device may alert the driver when the criteria determination unit determines that the heart rate measured by the pulse meter is outside the first range.

The safe driving assistance in-vehicle device may transmit a signal to the vehicle control unit to stop and the vehicle control unit may stop the vehicle when the criteria determination unit determines that the heart rate measured by the pulse meter is in a second range, or the criteria determination unit determines that an electrocardiographic complex acquired by the electrocardiograph is classified as ventricular tachycardia or ventricular fibrillation.

The safe driving assistance in-vehicle device further includes an output unit having a display unit and an audio output unit, wherein the display unit may indicate a display prompting the driver to stop, and the audio output unit may output a voice prompting the driver to stop the vehicle to alert the driver to stop.

The safe driving assistance system further includes a location information receiver capable of communicating with the safe driving assistance in-vehicle device and a server arranged outside a vehicle capable of communicating of the safe driving assistance in-vehicle device, wherein the safe driving assistance in-vehicle device may transmit an information of the driver, a location information of the vehicle received by the location information receiver, and a signal notifying the server of abnormality of the driver when the criteria determination unit determines that the heart rate measured by the pulse meter is outside the first range.

The safe driving assistance system further includes a location information receiver capable of communicating with the safe driving assistance in-vehicle device, the vehicle control unit may slow down the vehicle and adjust an inter-vehicle distance from the leading vehicle according to an operating condition received from the safe driving assistance in-vehicle device when the criteria determination unit determines that the heart rate measured by the pulse meter is outside the first range, the location information receiver may acquire a location information of the vehicle and search for a location information at which the vehicle can stop, the display unit may indicate the location information at which the vehicle can stop, the audio output unit may output a voice for guiding the vehicle to the driver.

The safe driving assistance in-vehicle device further includes an output unit having a display unit and an audio output unit, wherein the audio output unit may output a voice notifying that the vehicle is urgently stopped to the outside of the vehicle, the vehicle control unit may blink the hazard lamp of the vehicle.

The safe driving assistance system further includes a location information receiver capable of communicating with the safe driving assistance in-vehicle device, and a server arranged outside the vehicle and capable of communicating with the safe driving assistance in-vehicle device, wherein the safe driving assistance in-vehicle device may transmit an information of the driver, a location information of the vehicle received by the location information receiver, and a rescue signal to the server when the criteria determination unit determines that a heart rate measured by the pulse meter is outside a second range, or the criteria determination unit determines that an electrocardiographic complex acquired by the electrocardiograph is classified as ventricular tachycardia or ventricular fibrillation.

When the criteria determination unit determines that a heart rate measured by the pulse meter is outside the second range, or the criteria determination unit determines that an electrocardiographic complex acquired by the electrocardiograph is classified as ventricular tachycardia or ventricular fibrillation, the vehicle control unit may slow down the vehicle and adjust an inter-vehicle distance from the leading vehicle according to an operating condition received from the safe driving assistance in-vehicle device, the location information receiver may acquire a location information of the vehicle and searches for a location information at which the vehicle can stop, the vehicle control unit may stop the vehicle based on the location information at which the vehicle can stop when acquiring the location information at which the vehicle can stop.

The safe driving assistance system further includes a third sensor capable of acquiring a third biometric information of the driver and a certification unit included in the safe driving assistance in-vehicle device and certificating the driver, wherein the certification unit may carry out a first certification process to certificate the driver based on the terminal identification information of the wearable device, and a second certification process to certificate the driver by comparing a second biometric information included in a certification information of the driver with the third biometric information received from the third sensor.

The safe driving assistance in-vehicle device may transmit a signal permitting an engine to start to the vehicle control unit when the criteria determination unit determines that the heart rate measured by the pulse meter is in the first range, and/or the criteria determination unit determines that an electrocardiographic complex acquired by the electrocardiograph is not classified as ventricular tachycardia or ventricular fibrillation, the vehicle control unit may start the engine in response to an engine starting operation by the driver.

The safe driving assistance in-vehicle device may not transmit a signal permitting an engine to start to the vehicle control unit when the criteria determination unit determines that the heart rate measured by the pulse meter is outside the first range, or when the criteria determination unit determines that an electrocardiographic complex acquired by the electrocardiograph is classified as ventricular tachycardia or ventricular fibrillation.

According to an embodiment of the present invention, a safe driving assistance system includes a wearable terminal including a terminal identification information and a safe driving assistance in-vehicle device including a criteria determination unit presenting a question to the driver, calculating a percentage of correct answers from the answers entered by the driver, and comparing a permissible information for the driver with the percentage of correct answers to determine whether the driver is ready to drive, wherein the permissible information is a predetermined percentage of correct answers, the criteria determination unit determines that whether the percentage of correct answers entered by the driver is greater than or equal to the predetermined percentage of correct answers, the safe driving assistance in-vehicle device is connected to a vehicle control unit controlling a vehicle driven by the driver, the operation state of the vehicle is controlled based on the determination result of the criteria determination unit.

The safe driving assistance in-vehicle device may alert the driver when the criteria determination unit determines that the percentage of correct answers entered by the driver is less than the predetermined percentage of correct answers.

The safe driving assistance in-vehicle device may transmit a signal to the vehicle control unit to stop and the vehicle control unit may stop the vehicle when the criteria determination unit determines that the percentage of correct answers entered by the driver is less than the predetermined percentage of correct answers which is the danger value.

The safe driving assistance system further includes a pressure sensor disposed on a handle of the vehicle, wherein the criteria determination unit receives a signal from the pressure sensor and when it determines that the driver does not grasp the handle, the safe driving assistance in-vehicle device may transmit a stop signal to the vehicle control unit, and the vehicle control unit may stop the vehicle.

The safe driving assistance in-vehicle device further includes an output unit including a display unit and an audio output unit, and an input unit, wherein the criteria determination unit may present questions to the driver via the display unit and/or the audio output unit and may input a response of the driver via the input unit.

The display unit may indicate a display prompting the driver to stop the vehicle, and the audio output unit may output a voice prompting the driver to stop the vehicle to alert the driver to stop.

The safe driving assistance system further includes a location information receiver capable of communicating with the safe driving assistance in-vehicle device and a server arranged outside a vehicle capable of communicating of the safe driving assistance in-vehicle device, wherein the safe driving assistance in-vehicle device may transmit an information of the driver, a location information of the vehicle received by the location information receiver, and a signal notifying the server of abnormality of the driver when the criteria determination unit determines that the percentage of correct answers entered by the driver is less than the predetermined percentage of correct answers.

The safe driving assistance system further includes a location information receiver capable of communicating with the safe driving assistance in-vehicle device, when the criteria determination unit determines that the percentage of correct answers entered by the driver is less than the predetermined percentage of correct answers, the vehicle control unit may slow down the vehicle and adjust an inter-vehicle distance from the leading vehicle according to an operating condition received from the safe driving assistance in-vehicle device, the location information receiver may acquire a location information of the vehicle and search for a location information at which the vehicle can stop, the display unit may indicates the location information at which the vehicle can stop, the audio output unit may output a voice for guiding the vehicle to the driver.

The safe driving assistance in-vehicle device further includes an output unit having a display unit and an audio output unit, wherein the audio output unit may output a voice notifying that the vehicle is urgently stopped to the outside of the vehicle, the vehicle control unit may blink the hazard lamp of the vehicle.

The safe driving assistance system further includes a location information receiver capable of communicating with the safe driving assistance in-vehicle device, and a server arranged outside the vehicle and capable of communicating with the safe driving assistance in-vehicle device, wherein the safe driving assistance in-vehicle device may transmit an information of the driver, a location information of the vehicle received by the location information receiver, and a rescue signal to the server when the criteria determination unit determines that the percentage of correct answers entered by the driver is less than the predetermined percentage of correct answers which is the danger value, or the criteria determination unit determines that the driver does not grasp the handle.

When the criteria determination unit determines that the percentage of correct answers entered by the driver is less than the predetermined percentage of correct answers which is the danger value, or the criteria determination unit determines that the driver does not grasp the handle, the vehicle control unit may slow down the vehicle and adjust an inter-vehicle distance from the leading vehicle according to an operating condition received from the safe driving assistance in-vehicle device, the location information receiver may acquire a location information of the vehicle and searches for a location information at which the vehicle can stop, the vehicle control unit may stop the vehicle based on a location information at which the vehicle can stop when acquiring the location information at which the vehicle can stop.

The safe driving assistance system further includes a sensor capable of acquiring a biometric information of the driver and a certification unit included in the safe driving assistance in-vehicle device and certificating the driver, wherein the certification unit may carry out a first certification process to certificate the driver based on the driver's identification information stored in a storage unit of the wearable device, and a second certification process to certificate the driver by comparing a first biometric information included in a certification information of the driver with the second biometric information received from the sensor.

The safe driving assistance in-vehicle device may transmit a signal permitting an engine to start to the vehicle control unit when the criteria determination unit determines that the percentage of correct answers entered by the driver is the predetermined percentage or more of correct answers, the vehicle control unit may start the engine in response to an engine starting operation by the driver.

The safe driving assistance in-vehicle device may not transmit a signal permitting an engine to start to the vehicle control unit when the criteria determination unit determines that the percentage of correct answers entered by the driver is less than the predetermined percentage of correct answers, or the criteria determination unit determines that the driver does not grasp the handle.

The permissible information for the driver may be entered from a terminal for healthcare professionals, arranged outside the vehicle, and stored in a server capable of communicating with the safe driving assistance in-vehicle device, or in a region accessible only from the terminal for healthcare professionals of a storage unit of the wearable device.

According to an embodiment of the present invention, a safe driving assistance system comprises a wearable terminal including a terminal identification information, a sensor capable of acquiring a biometric information of a driver, and a safe driving assistance in-vehicle device having a criteria determination unit comparing at least one permissible information for the driver preset by an specialist with a first biometric information received from the sensor to determine whether the driver is ready to drive, wherein the safe driving assistance in-vehicle device is connected to a vehicle control unit controlling a vehicle driven by the driver, the operation state of the vehicle is controlled based on the determination result of the criteria determination unit.

The permissible information for the driver may be entered from a terminal for healthcare professionals, arranged outside the vehicle, and stored in a server capable of communicating with the safe driving assistance in-vehicle device, or in a region accessible only from the terminal for healthcare professionals of a storage unit of the wearable device.

The sensor may include a first sensor disposed in the wearable device and a second sensor capable of communication with the safe driving assistance in-vehicle device, and the criteria determination unit may compare the permissible information for the driver with the first biometric information received from the first sensor and/or the second sensor to determine whether the driver is ready to drive.

The safe driving assistance in-vehicle device further includes an output unit having a display unit and an audio output unit, wherein the first sensor includes a thermometer or a pulse meter, the second sensor includes a brain wave measurement unit or a face identification sensor, when the criteria determination unit detects any abnormal value, which at least one selected a group consisting of a skin temperature measured by the thermometer being more than a predetermined number, a pulse rate measured by the pulse meter being less than a predetermined number, and a θ wave included in a brain wave measured by the brain wave measurement unit or percentage of eye opening of the driver measured by the face identification sensor being less than a predetermined number, the display unit may indicate a display prompting the driver to stop, and the audio output unit may output a voice prompting the driver to stop the vehicle to alert the driver to stop.

The safe driving assistance system further includes a pressure sensor disposed on a handle of the vehicle and a vibrator provided in the driver's seat of the vehicle, when the criteria determination unit detects any danger value, which at least one selected a group consisting of a δ wave included in the brain wave, the closed state of the driver's eye or a state in which the pressure sensor does not detect the pressure of the driver's hand, the safe driving assistance in-vehicle device may alert the driver by driving the vibrator.

The safe driving assistance in-vehicle device further includes an output unit having a display unit and an audio output unit, wherein the first sensor includes a thermometer, a diaphoremeter, or a pulse meter, the second sensor includes a brain wave measurement unit or a face identification sensor, when the criteria determination unit detects any abnormal value, which at least one selected a group consisting of a skin temperature measured by the thermometer being more than a predetermined number, a sweat rate measured by the diaphoremeter is increased, a pulse rate measured by the pulse meter being more than a predetermined number, a continuous β wave included in a brain wave measured by the brain wave measurement unit or percentage of movement of the driver's face measured by the face identification sensor being more than a predetermined number, the display unit may indicate a display prompting the driver to stop, and the audio output unit may output a voice alerting the driver.

The safe driving assistance system further includes a pressure sensor disposed on a handle of the vehicle and a vibrator provided in the driver's seat of the vehicle, when the criteria determination unit detects any abnormal value, which at least one selected a group consisting of a skin temperature measured by the thermometer being more than a predetermined number, a sweat rate measured by the diaphoremeter is increased, a pulse rate measured by the pulse meter being more than a predetermined number, a continuous β wave included in a brain wave measured by the brain wave measurement unit, percentage of movement of the driver's face measured by the face identification sensor being more than a predetermined number, or a state in which the pressure sensor does not detect the pressure of the driver's hands, the display unit may indicate a display prompting the driver to stop, and the audio output unit may output a voice alerting the driver.

The safe driving assistance in-vehicle device may transmit a stop signal to the vehicle control unit and the vehicle control unit may stop the vehicle.

The safe driving assistance system includes a location information receiver capable of communicating with the safe driving assistance in-vehicle device, when the criteria determination unit detects the abnormal value, the safe driving assistance in-vehicle device may transmit an information of the driver, a location information of the vehicle received by the location information receiver, and a signal notifying the server of abnormality of the driver.

The safe driving assistance system further includes a location information receiver capable of communicating with the safe driving assistance in-vehicle device, when the criteria determination unit detects the abnormal value, the vehicle control unit may slow down the vehicle and adjust an inter-vehicle distance from the leading vehicle according to an operating condition received from the safe driving assistance in-vehicle device, the location information receiver may acquire a location information of the vehicle and search for a location information at which the vehicle can stop, the display unit may indicate the location information at which the vehicle can stop, the audio output unit may output a voice for guiding the vehicle to the driver.

When the criteria determination unit detects the abnormal value or the danger value, the safe driving assistance in-vehicle device may transmit a stop signal to the vehicle control unit, and the vehicle control unit may stop the vehicle.

The safe driving assistance in-vehicle device further includes an output unit having a display unit and an audio output unit, wherein the audio output unit may output a voice notifying that the vehicle is urgently stopped to the outside of the vehicle, the vehicle control unit may blink the hazard lamp of the vehicle.

The safe driving assistance system includes a location information receiver capable of communicating with the safe driving assistance in-vehicle device, when the criteria determination unit detects the danger value, the safe driving assistance in-vehicle device may transmit the driver's information, a location information received by the location information receiver, and a rescue signal to the servers.

When the criteria determination unit detects the abnormal value or the danger value, the vehicle control unit may slow down the vehicle and adjust an inter-vehicle distance from the leading vehicle according to an operating condition received from the safe driving assistance in-vehicle device, the location information receiver may acquire a location information of the vehicle and search for a location information at which the vehicle can stop, the vehicle control unit may stop the vehicle based on a location information at which the vehicle can stop when acquiring the location information at which the vehicle can stop.

The safe driving assistance system further includes a third sensor capable of acquiring a biometric information of the driver and a certification unit included in the safe driving assistance in-vehicle device and certificating the driver, wherein the certification unit may carry out a first certification process to certificate the driver based on the terminal identification information of the wearable device, and a second certification process to certificate the driver by comparing the second biometric information included in a certification information of the driver with the third biometric information received from the third sensor.

When the criteria determination unit detects any abnormal value, which at least one selected a group consisting of a skin temperature measured by the thermometer being more than a predetermined number, a pulse rate measured by the pulse meter being less than a predetermined number, and a θ wave included in a brain wave measured by the brain wave measurement unit or percentage of eye opening of the driver measured by the face identification sensor being less than a predetermined number, the safe driving assistance in-vehicle device may not transmit a signal permitting an engine to start to the vehicle control unit.

When the criteria determination unit detects any abnormal value, which at least one selected a group consisting of a skin temperature measured by the thermometer being more than a predetermined number, a sweat rate measured by the diaphoremeter being increased, a pulse rate measured by the pulse meter being more than a predetermined number, a continuous β wave included in a brain wave measured by the brain wave measurement unit or percentage of movement of the driver's face measured by the face identification sensor being more than a predetermined number, the safe driving assistance in-vehicle device may not transmit a signal permitting an engine to start to the vehicle control unit.

BRIEF DESCRIPTION OF DRAWINGS

FIG. 20A is a schematic diagram of a handle part electrocardiograph 41a;

Figure 1:
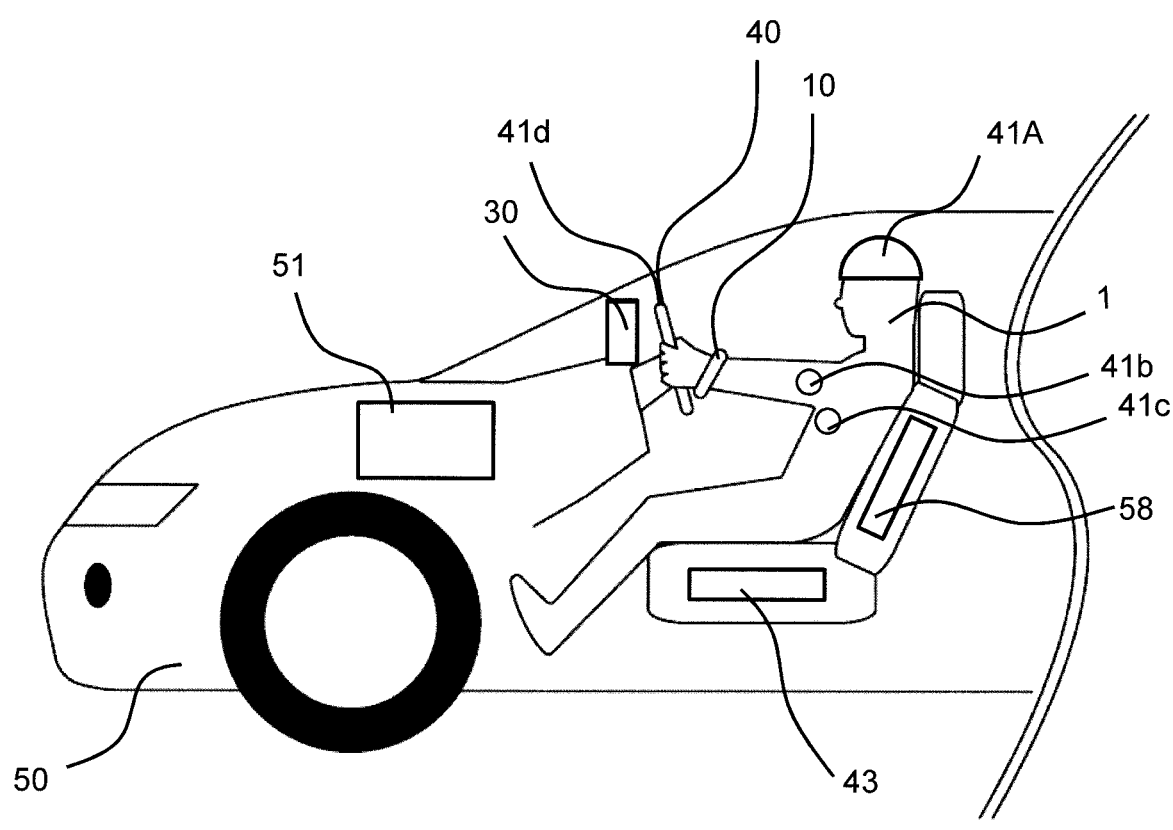
FIG. 1 is a schematic diagram illustrating a safe driving assistance system 100 according to an embodiment of the present invention.

DESCRIPTION OF THE REFERENCE NUMERAL 1 driver, 3 passenger, 10 wearable device, 10A wearable device, 11 storage unit, 12a first electrode, 12b second electrode, 13 sensor, 13a pulse meter, 13b thermometer, 13c diaphoremeter, 15 control unit, 16 communication unit, 17 power supply, 18 input unit, 19 adhesive layer, 20 dedicated transceiver, 25 control unit, 26 communication unit, 27 power supply, 29 SIM card, 30 safe driving assistance in-vehicle device, 31 control unit, 31a certification unit, 31b criteria determination unit, 32 storage unit, 32a permissible information storage unit, 33 output unit, 33a display unit, 33b audio output unit, 34 communication unit, 35 input unit, 41 measurement unit, 41a handle part electrocardiograph, 41b interstitial fluid glucose concentration measurement part, 41c pacemaker, 41d handle part pressure sensor, 42 pressure sensor, 43 sensor, 43a sensor, 44 sensor element, 44a electrode, 44b electrode, 44c electrode, 44d electrode, 45 control unit, 46 storage unit, 47 communication unit, 48 power supply, 50 vehicle, 51 vehicle control unit, 52 unified standard conversion unit, 53 power supply, 55 location information receiver, 58 vibrator, 60 leading vehicle, 100 safe driving support system, 100a safe driving support system, 100b safe driving support system, 101 server, 110 medical institution, 111 terminal for healthcare professionals, 130 administrative organ, 131 terminal for administrative organ, 133 ambulance, 140 company, 141 terminal for company, 143 assistance vehicle, 150 transportation facilities, 151 terminal for transportation institution, 200 bus, 250 taxi

DESCRIPTION OF THE EMBODIMENTS

With reference to the drawings, a safe driving assistance system according to the present invention will be described below. The safe driving assistance system according to the present invention is not construed as being limited to the description of the following embodiments. In the drawings referred in embodiments, the same portions or portions having similar functions are denoted by the same reference numerals, and a repetitive description thereof is omitted.

Figure 2:
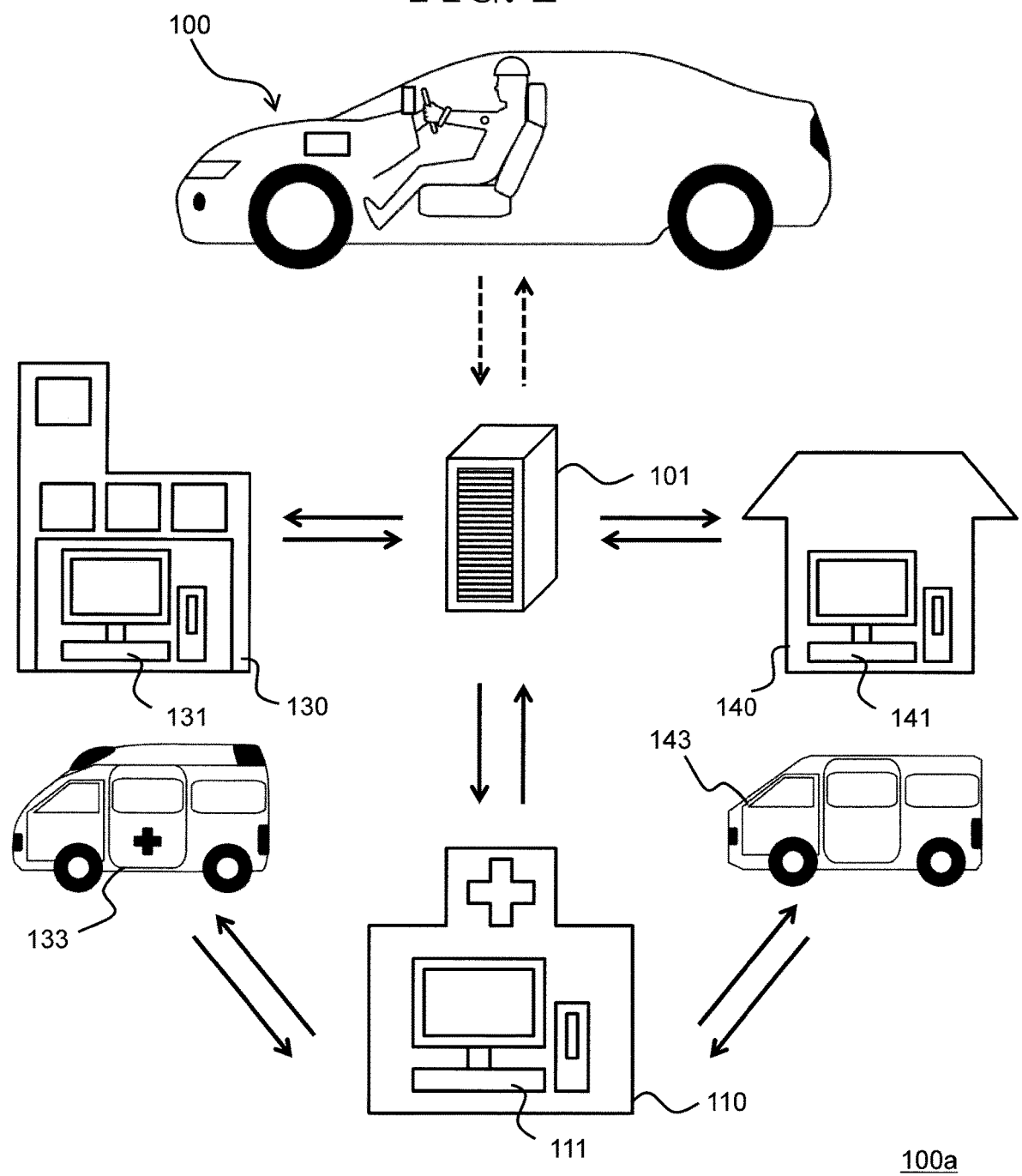
FIG. 2 is a schematic diagram illustrating a safe driving assistance system 100a according to an embodiment of the present invention.

FIG. 1 is a schematic diagram illustrating a safe driving assistance system 100 according to an embodiment of the present invention. The safe driving assistance system 100 includes, for example, a wearable device 10 and a safe driving assistance in-vehicle device 30. FIG. 2 is a schematic diagram illustrating a safe driving assistance system 100a according to an embodiment of the present invention. The safe driving assistance system 100a is an extended safe driving assistance system of the safe driving assistance system 100, and includes, for example, a vehicle 50 having the safe driving assistance system 100, a server 101, a medical institution 110, an administrative organ 130, and a company 140, but not limited thereto. The server 101 is, for example, a server capable of connecting to the safe driving assistance system 100 via wireless communication, and is connected to the medical institution 110, the administrative organ 130, and/or the company 140 via wired communication or wireless communication. That is, the server 101 is a server that functions as a hub for connecting safely the driving assistance system 100 to the medical institution 110, the administrative organ 130, and/or the company 140 in the safe driving assistance system 100*a*. The hardware of the server 101 is not particularly limited and is composed of a known server and various electronic devices included in the known server.

In the following, the safe driving assistance system according to the present invention will be described in detail with reference to a safe driving assistance system for supporting the driving of a motor vehicle by hypoglycemic patients. In one embodiment, the server 101 may store the information of the driver 1 in association with a terminal identification information of the wearable device 10. The information of the driver 1 is the name, address, medical history, and the like of the driver 1, and may be any information specifying the driver 1. The information of the driver 1 preferably includes, for example, a code indicating that the driver 1 is authorized to drive a vehicle. It may include information specifying a sensor for monitoring the driver 1 due to a disease of the driver 1 or the like. In one embodiment, the server 101 may store the permissible information for the driver 1.

The permissible information of the driver 1 is a reference based on a biometric information for permitting the driver 1 to drive a vehicle. Since the permissible information is also a criterion for restricting the driving by the driver 1, an appropriate criterion for each type of a biometric information and a type of the biometric information is set by a healthcare professional according to the illness or the like possessed by the driver 1. In one embodiment, when the driver 1 is a hypoglycemic patient, for example, the permissible information based on a value indicating the presence or absence of sympathetic symptoms and a blood glucose value can be used.

The values indicating the presence or absence of sympathetic symptoms may be, for example, heart rate, skin temperature change, sweat rate change, or the like. The amount of change of each value may be an amount of change per unit of time. For example, when the heart rate exceeds a predetermined number as a sympathetic symptom due to hypoglycemia, the risk of subsequent central nervous system manifestation is increased. Therefore, the permissible information may be that the heart rate is less than a predetermined number. Similarly, when the skin temperature changes become more than a predetermined number as a sympathetic symptom due to hypoglycemia, the risk of subsequent central nervous system manifestation is increased. For this reason, it may be the permissible information that the skin temperature change is less than a predetermined number. In addition, when sweating (cold or sweat) in certain areas is observed as the sympathetic symptoms due to hypoglycemia, the risk of subsequent central nervous system manifestation is increased. Therefore, it may be the permissible information that an increase in the amount of sweat rate is less than a predetermined number. Because differences in the type of sympathetic symptoms and value indicating presence or absence of sympathetic symptoms vary from individuals, the type of sympathetic symptoms and value indicating presence of sympathetic symptoms are set by the healthcare professionals. The permissible information based on the value indicating the presence or absence of sympathetic symptoms may be used more than one. By having a plurality of values indicating the presence or absence of sympathetic symptoms as the permissible information, the accuracy of detecting sympathetic symptoms of the driver 1 is improved.

In one embodiment, a storage region storing the information of the driver 1 in the server 101 and a storage region storing the permissible information of the driver 1 are preferably in a region accessible only to a specialist such as healthcare professionals. A terminal 111 for healthcare professionals can rewrite the information of the driver 1 and the permissible information by connecting to the server 101. Therefore, in the present embodiment, the information of the driver 1 and the permissible information can be rewritten only by a person who can operate the terminal 111 for healthcare professionals, i.e., a specialist such as a healthcare professional.

The vehicle 50 includes a wireless communication unit mounted on the vehicle and the safe driving assistance system 100 is capable of communicating with the server 101 via wireless communication. As wireless communication, for example, a mobile communication network can be used. In one embodiment, the safe driving assistance system 100 may be connected to the server 101 via a line of a mobile phone, a smartphone, or a tablet-type terminal such as iPad (registered trademark) or a dedicated transceiver owned by the driver 1. Alternatively, the vehicle 50 may be equipped with a dedicated wireless communication device connectable to mobile communication networks.

The medical institution 110 includes at least a so-called family doctor of the driver 1. The medical institution 110 includes various hospitals and doctors' offices. The medical institution 110 includes a terminal 111 for the healthcare professionals and the terminal for the healthcare professionals 111 is connected to the server 101 via wired communication or wireless communication. Accordingly, the terminal 111 for healthcare professionals can be connected to the safe driving assistance system 100 via the server 101. The terminal 111 for healthcare professionals may be a general-purpose computer terminal or a dedicated terminal. For example, a personal computer, a tablet-type terminal such as an iPad (registered trademark), or a terminal capable of receiving mail such as a smartphone can be used as the terminal 111 for healthcare professionals. In one embodiment, the terminal 111 for healthcare professionals may be connected to the safe driving assistance system 100 via the mobile communication networks described above, rather than via the server 101. The terminal 111 for healthcare professionals may receive the biometric information of the driver 1 from the safe driving assistance system 100 and allow the healthcare professional to monitor the biometric information of the driver 1. When an abnormality is detected in the biometric information of the driver 1, the safe driving assistance system 100 may notify the terminal 111 for healthcare professionals of the abnormality. In one embodiment, when the terminal 111 for healthcare professionals is notified of an abnormal in the biometric information of the driver 1 from the safe driving assistance system 100, it is preferable that the healthcare professional confirms the biometric information of the driver 1 and requests the administrative organ 130 or the company 140 to assist the driver 1 or rescue the driver 1.

In one embodiment, the terminal 111 for healthcare professionals may be installed in a plurality of the medical institution 110. The priority order of the terminal 111 for healthcare professionals for notifying the abnormality of the biometric information of the driver 1 (the priority order of the medical institution 110 for notifying the abnormality of the biometric information of the driver 1) from the safe driving assistance system 100 is registered in the server 101, and when the abnormality is detected in the biometric information of the driver 1, the server 101 may notify the abnormality of the biometric information of the driver 1 to the terminal 111 for healthcare professionals in accordance with the registered priority order. The server 101 may notify the first terminal 111 for healthcare professionals (e.g., family doctor) of an abnormality in the biometric information of the driver 1, and in the absence of a response from the first terminal 111 for healthcare professionals, notify the second terminal 111 for healthcare professionals (e.g., local core hospital) of an abnormality in the biometric information of the driver 1. In one embodiment, when there is no response from the first terminal 111 for healthcare professionals, an abnormality of the biometric information of the driver 1 may be informed to a terminal capable of receiving a message such as a tablet-type terminal, a smartphone, or the like of a family of the driver 1. In the safe driving assistance system 100a, the terminal 111 for healthcare professionals may store and execute an application capable of displaying the biometric information or the like of the driver 1 acquired from the safe driving assistance system 100 in the main memory device, or may display the biometric information of the driver 1 provided from the server 101 via the Internet browser.

In one embodiment, the biometric information of the driver 1 acquired from the safe driving assistance system 100 may be stored in the server 101. An specialist such as a healthcare professional can browse the biometric information of the driver 1 stored and accumulated in the server 101 via the terminal 111 for healthcare professionals. The health care professional can appropriately adjust the permissible information based on a medical examination result of the driver 1 and the accumulated the biometric information of the driver 1 during periodic medical examinations of the driver 1. For this reason, the specialist such as the healthcare professional may periodically update the permissible information by storing the permissible information adjusted via the terminal 111 for healthcare professionals in the server 101. Since the blood glucose levels occurring the sympathetic symptoms and central nervous system manifestation vary among individuals and are affected by the patient's physical condition, it is preferable that the permissible information is periodically adjusted by the health care professional.

The administrative organ 130 includes, for example, but is not limited to, a fire station (including a metropolitan fire department) and a police station (including a metropolitan police department). The administrative organ 130 includes a terminal 131 for administrative organ, and the terminal 131 for administrative organ is connected to the server 101 via wired communication or wireless communication. Therefore, the terminal 131 for administrative organ can be connected to the safe driving assistance system 100 and the terminal 111 for healthcare professionals via the server 101. The terminal 131 for administrative organ may be a general-purpose computer terminal or may be a dedicated terminal. For example, a personal computer, a tablet-type terminal such as an iPad (registered trademark), or a terminal capable of receiving mail such as a smartphone can be used as the terminal 131 for administrative organ. In one embodiment, when the terminal 111 for healthcare professionals is notified by the safe driving assistance system 100 of an abnormal biometric information of the driver 1, it is preferable that the healthcare professional confirms the biometric information of the driver 1 and requests the administrative organ 130 to assist the driver 1 or rescue the driver 1. In the safe driving assistance system 100a, since the terminal 111 for healthcare professionals is connected to the terminal 131 for administrative organ via the server 101, the healthcare professional can request the administrative organ 130 to support the driver 1 and rescue the driver 1 by operating the terminal 111 for healthcare professionals.

In an embodiment, the terminal 131 for administrative organ may be connected to the safe driving assistance system 100 via the above-described mobile communication networks without using the server 101. The terminal 131 for administrative organ may receive the biometric information of the driver 1 from the safe driving assistance system 100 and allow an operator of the administrative organ 130 to monitor the biometric information of the driver 1. When the abnormality is detected in the biometric information of the driver 1, the safe driving assistance system 100 may notify the terminal 131 for administrative organ of the abnormality.

The operator of the administrative organ 130 can acquire a location information of the vehicle 50 from the safe driving assistance system 100 and dispatch an ambulance 133 and a patrol car (not shown) to a stop location of the vehicle 50 when the operator receives a request from the medical institution 110 or when the abnormal biometric information of the driver 1 is notified to the terminal 131 for administrative organ. The terminal 131 for administrative organ may be a general-purpose computer terminal or may be a dedicated terminal. In the safe driving assistance system 100a, the terminal 131 for administrative organ may store and execute an application capable of displaying the biometric information or the like of the driver 1 acquired from the safe driving assistance system 100 in the main memory device, or may display the biometric information of the driver 1 provided from the server 101 via the Internet browser.

The company 140 includes, for example, nursing care facilities, home care stations, private security companies, and the like. The company 140 includes a terminal 141 for the company and is connected to the server 101 via wired or wireless communication. Therefore, the terminal 141 for company can be connected to the safe driving assistance system 100 and the terminal 111 for healthcare professionals via the server 101. The terminal 141 for company may be a general-purpose computer terminal or may be a dedicated terminal. For example, a personal computer, a tablet-type terminal such as an iPad (registered trademark), or a terminal capable of receiving mail such as a smartphone can be used as the terminal 141 for company. In one embodiment, when the terminal 111 for healthcare professionals is notified by the safe driving assistance system 100 of an abnormal biometric information of the driver 1, it is preferable that the healthcare professional confirms the biometric information of the driver 1 and requests the company 140 to assist the driver 1 or rescue the driver 1. In safe driving assistance system 100a, since the terminal 111 for healthcare professionals is connected to the terminal 141 for company via the server 101, the healthcare professional can request the company 140 to support the driver 1 and rescue the driver 1 by operating the terminal 111 for healthcare professionals.

In one embodiment, the terminal 141 for company may be connected to the safe driving assistance system 100 via the above-described mobile communication networks without using the server 101. The terminal 141 for company may receive the biometric information of the driver 1 from the safe driving assistance system 100 and allow the operator of the company 140 to monitor the biometric information of the driver 1. When an abnormality is detected in the biometric information of the driver 1, the safe driving assistance system 100 may notify the terminal 141 for company of the abnormality.

When the operator of the company 140 receives a request from the medical institution 110 or when the abnormal state of the biometric information the driver 1 is notified to the terminal 141 for company, the operator can acquire a location information of the vehicle 50 from the safe driving assistance system 100 and dispatch a support vehicle 143 (e.g., vehicle loaded with a nursing care worker or a security worker) to a stop location of the vehicle 50. The terminal 141 for company may be a general-purpose computer terminal or may be a dedicated terminal. In the safe driving assistance system 100*a*, the terminal 141 for company may store and execute an application capable of displaying the biometric information or the like of the driver 1 acquired from the safe driving assistance system 100 in the main memory device, or may display the biometric information of the driver 1 provided from the server 101 via the Internet browser. In safe driving assistance system 100*a*, since the medical institution 110 and the company 140 can share the biometric information of the driver 1, the operator of the company 140, the nursing care personnel, and the security personnel can provide appropriate support and treatment to the driver 1 in cooperation with the medical professional or under the guidance of the medical professional.

In one embodiment, when the driver 1 is a user of the company 140 which is a nursing facility, the server 101 may notify the abnormality of the driver 1 to the terminal 141 for company when the terminal 111 for healthcare professionals does not respond or the operation requesting assistance or rescue of the driver 1 to the terminal 131 for administrative organ or the terminal 141 for company is not performed after notifying the abnormality of the driver 1 from the safe driving assistance system 100 to the terminal 111 for healthcare professionals. In this instance, the operator of the company 140 can confirm the status of the driver 1 via the terminal 141 for company, and can provide appropriate support and treatment to the driver 1 in cooperation with the healthcare professional or under the guidance of the healthcare professional. The operator of the company 140 may confirm the status of the driver 1 via the terminal 141 for company, and may request the terminal 131 for administrative organ to assist or rescue the driver 1. The server 101 may notify the terminal 131 for administrative organ of an abnormality of the driver 1 when the terminal 141 for company does not respond. In this manner, the order in which the abnormality of the driver 1 is notified from the server 101 may be defined.

Figure 3:
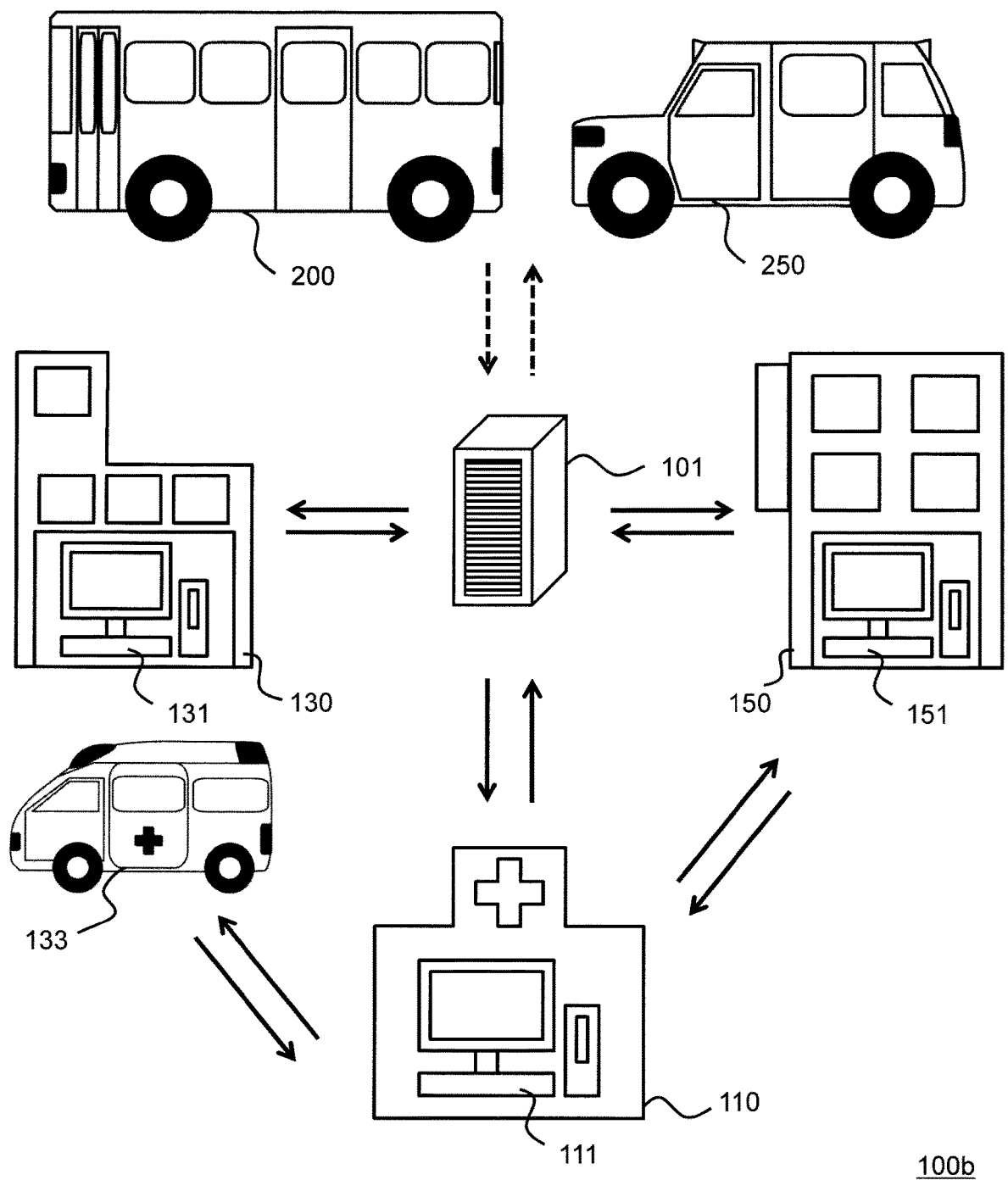
FIG. 3 is a schematic diagram illustrating a safe driving assistance system 100b according to an embodiment of the present invention.

The safe driving assistance system according to the present invention is not limited to a safe driving support for personal drivers. FIG. 3 is a schematic diagram illustrating a safe driving assistance system 100*b* according to an embodiment of the present invention. The safe driving assistance system 100*b* is a safe driving assistance system in which the safe driving assistance system 100 is extended for a driver engaged in transportation facilities, and includes, for example, but not limited to, a bus 200, a taxi 250, the server 101, the medical institution 110, the administrative organ 130, and a transportation facilities 150 provided with the safe driving assistance system 100. The server 101 is, for example, a server connectable to the safe driving assistance system 100 via wireless communication, and is connected to the medical institution 110, the administrative organ 130, and the transportation facilities 150 via wired communication or wireless communication. Other configurations are the same as those described above, and therefore a detailed description is omitted.

The transportation facilities 150 include, for example, a bus operating company and a taxi company. The transportation facilities 150 include a terminal 151 for transportation facilities and are connected to the server 101 via wired or wireless communication. Therefore, the terminal 151 for transportation facilities can be connected to the safe driving assistance system 100 and the terminal 111 for healthcare professionals via the server 101. The terminal 151 for transportation facilities may be a general-purpose computer terminal or a dedicated terminal. For example, as the terminal 151 for transportation facilities, a personal computer, a tablet-type terminal such as an iPad (registered trademark), or a terminal capable of receiving mail such as a smartphone can be used. In one embodiment, when the terminal 111 for healthcare professionals is notified by the safe driving assistance system 100 of an abnormal biometric information of the driver 1, it is preferable that the healthcare professional confirms the biometric information of the driver 1 and requests the transportation facilities 150 to assist the driver 1 or rescue the driver 1. In one embodiment, when the safe driving assistance system 100 notifies the terminal 151 for transportation facilities of an abnormal biometric information of the driver 1, the operator of the transportation facilities 150 may ask the healthcare professional for guidance in order to provide appropriate support and treatment to the driver 1.

In one embodiment, the terminal 151 for transportation facilities may be connected to the safe driving assistance system 100 via the above-described mobile communication networks without using the server 101. The terminal 151 for transportation facilities may receive the biometric information of the driver 1 from the safe driving assistance system 100 and allow the operator of the transportation facilities 150 to monitor the biometric information of the driver 1. When an abnormality is detected in the biometric information of the driver 1, the safe driving assistance system 100 may notify the terminal 151 for transportation facilities of the abnormality.

When the operator of the transportation facilities 150 receives a request from the medical institution 110 or when the abnormal state of the biometric information of the driver 1 is notified to the terminal 151 for transportation facilities, the operator can acquire a location information of the bus 200 or the taxi 250 from the safe driving assistance system 100 and request the administrative organ 130 to assist or rescue the driver 1. The operator of the transportation facilities 150 may also dispatch an alternative driver or vehicle based on the location information of the vehicle 50. Since it is assumed that passengers are on board the bus 200 or the taxi 250 owned by the transportation facilities 150, in addition to rescuing the driver 1, it is required to secure the safety of passengers and alternative transportation means. The safe driving assistance system 100*b* also contributes to the support of the transportation function of the transportation facilities 150.

The terminal 151 for transportation facilities may be a general-purpose computer terminal or a dedicated terminal. In the safe driving assistance system 100*b*, the terminal 151 for transportation facilities may store and execute an application capable of displaying the biometric information or the like of the driver 1 acquired from the safe driving assistance system 100 in the main memory device, or may display the biometric information of the driver 1 provided from the server 101 via the Internet browser.

In one embodiment, after notifying the abnormality of the driver 1 from the safe driving assistance system 100 to the terminal 111 for healthcare professionals, the server 101 may notify the abnormality of the driver 1 to the terminal 151 for transportation facilities when the terminal 111 for healthcare professionals does not respond or when the terminal 111 for healthcare professionals does not perform operations for requesting support or rescue of the driver 1 to the terminal 131 for administrative organ or the terminal 151 for transportation facilities. In this instance, the operator of the transportation facilities 150 can confirm the status of the driver 1 via the terminal 151 for transportation facilities, and can provide appropriate support and measures to the driver 1 in cooperation with the healthcare professional or under the guidance of the healthcare professional. The operator of the transportation facilities 150 may confirm the status of the driver 1 via the terminal 151 for transportation facilities and request the terminal 131 for administrative organ to assist or rescue the driver 1. When the terminal 151 for transportation facilities does not respond, the server 101 may notify the terminal 131 for administrative organ of the abnormality of the driver 1. In this manner, the order in which the abnormality of the driver 1 is notified from the server 101 may be defined.

<Wearable Terminal>

Figure 4A:
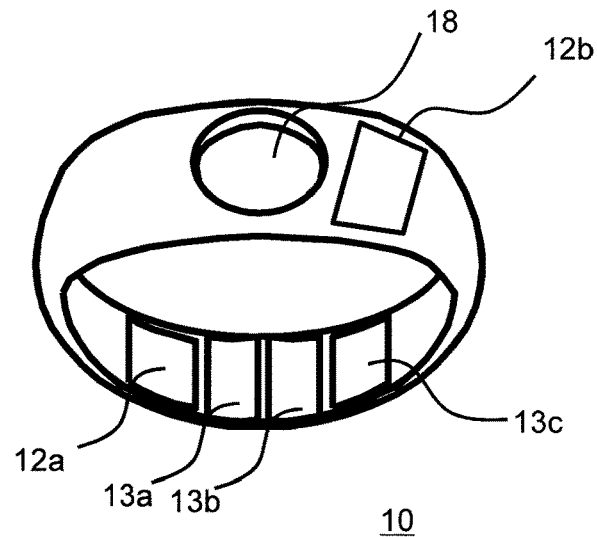
FIG. 4A is a schematic diagram illustrating a wearable device 10 according to an embodiment of the present invention, and is a schematic diagram illustrating the wearable device 10.
Figure 4B:
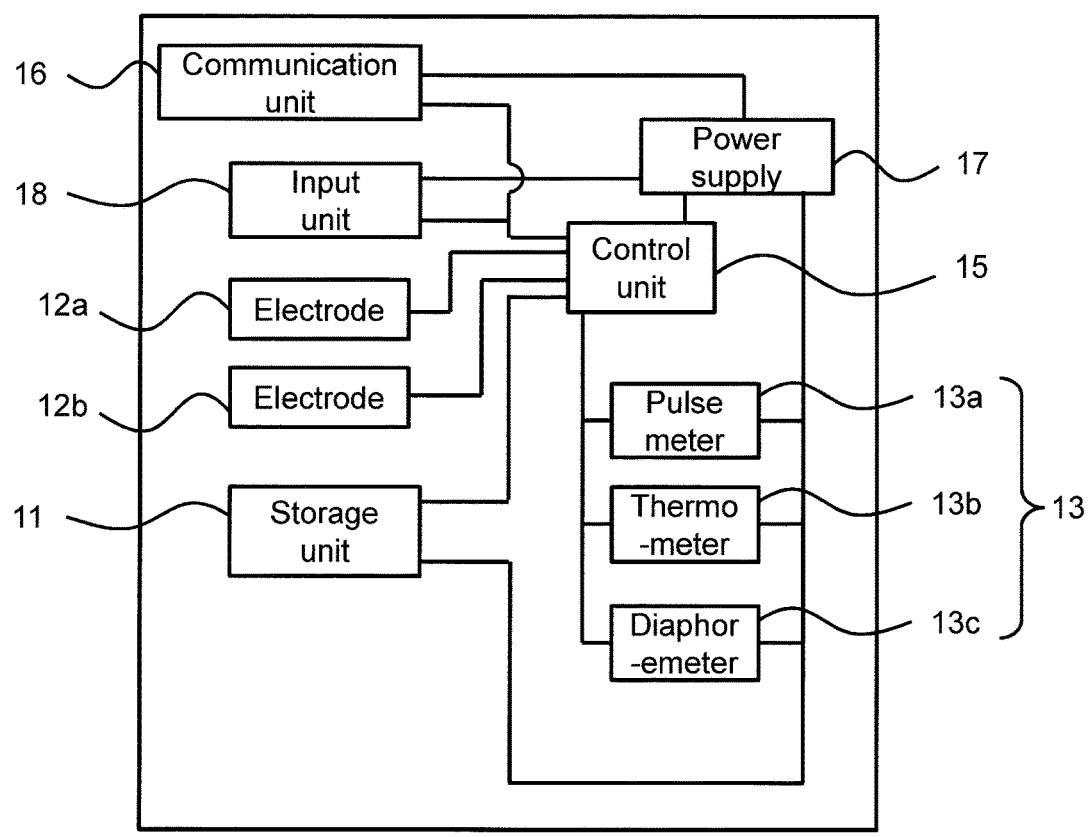
FIG. 4B is a block diagram illustrating the wearable device 10.

FIG. 4 is a schematic diagram illustrating a wearable device 10 according to an embodiment of the present invention. The wearable device 10 is a device wearable by the driver 1, and may be, for example, a watch-type device as shown in FIG. 4A. FIG. 4B is a block diagram illustrating the wearable device 10 according to an embodiment of the present invention. The wearable device 10 includes, but is not limited to, a storage unit 11, a sensor 13, a control unit 15, a communication unit 16, a power supply 17, and an input unit 18. The storage unit 11 may be, for example, a memory, and be temporarily store the biometric information acquired from the driver 1 measured by the sensor 13. In one embodiment, a permissible information storage unit may be provided which is a region for storing the permissible information of the driver 1. The storage unit 11 may include a certification information storage unit which is a region to store a certification information of the driver 1.

The wearable device 10 has a terminal identification information. The terminal identification information may be, for example, a physical address (MAC address) assigned to the communication unit 16. In the present embodiment, since the driver 1 and the terminal identification information are associated with each other, the driver 1 can be specified based on the terminal identification information.

In one embodiment, the sensor 13 (first sensor) is a device for obtaining the biometric information from the driver 1 and includes, for example, at least one of a pulse meter, a thermometer, or a diaphoremeter. Here, the pulse rate measured by the pulse meter is treated as substantially synonymous with the heart rate, and the body temperature measured by the thermometer is treated as substantially synonymous with the skin temperature. In the present embodiment, the sensor 13 is integrally formed with the wearable device 10, but the sensor 13 may be formed separately from the wearable device 10. For example, when cold sweat, which is local sweating, is detected, the diaphoremeter may detect the amount of sweating in the palm as a configuration integral with a handle 40. As the sensor 13, it is more preferable to select a sensor having a large difference between the biometric information of the driver 1 in the normal state and the permissible information of the driver 1, which will be described later. Thus, at least one of the pulse rate, the skin temperature change, and the sweat rate change measured by the sensor 13 can be compared with the permissible information of the driver 1 to determine whether the driver 1 is ready to operate the vehicle 50. The sensor 13 may further include other sensors capable of measuring the biometric information indicating the presence or absence of sympathetic symptoms of the driver 1 other than the above.

The sensor 13 may be a combination of a plurality of sensors indicating the presence or absence of sympathetic symptoms. By combining a plurality of sensors indicating the presence or absence of sympathetic symptoms, the accuracy of detecting sympathetic symptoms of the driver 1 is improved. Number, shapes, and arrangements of the sensors 13 included in the wearable device 10 can be arbitrarily selected and are not particularly limited. The wearable device 10 may be configured not to include the sensor 13 when using a pulse meter or the like equivalent to the sensor 13 as the sensor 43 disposed other than the wearable device 10 to be described later.

In one embodiment, the control unit 15 is a device for controlling the wearable device 10, e.g., a central processing unit. The control unit 15 includes programs for controlling the wearable device 10. The program controlling the wearable device 10 is stored in the storage unit 11 and executed in the control unit 15. In one embodiment, the control unit 15 may include an operating system (OS) which controls the wearable device 10 and application programs or modules which function on the safe driving assistance system 100.

In one embodiment, the communication unit 16 is a device in which the wearable device 10 communicates with an external device, and includes, but is not limited to, a communication means conforming to a wireless communication standard such as, for example, Wi-Fi (registered trademark) (a communication means using IEEE 802.11 standards) or Bluetooth (registered trademark). The communication unit 16 is assigned a physical address (MAC address) and can identify the wearable device 10 from the physical address. Since the physical address of the wearable device 10 is associated with the driver 1, the driver 1 can be specified based on the physical address of the wearable device 10. In one embodiment, the wearable device 10 connects to the safe driving assistance in-vehicle device 30 via wireless communications by the communication unit 16. As will be described later, the wearable device 10 can also be connected to the terminal 111 for the healthcare professionals via wireless communication by the communication unit 16.

In one embodiment, the power supply 17 is a common battery and is a repeatedly chargeable and dischargeable power supply that supplies a power to the devices disposed in the wearable device 10. For example, the power supply 17 may be provided with a connecting terminal and supplied with power externally to charge. The power supply 17 may be externally power supplied and charged without contact by wireless power transmission. The power supply 17 is preferably lightweight and large in volume, but is not particularly limited.

The input unit 18 is an input means by which the driver 1 can operate the wearable device 10, and may be, for example, switches, selection buttons, a touch panel, or the like. In one embodiment, the input unit 18 may be a display device (e.g., a liquid crystal display or an organic electroluminescence display) with a touch panel. The shape and position of the input unit 18 can be arbitrarily selected, and are not particularly limited. The input unit 18 may transmit a doctor call by, for example, pressing the button when the driver 1 feels a malfunction. When the input unit 18 is provided with a display device, the biometric information of the driver 1 measured by the sensor 13 may be displayed on the display device and provided to the driver 1.

In one embodiment, the certification information of the driver 1 is a name, an identification code (ID), or the like of the driver 1, and may be information specifying the driver 1. Preferably, the driver's 1 certification information includes, for example, codes indicating that the driver 1 is authorized to drive a vehicle. It may include information specifying a sensor for monitoring the driver 1 due to a disease or the like of the driver 1.

In this embodiment, a measurement part 41b (interstitial fluid glucose concentration measurement part 41b (second sensor)) connected to the safe driving assistance in-vehicle device 30 to be described later is used for detecting blood glucose level. Here, the interstitial fluid glucose concentration measured by the interstitial fluid glucose concentration measurement part 41b is treated as almost synonymous with the blood glucose level. When a predetermined number of blood glucose levels are detected, here less than 70 mg/dL, the risk of subsequent central nervous system manifestation is increased. Therefore, the permissible information may be that the blood glucose level is 70 mg/dL or more. A blood glucose level less than 50 mg/dL indicates that hypoglycemia has already occurred and there is a very high-risk of unconsciousness state in the absence of sympathetic symptoms. Therefore, the permissible information may be that the blood glucose level is 50 mg/dL or more. Blood glucose levels at which hypoglycemia may occur vary among patients. To this end, in one embodiment, the permissible information based on the rate of blood sugar fluctuation, i.e., a rate of drop in blood glucose may be used. A sharp drop in blood glucose level increases the risk of hypoglycemia, even when absolute level is high. A plurality of permissible information based on the blood glucose level may be used. An accuracy of detecting the hypoglycemic symptoms of the driver 1 is improved by having a plurality of criteria in the blood glucose levels as the permissible information.

In one embodiment, the storage unit 11 may store the information of the driver 1 described above as the certification information of the driver 1. The certification information of the driver 1 may include information identifying the driver 1, such as an identification code (ID) of the driver 1, weight, fingerprint information, face information. In one embodiment, the storage unit 11 may store the permissible information of the driver 1. By storing the certification information and the permissible information of the driver 1 in the storage unit 11 of the wearable device 10, the burden of accessing the server 101 can be reduced. Even when the communication between the wearable device 10 and the server 101 is temporarily interrupted due to a communication failure or the like, operation of the safe driving assistance system 100 can be maintained.

In one embodiment, the storage unit 11 of the wearable device 10 may include a certification information storage unit for storing the certification information of the driver 1 and a permissible information storage unit for storing the permissible information of the driver 1. It is preferable that the certification information storage unit storing the certification information of the driver 1 and the permissible information storage unit storing the permissible information of the driver 1 can be rewritten only by a specialist such as a healthcare professional. The wearable device 10 can rewrite the certification information of the driver 1 stored in the certification information storage unit and the permissible information of the driver 1 stored in the permissible information storage unit by connecting to the terminal 111 for healthcare professionals. Therefore, in the present embodiment, the certification information and the permissible information of the driver 1 can be rewritten only by a person who can operate the terminal 111 for healthcare professionals, i.e., the specialist such as a healthcare professional. The wearable device 10 and the terminal 111 for healthcare professionals may be connected to each other by connecting the communication unit 16 and the terminal 111 for healthcare professionals of the wearable device 10 via a connector, or may be connected to each other via communication means conforming to a wireless communication standard provided in the communication unit 16, as described above.

The wearable device 10 may have a certification code, for example, a bar code on the surface of the storage unit 10 instead of the certification information storage unit and the permissible information storage unit. When the safe driving assistance in-vehicle device 30 is equipped with a camera capable of reading the certification code (e.g., an imaging device such as a CCD or a CMOS), a certification code may be captured by the camera, the safe driving assistance in-vehicle device 30 recognizes the captured certification code, and receives the permissible information or the like of the driver 1 corresponding to the certification code from the server 101. The certification code may be a one-dimensional bar code or a two-dimensional bar code such as a QR code (registered trademark).

The wearable device 10 is not limited to the above configuration. For example, the wearable device 10 may further include a vibration function and an audio output unit. When the biometric information of the driver 1 measured by the sensor 13 does not satisfy the permissible information of the driver 1, the wearable device 10 may alert or warn the driver 1 by the vibration function or the audio output unit.

Figure 5:
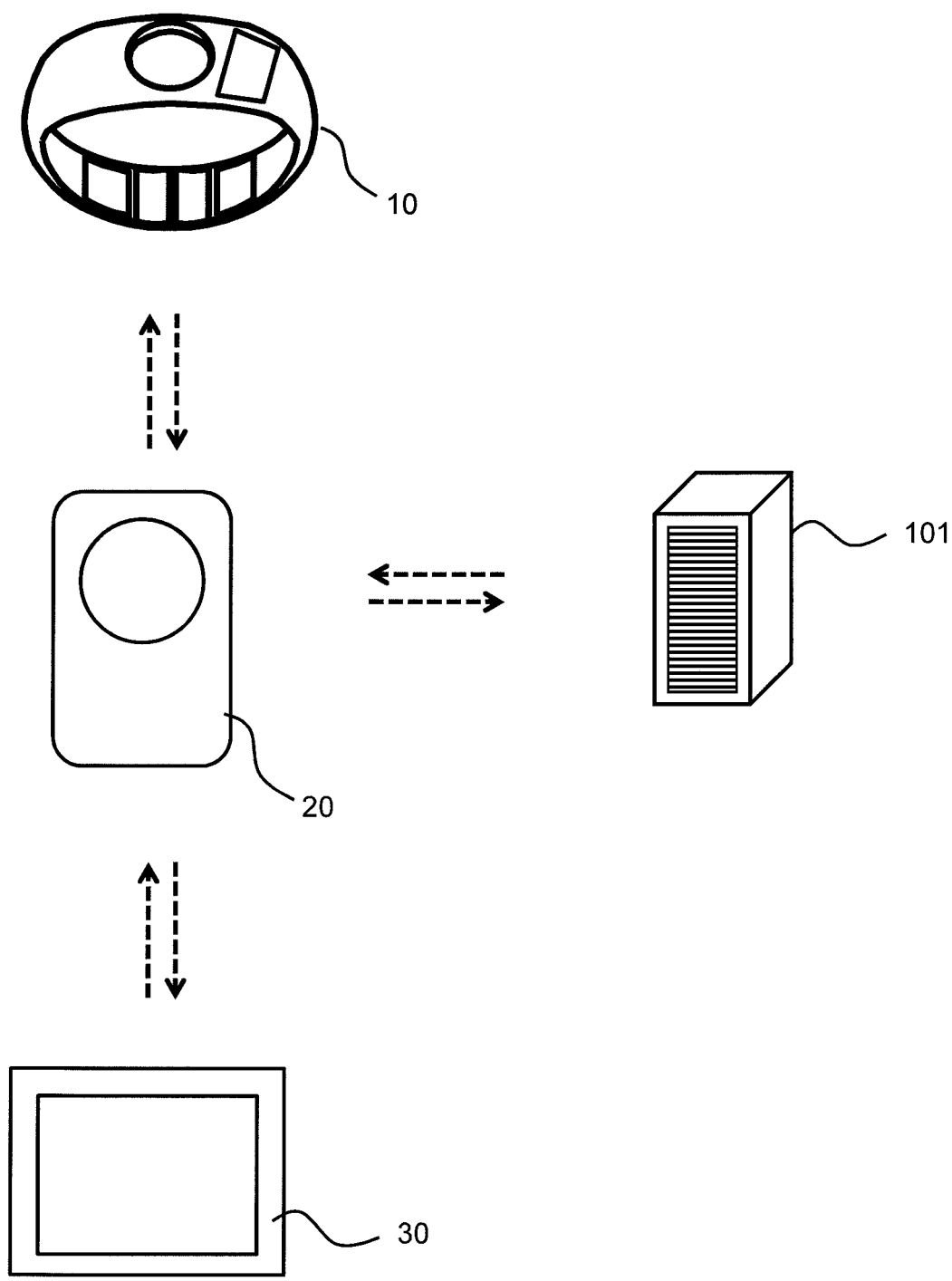
FIG. 5 is a schematic diagram illustrating a communication method of the wearable device 10 according to one embodiment of the present invention.

The wearable device 10 and the server 101 may be connected via a line of a dedicated transceiver 20. FIG. 5 is a schematic diagram illustrating a communication method of the wearable device 10 according to an embodiment of the present invention. The wearable device 10 and the dedicated transceiver 20 are connected by communication means conforming to the wireless communication standard such as Wi-Fi and Bluetooth (registered trademark). Similarly, the safe driving assistance system 100 and the server 101 may be connected via the line of the dedicated transceiver 20. In one embodiment, the wearable device 10 and the safe driving assistance system 100 may be connected via the dedicated transceiver 20. The wearable device 10 and the server 101 can be connected to each other by using terminals that can be used as mobile communication systems such as a tablet-type terminal and a smartphone. A smartphone other than a smartphone used by the driver 1 for a telephone call or the like may be dedicated to the wearable device 10 and used instead of the dedicated transceiver 20.

Figure 6A:
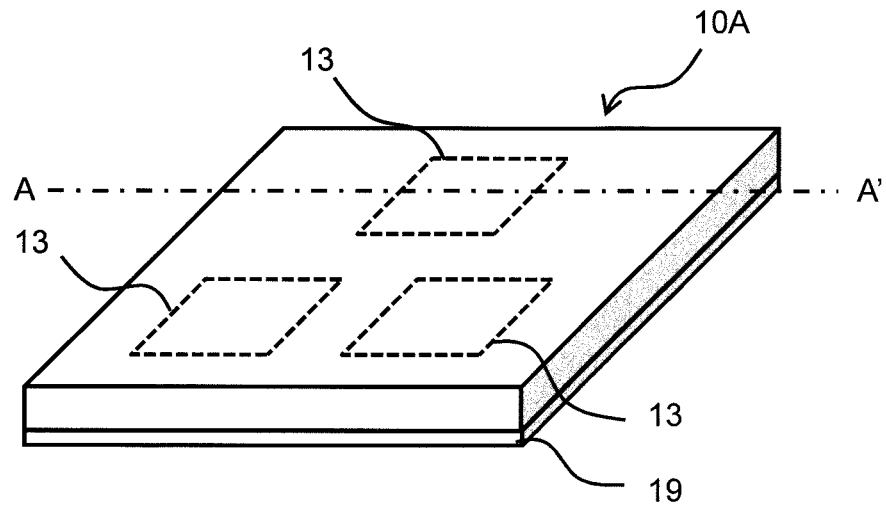
FIG. 6A is a schematic diagram illustrating a wearable device 10A according to a modification of the present invention, and is a perspective view of the wearable device 10A.
Figure 6B:
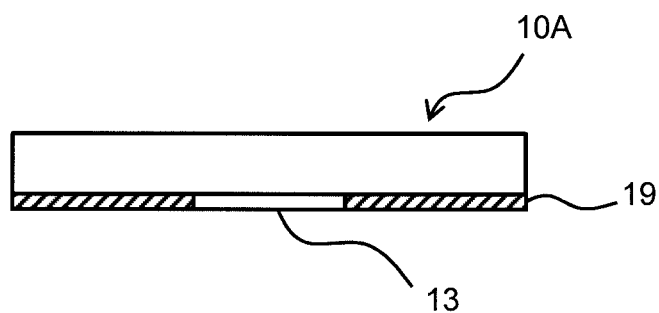
FIG. 6B is a cross-sectional view of the wearable device 10A in a line segment AA' of FIG. 6A.

In FIG. 4A, the wearable device 10 is illustrated as a watch-type device, but the device is not limited thereto. A wearable device according to the present invention may be of any shape as long as the device is wearable by the driver 1. FIG. 6 is a schematic diagram illustrating a wearable device 10A according to a modification of the present embodiment. FIG. 6A is a perspective view of the wearable device 10A, and FIG. 6B is a cross-sectional view of the wearable device 10A in the line segment AA' of FIG. 6A. The wearable device 10A is a flat, preferably sheet-shaped device. Although the wearable device 10A having a rectangular sheet structure is shown in FIG. 6A, the wearable device 10A may be a disk-shaped structure. The wearable device 10A is affixed to the body of the driver 1 (e.g., the chest) via an adhesive layer 19. For example, a known gel or gel sheet can be used for the adhesive layer 19. From the point of view of the contact between the sensor 13 and the body of the driver 1, the adhesive layer 19 is preferably not arranged on the surface on which the sensor 13 contacts the body of the driver 1. From the viewpoint of the adhesion between the wearable device 10A and the body of the driver 1, it is preferable to cover all the portions of the surface of the wearable device 10A which is in close contact with the body of the driver 1 where the sensor 13 is not disposed with the adhesive layer 19. In order to prevent the sensors 13 from interfering with each other, the adhesive layer 19 is preferably made of an insulating material.

As shown in FIG. 6B, when the wearable device 10A is in close contact with the body of the driver 1, it is preferable that a surface on which the sensor 13 contacts the body of the driver 1 and a surface on which the adhesive layer 19 contacts the body of the driver 1 are substantially flush with each other. However, when the adhesive layer 19 is fluid or resilient, the adhesive layer 19 may be arranged such that the adhesive layer 19 protrudes more toward the body side of the driver 1 than the sensor 13 (lower side in FIG. 6B), that is, the sensor 13 is recessed more than the adhesive layer 19 prior to applying the wearable device 10A to the body of the driver 1. Other configurations may have the same configuration as the configuration of the wearable device 10 shown in FIG. 4B, and a detailed description thereof will be omitted. The configuration using the adhesive layer 19 can also be applied to the wearable device 10, which is a watch-type device. The adhesive layer 19 can improve the adhesion between the wearable device 10 and a wrist of the driver 1 to improve the accuracy of the biometric information acquired from the driver 1 by the sensor 13.

Figure 6C:
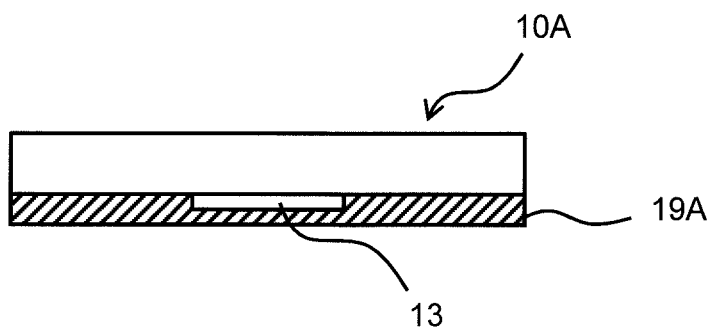
FIG. 6C is a cross-sectional view of the wearable device 10A in the line segment AA' of FIG. 6A.

Here, a modification of the arrangement of the adhesive layer 19 will be described. FIG. 6C is a cross-sectional view of the wearable device 10A in the line segment AA' of FIG. 6A. In FIG. 6C, an adhesive layer 19A is disposed on the entire lower surface of the wearable device 10A to cover the sensor 13. The adhesive layer 19A is a gel having conductivity, and a known gel can be used. The adhesive layer 19 may be a gel sheet having electrical conductivity. When the sensor 13 is an optical sensor such as a pulse oxymeter, it is preferable that the adhesive layer 19A has light transmittance. When a plurality of sensors 13 is arranged, it is preferable that the adhesive layer 19A is arranged separately so that the adhesive layer 19A covering the neighboring sensors 13 does not touch to prevent the sensors 13 from interfering with each other. In FIG. 6A, FIG. 6B and FIG. 6C, the rectangular sensor 13 is illustrated, but number, shapes, and arrangement of the sensor 13 included in the wearable device 10A can be arbitrarily selected and are not particularly limited.

Figure 7:
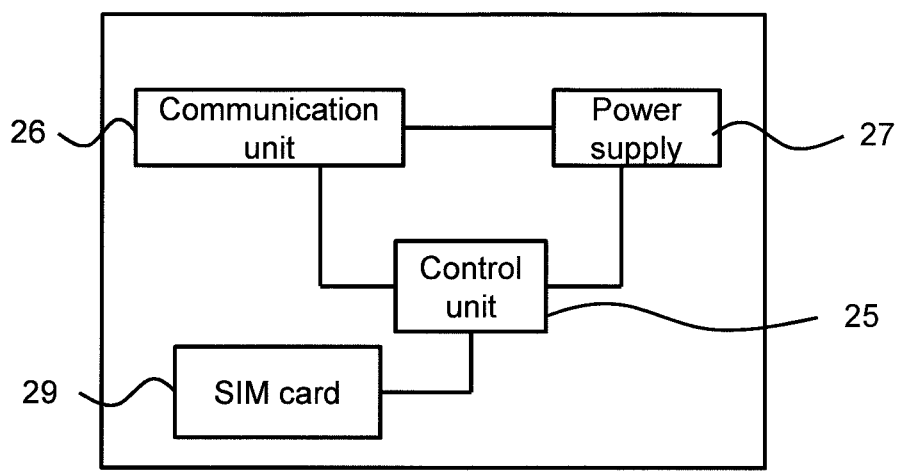
FIG. 7 is a block diagram illustrating a dedicated transceiver 20 according to one embodiment of the present invention.

FIG. 7 is a block diagram illustrating a dedicated transceiver 20 according to an embodiment of the present invention. The dedicated transceiver 20 includes, for example, a control unit 25, a communication unit 26, a power supply 27, and a SIM-card 29. In one embodiment, the control unit 25 is a device for controlling the dedicated transceiver 20, e.g., a central processing unit. The control unit 25 includes programs for controlling the dedicated transceiver 20. In one embodiment, the control unit 25 may include an operating system which controls the dedicated transceiver 20.

In one embodiment, the communication unit 26 is a device in which the dedicated transceiver 20 communicates with external devices, e.g., a communication line which can be used as mobile communication systems. A communication unit conforming to a wireless communication standard such as Wi-Fi or Bluetooth (registered trademark) is also provided, but the present invention is not limited thereto. The communication unit 26 is assigned a physical address (MAC address) and can identify the dedicated transceiver 20 from the physical address. Therefore, in the embodiment described above, the driver 1 is specified based on the physical address assigned to the communication unit 16 of the wearable device 10, but the driver 1 may be specified based on the physical address assigned to the dedicated transceiver 20.

In one embodiment, the dedicated transceiver 20 may be connected to a plurality of the wearable devices 10. That is, a plurality of the wearable devices 10 may be connected to the safe driving assistance in-vehicle device 30 and the server 101 via one dedicated transceiver 20. In this situation, the driver 1 may be identified based on the physical address assigned to the wearable device 10, rather than the physical address assigned to the dedicated transceiver 20.

In one embodiment, the power supply 27 is a common battery and is a repeatedly chargeable and dischargeable power supply that supplies the power to the devices located on the dedicated transceiver 20. For example, the power supply 27 may be provided with a connecting terminal and supplied with power externally to charge. The power supply 27 may be an externally power supplied and charged without contact by wireless power transmission. The power supply 27 is preferably lightweight and large in volume, but is not particularly limited. Therefore, the dedicated transceiver 20 is not limited to use only in the vehicle 50 but is portable.

<Safe Driving Assistance in-Vehicle Device 30>

Figure 8:
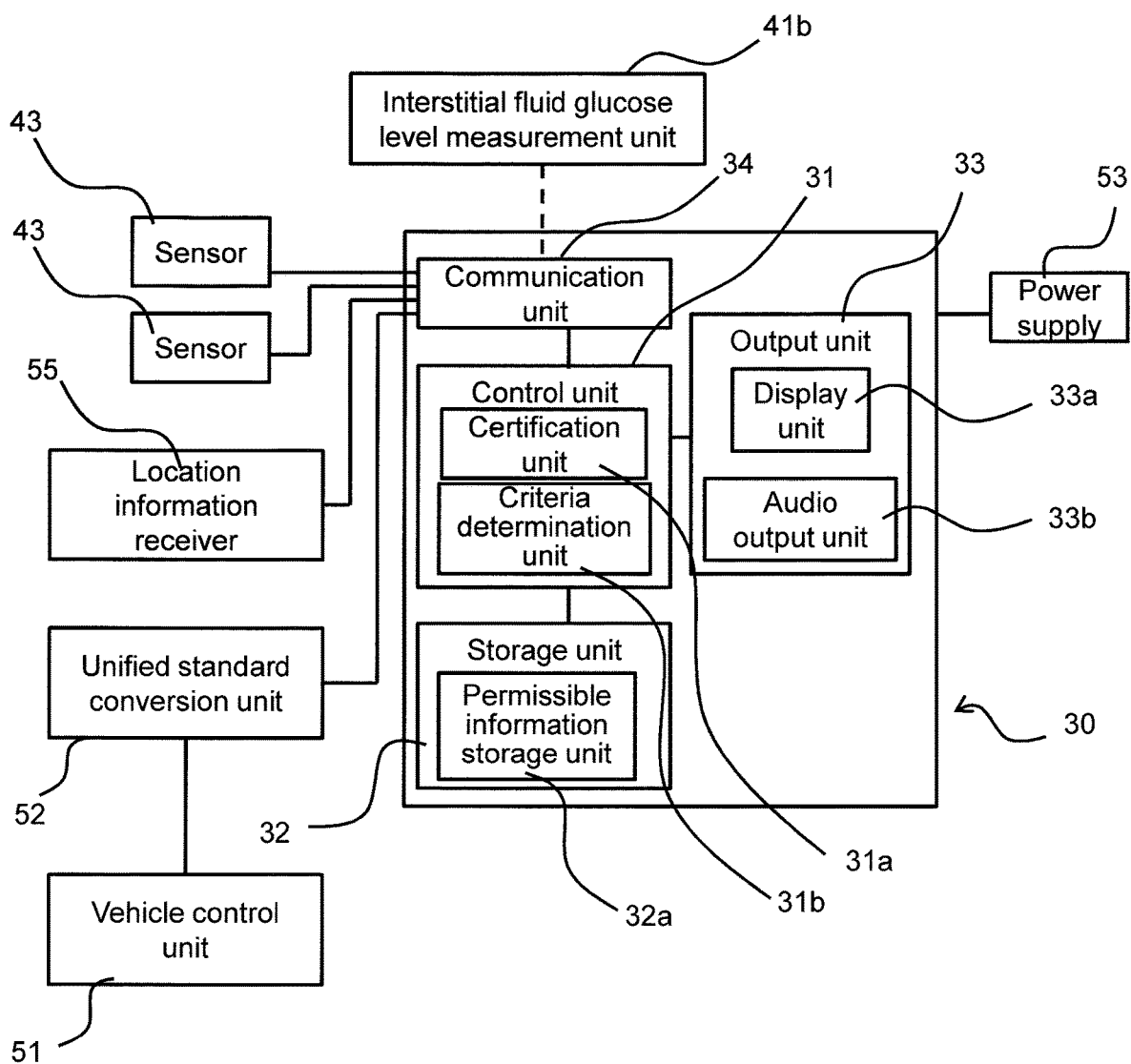
FIG. 8 is a block diagram illustrating a safe driving assistance in-vehicle device 30 according to an embodiment of the present invention.

In one embodiment, the safe driving assistance in-vehicle device 30 is mounted on the vehicle 50 and connects to the vehicle control unit 51 of the vehicle 50. FIG. 8 is a block diagram illustrating a safe driving assistance in-vehicle device 30 according to an embodiment of the present invention. The safe driving assistance in-vehicle device 30 includes, for example, a control unit 31 including a certification unit 31a and a criteria determination unit 31b, a storage unit 32 including a permissible information storage unit 32a, an output unit 33 includes a display unit 33a and an audio output unit 33b, and a communication unit 34. Power is supplied to the safe driving assistance in-vehicle device 30 from the power supply 53 of the vehicle 50. The power supply 53 is, for example, a battery mounted on the vehicle 50. In one embodiment, the safe driving assistance in-vehicle device 30 connects the communication unit 34 to the interstitial fluid glucose level measurement unit 41b and other sensors 43. In one embodiment, the safe driving assistance in-vehicle device 30 connects to a location information receiver 55. In one embodiment, the safe driving assistance in-vehicle device 30 is preferably connected to the vehicle control unit 51 via a unified standard conversion unit 52.

In one embodiment, the control unit 31 is a device for controlling the safe driving assistance in-vehicle device 30, for example, a central processing unit (CPU). The control unit 31 includes a program for controlling the safe driving assistance in-vehicle device 30. The program for controlling the safe driving assistance in-vehicle device 30 is stored in the storage unit 32 and executed by the control unit 31. In one embodiment, the control unit 31 may include an operating system (OS) which controls the safe driving assistance in-vehicle device 30, and application programs or modules which function on the safe driving assistance system 100.

In one embodiment, the control unit 31 includes the certification unit 31a and the criteria determination unit 31b. The certification unit 31a is an application program or a module for certificating the driver 1. The certification unit 31a can identify the driver 1 based on the physical address assigned to the communication unit 16 of the wearable device 10 or the physical address assigned to the communication unit 26 of the dedicated transceiver 20. When the certification information of the driver 1 includes a code or the like indicating that the driver 1 is permitted to drive a vehicle, the certification unit 31a may allow the vehicle control unit 51 to operate the vehicle 50 by the driver 1. When the certification information of the driver 1 does not include a code or the like indicating that the driver 1 is allowed to drive a vehicle, even when the driver 1 operates to start the engine of the vehicle 50, the engine starting operation may be shut off via the vehicle control unit 51. When the certification unit 31a includes information which can identify the driver 1, for example, a body weight of the driver 1, a fingerprint information, and a facial information in the certification information of the driver 1, and is provided with a sensor 43 identifiable these, it is possible to certificate the driver 1 based on these certification information.

In one embodiment, the criteria determination unit 31b is an application program or a module for controlling the operating status of the vehicle 50 by comparing the permissible information of the driver 1 stored in the server 101 or the wearable device 10 with at least the biometric information measured from the interstitial fluid glucose concentration measurement part 41b and the sensor 13 of the wearable device 10. As described above, the permissible information of the driver 1 is set by the healthcare professional, and the permissible information is stored in the server 101 or the wearable device 10. In one embodiment, the safe driving assistance in-vehicle device 30 may receive the permissible information of the driver 1 from the server 101 or the wearable device 10 via the communication unit 34 and store them in the permissible information storage unit 32a. The safe driving assistance in-vehicle device 30 can read the permissible information of the driver 1 from the permissible information storage unit 32a and compare it with the measured biometric information by storing the permissible information of the driver 1 in the permissible information storage unit 32a, while the driver 1 is driving the vehicle 50.

In one embodiment, when the driver 1 is a hypoglycemic patient, the criteria determination unit 31b may compare the measured biometric information with the permissible information based on, for example, blood glucose levels and at least one of a heart rate, a skin temperature change, or no increase in sweat rate. For example, at least one of a heart rate greater than or equal to a predetermined number, a skin temperature change greater than or equal to a predetermined number, an increase in sweat rate greater than or equal to a predetermined number, or a blood glucose level less than 70 mg/dL is detected, the risk of subsequent central nervous system manifestation is increased. Therefore, when it is stored that the heart rate is less than the predetermined number, the skin temperature change is less than the predetermined number, the sweat rate is less than the predetermined number, or the blood sugar level is 70 mg/dL or more, as the permissible information in the permissible information storage unit 32a, the criteria determination unit 31b does not transmit a special signal to the vehicle control unit 51 or transmits a signal for permitting the driving if the heart rate of the driver 1 measured by the sensor 13 is less than the predetermined number, the skin temperature change is less than the predetermined number, the increase in sweat rate is less than the predetermined number, or the blood sugar level is 70 mg/dL or more. On the other hand, when at least one of the heart rate of the driver 1 measured by the sensor 13 being equal to or higher than the predetermined number, the skin temperature change being equal to or higher than the predetermined number, the increase in sweat rate being equal to or higher than the predetermined number, or the blood glucose level being less than 70 mg/dL is detected, the criteria determination unit 31b transmits signals to the output unit 33 to display and output sounds for alerting for glucose supplementation, as will be described later. Further, when at least one of the heart rate of the driver 1 measured by the sensor 13 of the predetermined number or more, the skin temperature change of the predetermined number or more, the increase in sweat rate of the predetermined number or more, and the blood sugar level of less than 70 mg/dL are detected, the criteria determination unit 31b transmits signals to the output unit 33 to display and output sounds for alerting to stop, as will be described later.

For example, when a blood glucose level less than 50 mg/dL is detected, it indicates that hypoglycemia has already occurred and there is a very high-risk of unconsciousness state in the absence of sympathetic symptoms. Therefore, when it is stored that the blood glucose level is 50 mg/dL or more as the permissible information in the permissible information storage unit 32a, the criteria determination unit 31b does not transmit a special signal to the vehicle control unit 51 or transmits a signal for permitting the operation if the blood glucose level of the driver 1 measured by the interstitial fluid glucose concentration measurement part 41b is 50 mg/dL or more. On the other hand, when the blood glucose level of the driver 1 measured by the interstitial fluid glucose concentration measurement part 41b is detected to be less than 50 mg/dL, the criteria determination unit 31b transmits a signal for stopping the vehicle 50 to the vehicle control unit 51, as described later.

In one embodiment, the permissible information may be used based on the rate of blood glucose fluctuation, i.e., a rate of drop in blood glucose. A sharp drop in blood glucose level increases the risk of hypoglycemia, even when the absolute value is high. When the criteria determination unit 31b detects a sudden drop in the blood glucose level, it may send a signal to the output unit 33 for displaying an alert and outputting sounds.

In one embodiment, the output unit 33 includes, for example, the display unit 33a and the audio output unit 33b. The display unit 33a is, for example, a display device such as a display or a head-up display. The audio output unit 33b may be a speaker in the vehicle, it may be a separate speaker disposed in the safe driving assistance in-vehicle device 30. The display unit 33a and the audio output unit 33b can output a video and sound for alerting the driver 1, or output a video and sound for warning the driver 1 in response to the signal received from the criteria determination unit 31b. Furthermore, when the vehicle 50 is stopped urgently the audio output unit 33b may output a sound for alerting the surroundings to the outside of the vehicle.

In one embodiment, since the communication unit 34 performs wireless communication with the wearable device 10 or the interstitial fluid glucose concentration measurement part 41b, for example, a communication means conforming to a wireless communication standard such as Wi-Fi or Bluetooth (registered trademark) is provided, but is not limited thereto. The communication unit 34 may include a communication unit corresponding to a serial bus standard, such as a universal serial bus (USB) connected to the sensor 43, the location information receiver 55, and the vehicle control unit 51. The communication unit 34 may be connected to the wearable device 10 via the dedicated transceiver 20.

Figure 9:
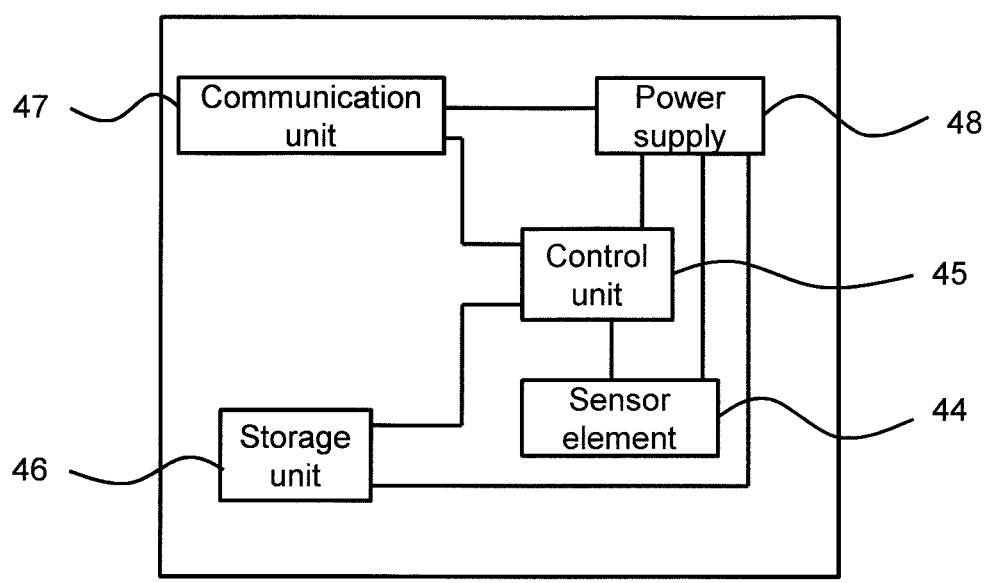
FIG. 9 is a block diagram illustrating a measurement part 41 according to an embodiment of the present invention.

In one embodiment, the sensor 43 includes any sensor other than at least one of a pulse meter, a thermometer, or a diaphoremeter of the sensor 13, and the interstitial fluid glucose concentration measurement part 41b. FIG. 9 is a block diagram of a interstitial fluid glucose concentration measurement part 41b and a sensor 43 according to an embodiment of the present invention. The interstitial fluid glucose concentration measurement part 41b and the sensor 43 include, for example, a sensor element 44, a control unit 45, a storage unit 46, a communication unit 47, and a power supply 48. The sensor element 44 is an element for detecting a biometric information, and a known sensor element can be used. The control unit 45 processes the signals detected by the sensor element 44. The storage unit 46 is arranged as required, and the storage unit 46 is a memory for temporarily storing the signal detected by the sensor element 44.

To perform wireless communication with the safe driving assistance in-vehicle device 30, the communication unit 47 includes, for example, a communication unit conforming to a wireless communication standard such as Wi-Fi or Bluetooth (registered trademark), but is not limited thereto. The communication unit 47 may include a communication unit corresponding to a serial bus standard, such as a universal serial bus (USB) connected to the safe driving assistance in-vehicle device 30. The power supply 48 may be the power supply 53 of the vehicle 50 and may be externally supplied and charged without contact by wireless power transmission. It may be a replaceable power supply such as a dry cell battery.

In one embodiment, the sensor 43 may exemplify, but is not limited to, a pressure gauge disposed in the driver's seat, a pressure gauge disposed in the handle 40, an electrocardiogram disposed in the handle 40, a fingerprint sensor disposed in the handle 40, a face certification sensor disposed opposite the driver's seat, and the like. For example, when the information of the driver 1 includes the weight of the driver 1, the certification unit 31a can compare the weight of the driver 1 measured by the pressure gauge with the weight of the driver 1 included in the certification information of the driver 1 to determine that the driver 1 in the driver's seat is a certificated driver by arranging a pressure gauge as the sensor 43 in the driver's seat. When the permissible information includes fingerprint information of the driver 1, the certification unit 31a can compare the fingerprint of the driver 1 measured by the fingerprint sensor with the fingerprint of the driver 1 included in the certification information of the driver 1 to determine that the driver 1 holding the handle 40 is a certificated driver by disposing a fingerprint sensor on the handle 40 as the sensor 43. When the permissible information includes information on the face of the driver 1, the certification unit 31a can compare the face of the driver 1 recognized by the face certification sensor with the face of the driver 1 included in the certification information of the driver 1 to determine that the driver 1 in the driver's seat is a certificated driver by arranging the face certification sensor at a position facing the sensor 43. That is, it is possible to prevent the driver other than the certificated driver 1 from driving.

When the pressure gauge is disposed on the handle 40 as the sensor 43, in the case where the driver 1 releases both hands from the handle 40 during operation, the criteria determination unit 31b may determine that abnormality is occurred in the driver 1 from the change in pressure measured by the pressure gauge.

Figure 10:
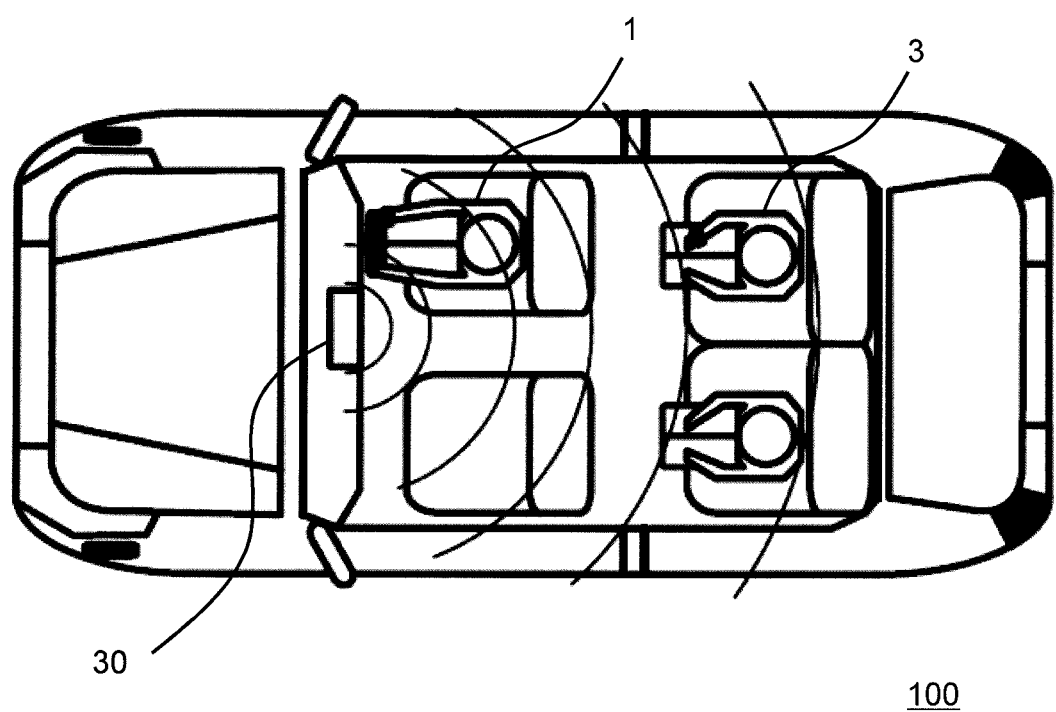
FIG. 10 is a schematic diagram illustrating a method of identification of the wearable device 10 according to one embodiment of the present invention.

In one embodiment, the criteria determination unit 31b may confirm that the driver 1 is in the driver's seat from the strength of the radio wave which is detected by the communication unit 34 received from the wearable device 10. FIG. 10 is a schematic diagram illustrating an identification method of the wearable device 10 according to an embodiment of the present invention. A passenger 3 other than the driver 1 may also be wearing the wearable device 10. In this case, by comparing the strength of the radio wave received from the wearable device 10 on which the driver 1 wears to be detected by the communication unit 34 and the strength of the radio wave received from the wearable device 10 on which the passenger 3 wears, it is possible to measure the distance from the safe driving assistance in-vehicle device 30. Therefore, the criteria determination unit 31b may confirm that the driver 1 is in the driver's seat using the distance from the safe driving assistance in-vehicle device 30. When an abnormality occurs in the biometric information of the passenger 3 wearing the wearable device 10, the control unit 31 may notify the abnormality of the passenger 3 to the terminal 111 for healthcare professionals, the terminal 131 for administrative organ, the terminal 141 for company, or the terminal 151 for transportation facilities from the physical addresses and the biometric information of the wearable device 10 received by the communication unit 34 via the server 101. In one embodiment, the safe driving assistance system 100, the safe driving assistance system 100a, and the safe driving assistance system 100b not only support the safe driving of the driver 1 but can also be used to manage and rescue the health condition of the passenger 3 when the wearable device 10 is worn.

The vehicle control unit 51 is a computer or module mounted on the vehicle 50, which is a control device for controlling the vehicle 50. Since the vehicle control unit 51 has a known vehicle control mechanism, a detailed description thereof will be omitted. In one embodiment, the vehicle control unit 51 is connected to the safe driving assistance in-vehicle device 30 and controls the vehicle 50 based on a signal received from the safe driving assistance in-vehicle device 30 other than the driving operation by the driver 1. In one embodiment, the vehicle control unit 51 includes safe driving support techniques such as automatic braking, pedal misapplication prevention, lane departure warning, cruise control, and the like.

Since the vehicle control unit 51 is a control device unique to the vehicle 50, it has a different configuration for each vehicle manufacturer or vehicle type. When the safe driving assistance in-vehicle device 30 is connected directly to the vehicle control unit 51, the safe driving assistance in-vehicle device 30 must be configured for the vehicle control unit 51, which varies from vehicle manufacturer or vehicle type. Alternatively, the vehicle control unit 51 needs to be changed so that the vehicle control unit 51 can use a signal received from the safe driving assistance in-vehicle device 30.

The unified standard conversion unit 52 is a computer or module which converts the signals output by the safe driving assistance in-vehicle device 30 for the vehicle control unit 51, which varies from vehicle manufacturer or the vehicle type. In one embodiment, it is preferable to place the unified standard conversion unit 52 to connect the safe driving assistance in-vehicle device 30 and the vehicle control unit 51. Thus, the unified standard conversion unit 52 is preferably a highly versatile device which can be connected to the safe driving assistance in-vehicle device 30 and the vehicle control unit 51. Therefore, it is preferable that the device is constituted by a unified standard of the automotive industry, which can control the vehicle control unit 51 which differs for each vehicle manufacturer or vehicle type. For example, it is preferably a device which is composed of a standard which is unified by the Japan Automobile Manufacturers Association, and a standard which is unified by the government agencies such as the Ministry of Land, Infrastructure, Transport and Tourism and/or the Ministry of Economy, Trade and Industry and the Japan Automobile Manufacturers Association. In the present embodiment, it has been described as a configuration for placing the unified standard conversion unit 52 in the vehicle 50, but is not limited thereto, the unified standard conversion unit 52 may be located within the safe driving assistance in-vehicle device 30. The arrangement of the unified standard conversion unit 52 enables the existing vehicle to be retrofitted with the safe driving assistance in-vehicle device 30 according to the present invention and supports safe driving by the driver 1 without purchasing a new vehicle.

The location information receiver 55 may be a known car navigation system. In one embodiment, location information receiver 55b acquires location information of the vehicle 50, traffic information, and map information near the point where the vehicle 50 runs, and transmits the information to the safe driving assistance in-vehicle device 30, but is not limited thereto.

<A Certification Method of a Driver>

Figure 11:
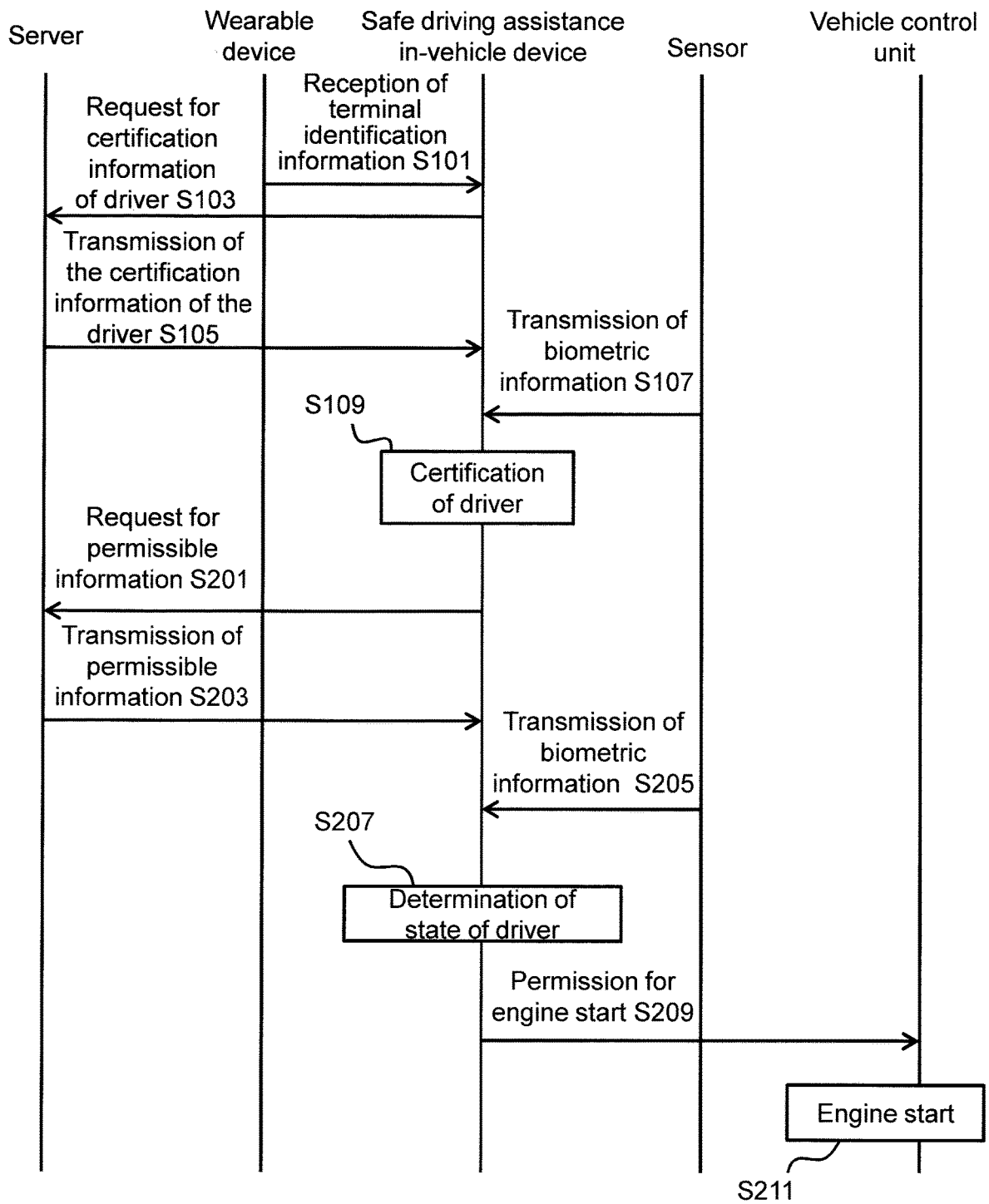
FIG. 11 is a flowchart illustrating a method of certification of a driver 1 using the safe the driving assistance system 100 according to an embodiment of the present invention.

A certification method of the driver 1 using the safe driving assistance system 100 according to an embodiment of the present invention will be described. FIG. 11 is a flowchart for illustrating the method of certification of the driver 1 using the safe driving assistance system 100 according to an embodiment of the present invention. The safe driving assistance in-vehicle device 30 receives the terminal identification information of the wearable device 10 (S101). The safe driving assistance in-vehicle device 30 requests the certification information from the server 101 (S103). The server 101 transmits the stored certification information of the driver 1 to the safe driving assistance in-vehicle device 30 (S105). In one embodiment, the certification information of the driver 1 includes biometric information identifying the driver 1, such as weight, fingerprints, facial information, etc. of the driver 1, in addition to the name and ID of the driver 1. When the certification information of the driver 1 is stored in the wearable device 10, the safe driving assistance in-vehicle device 30 may request and receive the certification information of the driver 1 from the wearable device 10.

The safe driving assistance in-vehicle device 30, for example, receive the biometric information of the driver 1 from the sensor 43 arranged in the driver's seat (S107). As the biometric information of the driver 1 acquired by the sensor 43, a weight, a fingerprint, and an image of the face of the driver 1 is exemplified, but is not limited thereto. The safe driving assistance in-vehicle device 30 compares the weight, fingerprint information, or face information of the driver 1 included in the certification information with the weight, fingerprint, or face images of the driver 1 received from the sensor 43, and certificates the driver 1 when the weight, fingerprint, or face images match or roughly match (S109).

Figure 12:
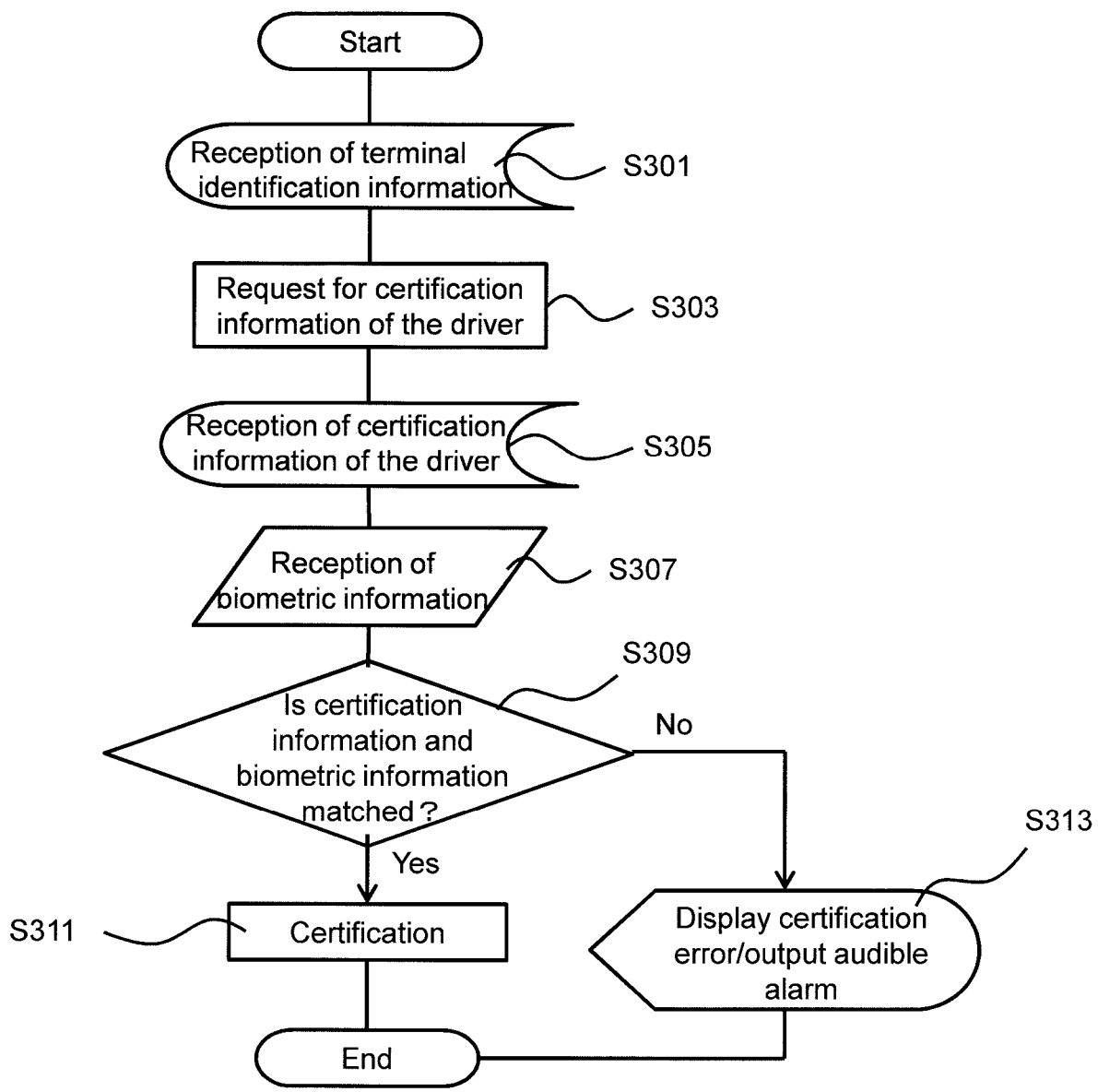
FIG. 12 is a flowchart illustrating a method of certification of the driver 1 in the safe driving assistance in-vehicle device 30 according to an embodiment of the present invention.

FIG. 12 is a flowchart illustrating a certification method of the driver 1 in the safe driving assistance in-vehicle device 30 according to an embodiment of the present invention. The safe driving assistance in-vehicle device 30 receives the terminal identification information of the wearable device 10 (S301). The certification unit 31a requests the certification information of the driver 1 to the server 101 or the wearable device 10 (S303). The certification unit 31a receives the certification information of the driver 1 from the server 101 or the wearable device 10 (S305). That is, it is confirmed that the certification information of the driver 1 corresponding to the terminal identification information of the wearable device 10 exists in the server 101 or the wearable device 10 (first certification process). At this time, the permissible information storage unit 32a may store the certification information of the driver 1. At this time, the certification unit 31a may certificate the driver 1 when the certification information of the driver 1 includes a code or the like indicating that the driver 1 is permitted to drive the vehicle. The certification unit 31a may determine whether the sensor 13, the interstitial fluid glucose concentration measurement part 41b, and the sensor 43 mounted on the vehicle 50 coincide with a sensor for monitoring the driver 1 included in the certification information of the driver 1. The certification unit 31a may transmit an error signal to the output unit 33 when the sensor 13, the interstitial fluid glucose concentration measurement part 41b, and the sensor 43 mounted on the vehicle 50 do not coincide with the sensor included in the certification information of the driver 1.

The safe driving assistance in-vehicle device 30 receives the biometric information of the driver 1 from the sensor 43 arranged in the driver's seat, as described above (S307). The safe driving assistance in-vehicle device 30 compares the biometric information such as the weight, fingerprint information, or face information of the driver 1 included in the certification information with the biometric information such as the weight, fingerprint or face images of the driver 1 received from the sensor 43 (S309). Here, it is preferable that the permissible difference between the biometric information of the driver 1 included in the certification information of the driver 1 and the biometric information of the driver 1 received from the sensor 43 is preset to, for example, 10% and 5% of the body weight of the driver 1 included in the certification information in view of a change due to clothing or the like when the difference is based on the body weight. It is preferable to determine in advance the permissible difference for certificating the driver 1 in consideration of a finger scratch or the like when the fingerprint of the driver 1 is used as a reference, and in consideration of glasses, a hairstyle, a beardie, or the like when the face of the driver 1 is used as a reference. When the biometric information of the driver 1 included in the certification information matches or roughly matches the biometric information of the driver 1 received from the sensor 43, the safe driving assistance in-vehicle device 30 certificates the driver 1 (S311) (second certification process). On the other hand, when the difference between the biometric information of the driver 1 included in the certification information and the biometric information of the driver 1 received from the sensor 43 exceeds a permissible difference, the safe driving assistance in-vehicle device 30 transmits an error signal to the output unit 33, and the display unit 33a indicates a certification error (S313). In one embodiment, the audio output unit 33b may output an audible alarm in response to an error signal. Such a certification of the driver 1 may be performed by the certification unit 31a, and the criteria determination unit 31b may compare the biometric information of the driver 1 included in the certification information and the biometric information of the driver 1 received from the sensor 43.

<A Determination Method of a State of a Driver>

In one embodiment, the safe driving assistance in-vehicle device 30 may determine whether the driver 1 is ready to drive after certificating the driver 1. The safe driving assistance in-vehicle device 30 requests the permissible information of the driver 1 to the Server 101 (S201). The server 101 transmits the stored permissible information to the safe driving assistance in-vehicle device 30 (S203). The safe driving assistance in-vehicle device 30 receives, for example, the pulse rate as the heart rate from the sensor 13, and receives the blood glucose level from the interstitial fluid glucose concentration measurement part 41b (S205). The safe driving assistance in-vehicle device 30 compares the permissible information with the pulse rate received from the sensor 13 and the blood glucose level received from the interstitial fluid glucose concentration measurement part 41b (S207). The safe driving assistance in-vehicle device 30 will permit the vehicle control unit 51 to start the engines of the vehicle 50 when these biometric information are within the permissible ranges (S209). Upon receiving a certification from the safe driving assistance in-vehicle device 30, the vehicle control unit 51 can start the engine of the vehicle 50 (S211). When the permissible information of the driver 1 is stored in the wearable device 10, the safe driving assistance in-vehicle device 30 may request and receive the permissible information of the driver 1 from the wearable device 10.

Figure 13:
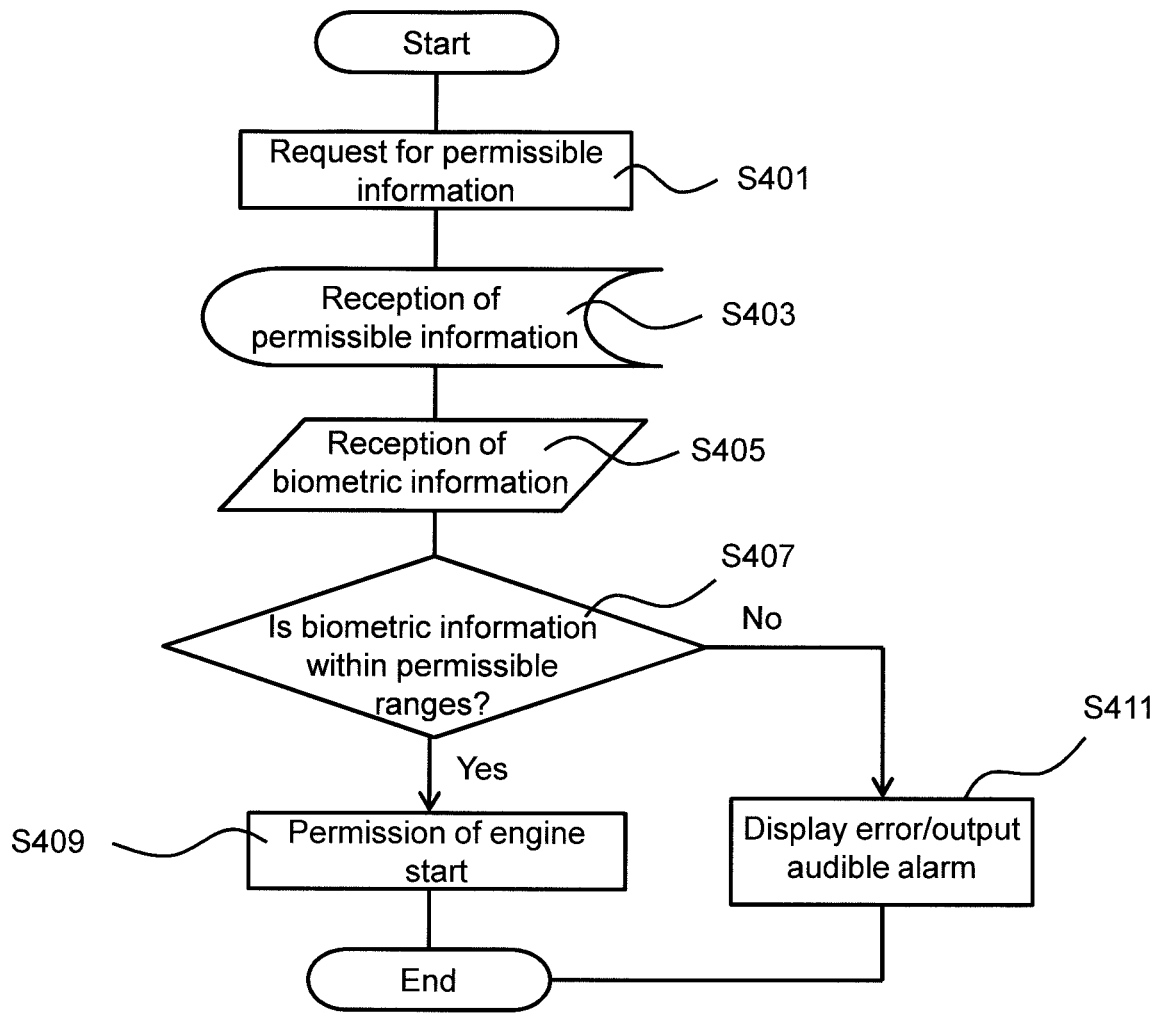
FIG. 13 is a flow diagram illustrating a determination method of a state of the driver 1 in the safe driving assistance in-vehicle device 30 according to an embodiment of the present invention.

FIG. 13 is a flowchart illustrating a determination method of a state of the driver 1 in the safe driving assistance in-vehicle device 30 according to an embodiment of the present investigation. The criteria determination unit 31b of the safe driving assistance in-vehicle device 30 requests the server 101 or the wearable device 10 for the permissible information of the driver 1 (S401). The safe driving assistance in-vehicle device 30 receives the permissible information from the server 101 or the wearable device 10. The permissible information of the driver 1 may be stored in the permissible information storage unit 32a (S403). The criteria determination unit 31b receives, for example, the pulse rate as the heart rate from the sensor 13, and receives as the blood glucose level from the interstitial fluid glucose concentration measurement part 41b (S405). The criteria determination unit 31b compares the permissible information with the pulse rate received from the sensor 13 and the blood glucose level received from the interstitial fluid glucose concentration measurement part 41b (S407). The criteria determination unit 31b allows the vehicle control unit 51 to start the engine of the vehicle 50 when these biometric information are within the permissible ranges.

In one embodiment, when the criteria determination unit 31b determines that the heart rate measured by the pulse meter is less than a predetermined number and the blood glucose level measured by the interstitial fluid glucose level meter is greater than or equal to a predetermined number, the criteria determination unit 31b transmits a signal for permitting the vehicle control unit 51 to start the engine (S409). On the other hand, when the heart rate measured by the pulse meter is equal to or greater than the predetermined number, or when the blood glucose level measured by the interstitial fluid glucose level meter is less than the predetermined number, the criteria determination unit 31b does not transmit a signal for permitting the vehicle control unit 51 to start the engine. In one embodiment, when the criteria determination unit 31b determines that the heart rate measured by the pulse meter is greater than or equal to a predetermined number, or that the blood glucose level measured by the interstitial fluid glucose meter is less than a predetermined number, the criteria determination unit 31b transmits an error signal to the output unit 33 and the display unit 33a indicates a certification error. In one embodiment, the audio output unit 33b may output an audible alarm in response to an error signal (S411).

In the present embodiment, in order to determine whether or not the driver 1 is ready to drive, the permissible information is compared with the pulse rate received from the sensor 13 and the blood glucose level received from the interstitial fluid glucose concentration measurement part 41b. However, the present invention is not limited thereto, and the biometric information measured from the sensor 13 may be a value indicating the presence or absence of sympathetic symptoms and may be, for example, a value indicating a change in skin temperature or a change in sweat rate.

<Safe Driving Assistance Method>

Figure 14:
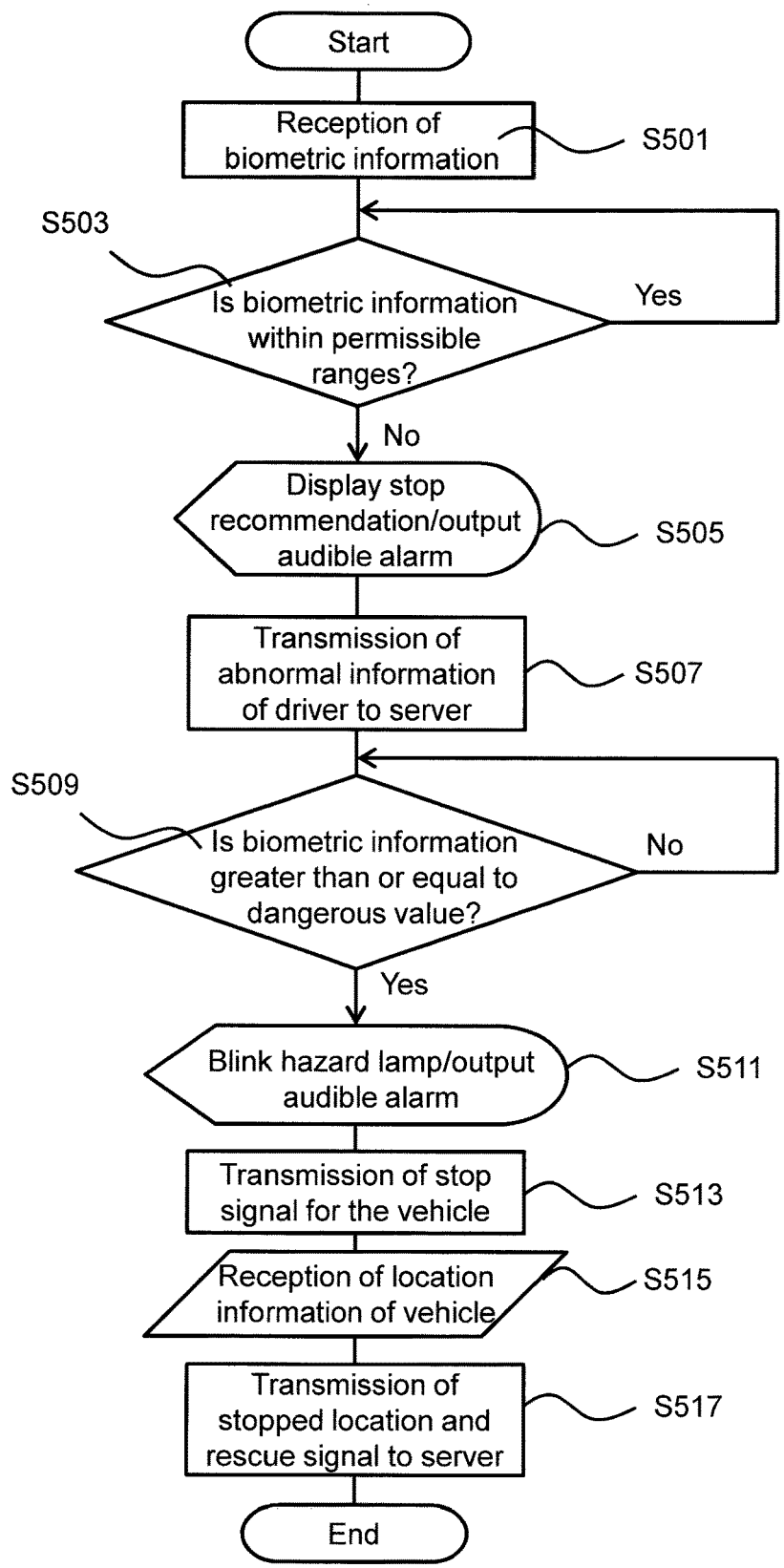
FIG. 14 is a flowchart illustrating a safe driving support method according to the safe driving assistance system 100 according to an embodiment of the present invention.

FIG. 14 is a flowchart illustrating a safe driving assistance method performed by the safe driving assistance system 100 according to an embodiment of the present invention. When the driver 1 is driving the vehicle 50, the criteria determination unit 31b receives, for example, the pulse rate as the heart rate from the sensor 13, and receives the blood glucose level from the interstitial fluid glucose concentration measurement part 41b (S501). The criteria determination unit 31b compares the permissible information of the driver 1 stored in the permissible information storage unit 32a with the biometric information received from the sensor 13 and the interstitial fluid glucose concentration measurement part 41b (S503). The criteria determination unit 31b does not control the vehicle control unit 51 when the heart rate measured by the pulse meter is less than a predetermined number and the blood glucose level measured by the interstitial fluid glucose level meter is equal to or greater than a predetermined number. That is, the driver 1 can normally operate the vehicle 50.

On the other hand, when the heart rate measured by the pulse meter is greater than or equal to a predetermined number, or when the blood glucose level measured by the interstitial fluid glucose level meter is less than a predetermined number, the criteria determination unit 31b transmits a signal to the output unit 33 to make a recommendation for glucose supplementation, and the display unit 33a displays the recommendation for glucose supplementation. In one embodiment, the audio output unit 33b may output a warning tone in response to a signal recommending sugar supplementation (S505). In one embodiment, the safe driving assistance in-vehicle device 30 may transmit abnormal information of the driver 1 via the communication unit 34 to the server 101 (S507).

In addition, when the heart rate measured by the pulse meter is greater than or equal to a predetermined number and the blood glucose level measured by the interstitial fluid glucose level meter is less than a predetermined number, the criteria determination unit 31b transmits a signal to the output unit 33 to make a stop recommendation, and the display unit 33a displays the stop recommendation. In one embodiment, the audio output unit 33b may alert a sound in response to a signal recommending a stop (S505). In one embodiment, the safe driving assistance in-vehicle device 30 may transmit the abnormal information of the driver 1 via the communication unit 34 to the server 101 (S507).

In one embodiment, the server 101 may notify the terminal 111 for healthcare professionals of abnormality of the driver 1 and transmit the biometric information of the driver 1 or the like. The server 101 may notify the terminal 131 for administrative organ of the abnormality of the driver 1 and may transmit the biometric information of the driver 1 or the like. In one embodiment, the server 101 may notify the abnormality of the driver 1 to the terminal 141 for company when the terminal 111 for healthcare professionals does not respond after notifying the abnormality of the driver 1 or when the operation of requesting the support or rescue of the driver 1 is not performed to the terminal 131 for administrative organ or the terminal 141 for company. The server 101 may notify the abnormality of the driver 1 to the terminal 151 for transportation facilities when the terminal 111 for healthcare professionals does not respond after notifying the abnormality of the driver 1 or when the terminal 111 for healthcare professionals does not perform operations for requesting the support or rescue of the driver 1 to the terminal 131 for administrative organ or the terminal 151 for transportation facilities.

The criteria determination unit 31b determines whether the biometric information is not greater than or equal to the dangerous value (S509). That is, the criteria determination unit 31b transmits an emergency signal to the vehicle control unit 51 when the blood glucose level measured by the interstitial fluid glucose concentration measurement part 41b is less than 50 mg/dL, the vehicle control unit 51 blinks the hazard lamp of the vehicle 50, and the audio output unit 33b outputs a sound for calling attention to the surroundings to the outside of the vehicle when the vehicle 50 stops urgently (S511).

The criteria determination unit 31b transmits a stop signal for the vehicle 50 to the vehicle control unit 51, and the vehicle control unit 51 stops the vehicle 50 (S513). In one embodiment, the control unit 31 may receive a location information in which the vehicle 50 has stopped from the location information receiver 55 and transmit the location information in which the vehicle 50 has stopped to the server 101 via the communication unit 34 (S515). The control unit 31 may transmit rescue signals to the server 101 (S517). The server 101 may notify the terminal 111 for healthcare professionals of the abnormality of the driver 1 and transmit the biometric information or the like of the driver 1. The server 101 may transmit the rescue signal of the driver 1 to the terminal 131 for administrative organ and transmit the biometric information or the like of the driver 1. In one embodiment, the server 101 may transmit the rescue signal of the driver 1 to the terminal 141 for company when the terminal 111 for healthcare professionals does not respond after notifying the abnormality of the driver 1 or when the operation requesting rescue of the driver 1 is not performed to the terminal 131 for administrative organ or the terminal 141 for company. The server 101 may transmit the rescue signal of the driver 1 to the terminal 151 for transportation facilities when the terminal 111 for healthcare professionals does not respond after notifying the abnormality of the driver 1 or when the operation of requesting rescue of the driver 1 is not performed from the terminal 111 for healthcare professionals to the terminal 131 for administrative organ or the terminal 151 for transportation facilities.

In the present embodiment, the permissible information is compared with the pulse rate from the sensor 13 and the blood glucose level received from the interstitial fluid glucose concentration measurement part 41b to determine whether or not the driver 1 is ready to drive. However, the present invention is not limited thereto, and the biometric information measured from the sensor 13 may be a value indicating the presence or absence of sympathetic symptoms and may be, for example, a value indicating a change in skin temperature or a change in sweat rate.

In this way, since the safe driving assistance system 100 according to the embodiment of the present invention controls the operation status of the vehicle based on the determination result of the criteria determination unit, it is possible to support during the vehicle operation considering the health status of the driver. In particular, driving of the vehicle by a hypoglycemic patient can be supported.

<Safely Stop Assistance Method>

Figure 15:
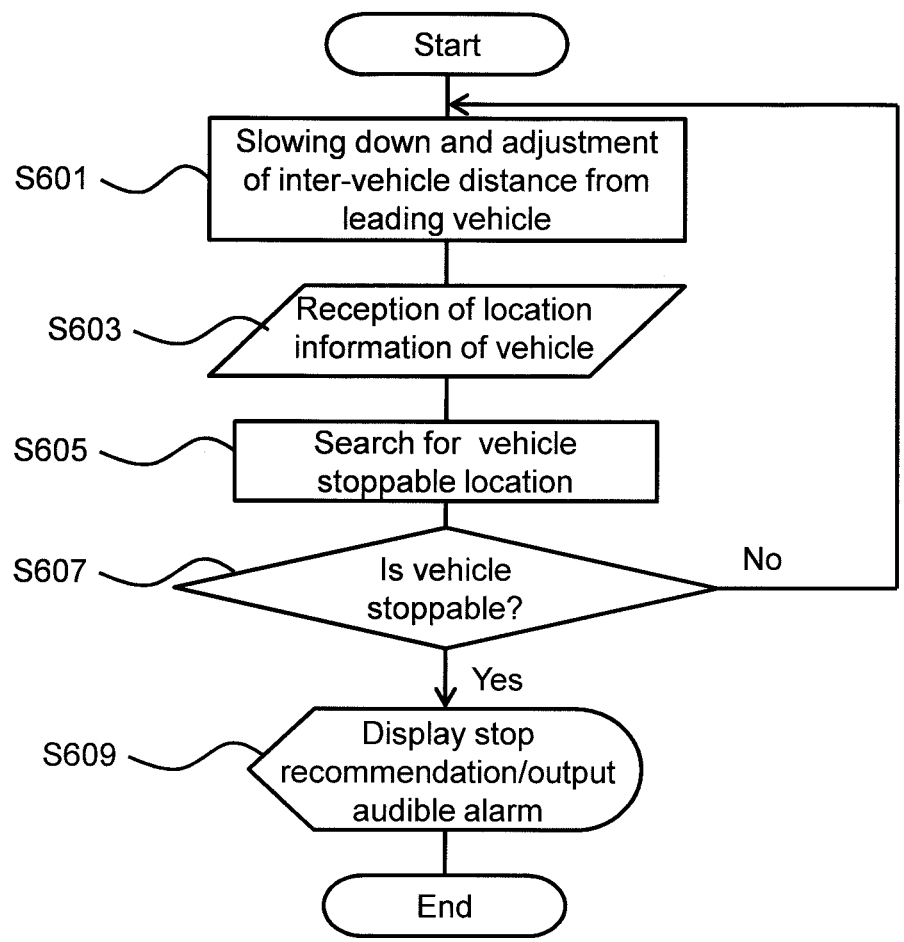
FIG. 15 is a flowchart illustrating a safe stop support method according to an embodiment of the present invention.
Figure 16:
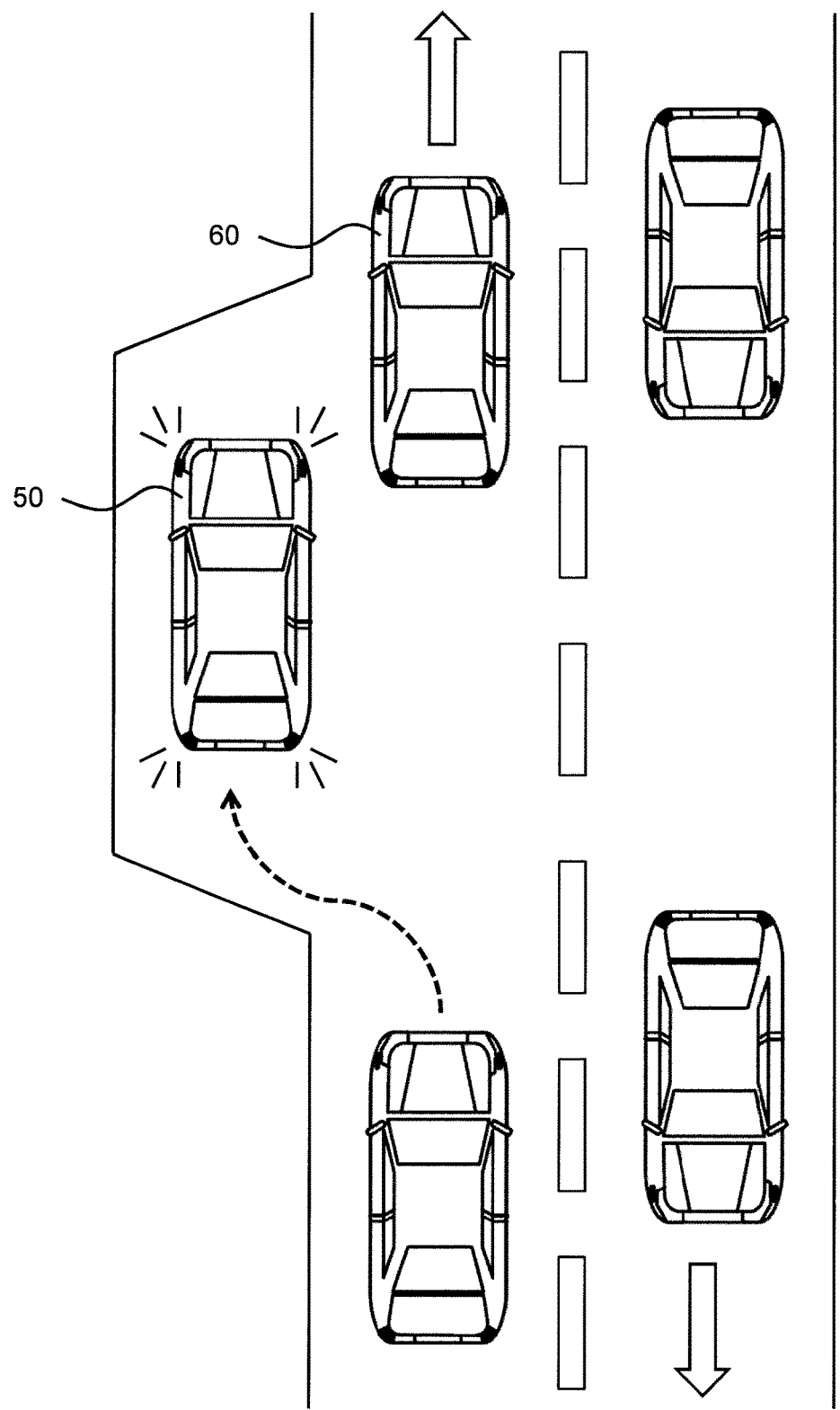
FIG. 16 is a schematic diagram illustrating a safe stop support method according to an embodiment of the present invention.

FIG. 15 is a flowchart illustrating a safe stop assistance method according to an embodiment of the present invention. FIG. 16 is a schematic diagram illustrating a safe stop assistance method according to an embodiment of the present invention. In one embodiment, when the criteria determination unit 31b determines that the heart rate measured by the pulse meter is greater than or equal to a predetermined number and that the blood glucose level measured by the interstitial fluid glucose level meter is less than a predetermined number, the control unit 31 requests the vehicle control unit 51 to slow down the vehicle 50 and adjust the distance to a leading vehicle 60. The vehicle control unit 51 slows down the vehicle 50 according to a prescribed operating conditions in response to the requirement of the control unit 31 and adjusts the inter-vehicle distance from the leading vehicle 60 (S601). The control of the vehicle 50 by the vehicle control unit 51 can be performed by using a cruise control function. The Location information receiver 55 receives a location information of the vehicle 50 (S603). The location information receiver 55 searches where the vehicle 50 can stop. That is, the location information receiver 55 searches for a location where the vehicle 50 can safely stop by comparing the location information of the currently running the vehicle 50 with the map information (S605). For example, it may be a stopping lane, a road shoulder which can be stopped, a sideway, a convenience store, or the like. The location where the vehicle 50 is stopped may be any location, such as a vacant area or a garden in private residence in which it does not obstruct the passage of a subsequent vehicle. When the location information receiver 55 detects a location where the vehicle 50 can be safely stopped (S607), the control unit 31 makes a stop recommendation to the display unit 33a and displays the location information on the location information receiver 55, i.e., a display device of a car navigation system, and displays a guidance map. The audio output unit 33b may prompt the driver 1 to stop, and output a sound for guiding the vehicle 50 (S609). In this way, the driver 1 can safely stop the vehicle 50, as shown in FIG. 16.

Figure 17:
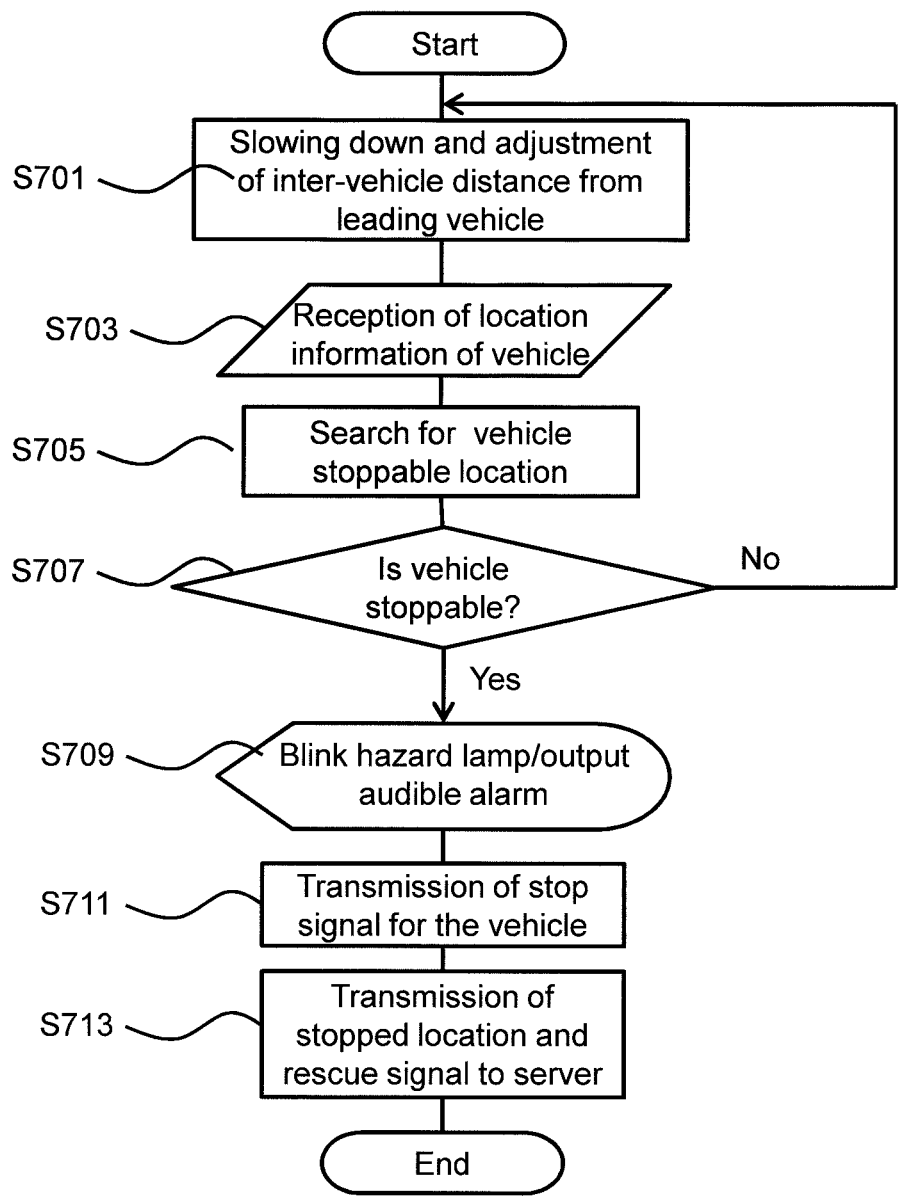
FIG. 17 is a flowchart illustrating a safe stop support method according to an embodiment of the present invention.

FIG. 17 is a flowchart illustrating a safe stop support method according to an embodiment of the present invention. In one embodiment, when the criteria determination unit 31b has a blood glucose level measured by the interstitial fluid glucose concentration measurement part 41b of less than 50 mg/dL, the control unit 31 requests the vehicle control unit 51 to slow down the vehicle 50 and adjust the distance to the leading vehicle 60. The vehicle control unit 51 slows down the vehicle 50 according to a prescribed operating conditions in response to the requirement of the control unit 31 and adjusts the inter-vehicle distance from the leading vehicle 60 (S701). The location information receiver 55 receives a location information of the vehicle 50 (S703). The location information receiver 55 searches where the vehicle 50 can stop. That is, the location information receiver 55 searches for a location where the vehicle 50 can safely stop by comparing the location information of the currently running the vehicle 50 with the map information (S705). For example, it may be a stopping lane, a road shoulder which can be stopped, or the like. When the location information receiver 55 detects the location which can safely stop the vehicle 50 (S707), the control unit 31 requests the vehicle control unit 51 to stop, and the vehicle control unit 51 may stop the vehicle 50 based on the location information at which the vehicle 50 can stop. At this time, the vehicle control unit 51 blinks the hazard lamp of the vehicle 50, and the audio output unit 33b outputs the sound to attract attention to the surroundings when the vehicle 50 makes an emergency stop (S709).

The criteria determination unit 31b transmits a stop signal for the vehicle 50 to the vehicle control unit 51, and the vehicle control unit 51 stops the vehicle 50 (S711). In one embodiment, the control unit 31 may receive the location information from the location information receiver 55 in which the vehicle 50 has stopped, and transmitted the location information in which the vehicle 50 has stopped to the server 101 via the communication unit 34. The control unit 31 may transmit a rescue signal to the server 101 (S713). The server 101 may notify the terminal 111 for healthcare professionals of the abnormality of the driver 1 and transmit the biometric information or the like of the driver 1. The server 101 may transmit the rescue signal of the driver 1 to the terminal 131 for administrative organ and transmit the biometric information or the like of the driver 1. In one embodiment, the server 101 may transmit the rescue signal of the driver 1 to the terminal 141 for company when the terminal 111 for healthcare professionals does not respond after notifying the driver 1 of the abnormality or the operation requesting rescue of the driver 1 is not performed to the terminal 131 for administrative organ or the terminal 141 for company. The server 101 may transmit the rescue signal of the driver 1 to the terminal 151 for transportation facilities when the terminal 111 for healthcare professionals does not respond after notifying the abnormality of the driver 1 or when the operation of requesting rescue of the driver 1 is not performed from the terminal 111 for healthcare professionals to the terminal 131 for administrative organ or the terminal 151 for transportation facilities.

In one embodiment, the vehicle control unit 51 travels to a position where the vehicle can be stopped by the cruise control function while adjusting the inter-vehicle distance from the leading vehicle 60, and the vehicle 50 may be stopped at the position where the vehicle can be stopped using images around the vehicle 50 acquired from the camera mounted on the vehicle 50 at the location information where the vehicle can be stopped. When the location information receiver 55 determines that there is no other vehicle around the vehicle 50, or when it determines from the imaging analysis of the camera mounted on the vehicle 50 that there is no other vehicle around the vehicle 50, the vehicle control unit 51 may immediately stop the vehicle 50.

As described above, the safe driving assistance system 100 according to the embodiment of the present invention controls the operation status of the vehicle based on the determination result of the criteria determination unit, it is possible to support to safely stop the vehicle.

[Safe Driving Assistance System to Support Motor Vehicle Driving by Epileptic Patients]

Examples of the use of the safe driving assistance system according to the present invention as a safe driving assistance system for supporting the driving of a motor vehicle by epileptic patients will now be described. A detailed description of the configuration described in the above embodiment is omitted, and a characteristic configuration in the present embodiment will be specifically described.

In one embodiment, when the driver 1 is an epilepsy patient, for example, the permissible information based on the heart rate and the brain wave can be used. For example, when the heart rate is greater than or equal to a predetermined number, the risk of subsequent epileptic seizures increases. Therefore, the permissible information may be that the heart rate is less than a predetermined number. In the present embodiment, the heart rate as the permissible information is determined in advance by the medical professional based on the diagnosis result of the driver 1 by the medical professional. Detection of brain wave patterns characteristic in epileptic seizure, selected from the group consisting of a sharp wave, a spike, a polyspikes, a spike-and-slow-wave complex, a polyspike-and-slow-wave complex, and a fourteen and six Hz positive spikes, in the brain wave, indicates that an epileptic seizure has occurred and there is a very high-risk of unconsciousness state. For this reason, it may be permissible information that no brain wave patterns specific to epileptic seizure selected from the group consisting of a sharp wave, a spike, a polyspikes, a spike-and-slow-wave complex, a polyspike-and-slow-wave complex, and a fourteen and six Hz positive spikes are detected in the brain wave. In one embodiment, permissible information based on the heart rate variability, i.e., rate of increase in the heart rate, may be used. A rapid increase in the heart rate increases the risk of subsequent epileptic seizures. In the present embodiment, it is preferable that the permissible information is periodically adjusted by a medical professional because there are individual differences in the heart rate and the heart rate fluctuation which are a sign of an epilepsy occurrence and the permissible information is affected by the patient's physical condition.

See FIG. 1 is referred. In the present embodiment, the safe driving assistance system 100 includes a brain wave measurement unit 41A for monitoring the brain wave of the driver 1. The brain wave measurement unit 41A is connected to the communication unit 34 of the safe driving assistance in-vehicle device 30. In one embodiment, the criteria determination unit 31b functions as application programs or modules for comparing the permissible information of the driver 1 stored in the server 101 or the wearable device 10 with the biometric information measured from at least the sensors 13 of the wearable device 10 and/or the brain wave measurement unit 41A to control the operating status of the vehicle 50. The rest of the configuration of the safe driving assistance system 100 may have the same configuration as that described in the above embodiment, and a detailed explanation thereof is omitted.

<Wearable Device>

The wearable device 10 may have the same configuration as that described in the above embodiment, and a detailed explanation thereof is omitted.

Figure 18:
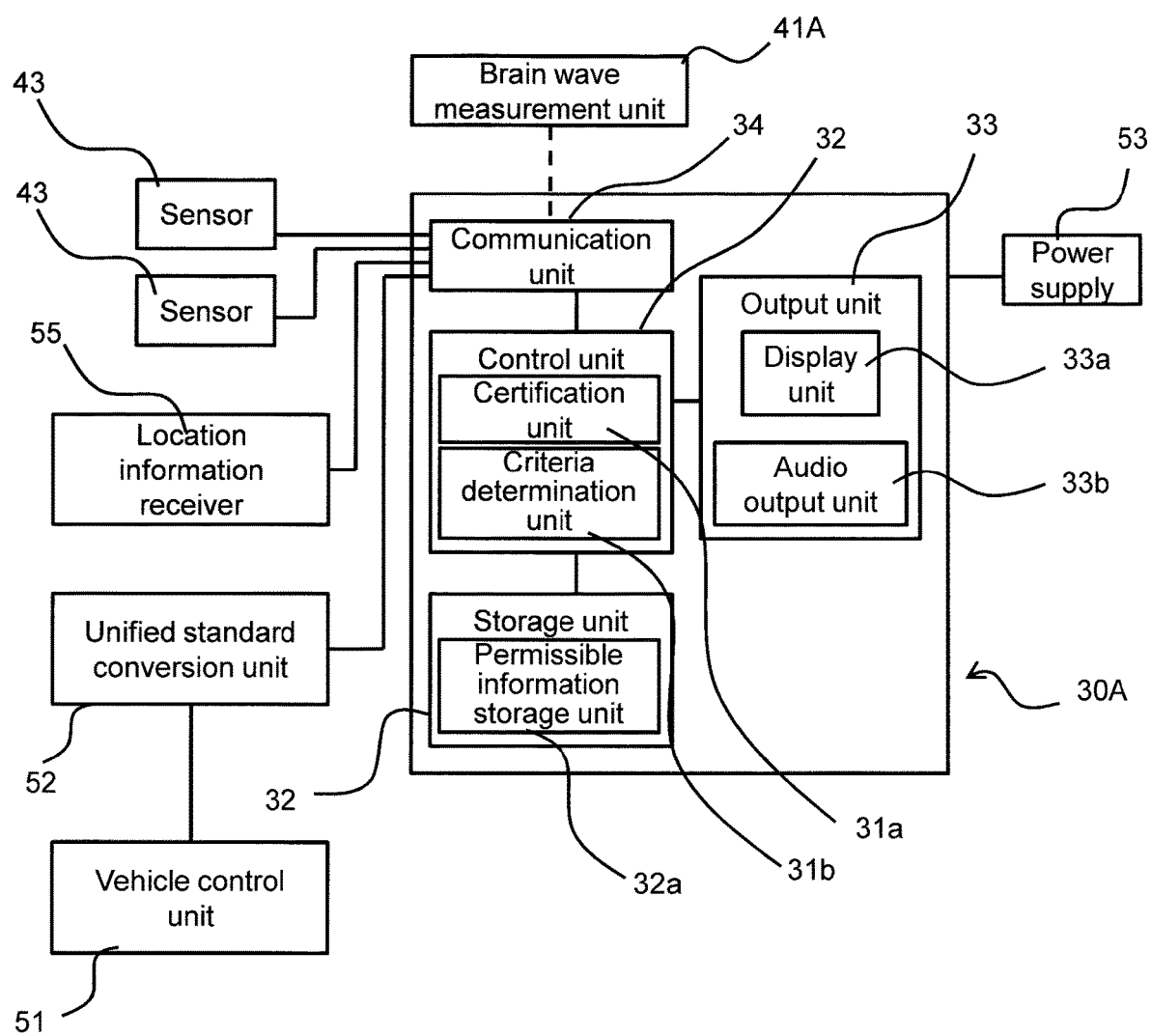
FIG. 18 is a block diagram illustrating a safe driving assistance in-vehicle device 30A according to an embodiment of the present invention.

FIG. 18 is a block diagram illustrating a safe driving assistance in-vehicle device 30A according to an embodiment of the present invention. For the same configuration as the safe driving assistance in-vehicle device 30, a detailed description thereof will be omitted. In one embodiment, when the driver 1 is an epilepsy patient, the criteria determination unit 31b may compare the measured biometric information with a permissible information based on, for example, the heart rate and brain wave. For example, when the heart rate is greater than or equal to a predetermined number, the risk of subsequent epileptic seizures is increased. Therefore, when the heart rate is less than the predetermined number as the permissible information stored in the permissible information storage unit 32a, the criteria determination unit 31b does not transmit a special signal to the vehicle control unit 51 or transmits a signal for permitting the driving in the case where the heart rate of the driver 1 measured by the sensor 13 is less than the predetermined number. On the other hand, when the heart rate of the driver 1 measured by the sensor 13 is equal to or higher than the predetermined number, the criteria determination unit 31b transmits signals to the output unit 33 for displaying an alert and outputting sounds, as will be described later.

For example, when brain wave patterns characteristic in seizure selected from the group consisting of a sharp wave, a spike, a polyspikes, a spike-and-slow-wave complex, polyspike-and-slow-wave complex, and a fourteen and six Hz positive spikes are detected in the brain wave, this indicates that an epileptic seizure has occurred and the risk of becoming unconscious is very high. Therefore, when the permissible information stored in the permissible information storage unit 32a indicates that a pattern of a brain wave specific to epileptic seizure selected from the group consisting of a sharp wave, a spike, a polyspikes, a spike-and-slow-wave complex, a polyspike-and-slow-wave complex, and a fourteen and six Hz positive spikes is not detected the criteria determination unit 31b does not transmit a special signal to the vehicle control unit 51 or transmits a signal for permitting the operation if the brain wave specific to epileptic seizure selected from the group consisting of a sharp wave, a spike, a polyspikes, a spike-and-slow-wave complex, and a fourteen and six Hz positive spikes is not detected in the brain wave of the driver 1 measured by the brain wave measurement unit 41A. On the other hand, when a pattern of a brain wave peculiar to epileptic seizure selected from the group consisting of a sharp wave, a spike, a polyspikes, a spike-and-slow-wave complex, a polyspike-and-slow-wave complex, and a fourteen and six Hz positive spikes is detected in the brain wave of the driver 1 measured by the brain wave measurement unit 41A, the criteria determination unit 31b transmits a signal for stopping the vehicle 50 to the vehicle control unit 51, as described later. The criteria determination unit 31b can detect the brain wave pattern of the driver 1 by using a known pattern recognition technique. The criteria determination unit 31b may detect the pattern of the brain wave characteristic of epileptic seizure selected from the group consisting of a sharp wave, a spike, a polyspikes, a spike-and-slow-wave complex, a polyspike-and-slow-wave complex, a fourteen and six Hz positive spikes, etc. in the brain wave of the driver 1 measured by the brain wave measurement unit 41A by combining the artificial intelligence technology with the pattern recognition technique.

In one embodiment, the permissible information based on the heart rate variability, i.e., the rate of increase in the heart rate may be used. A rapid increase in the heart rate increases the risk of subsequent epileptic seizures. When the criteria determination unit 31b detects a sudden increase in the heart rate, it may transmit a signal to the output unit 33 to indicate and sound an alert.

In one embodiment, the sensor 43 includes any sensor other than the pulse meter of sensor 13, the brain wave measurement unit 41A. FIG. 9 is a block diagram of the brain wave measurement unit 41A and the sensor 43 according to an embodiment of the present invention. The brain wave measurement unit 41A and the sensor 43 include, for example, the sensor element 44, the control unit 45, the storage unit 46, the communication unit 47, and the power supply 48. The sensor element 44 is a device for detecting the biometric information, and a known sensor element can be used.

In one embodiment, when an electrocardiogram is placed on the handle as the sensor 43, the pulse rate measured by the sensor 43 may be used as the heart rate for the biometric information of the driver 1 instead of the sensor 13 provided in the wearable device 10.

In one embodiment, a certification method of the driver can use the certification method explained in the above-described embodiment. For example, the certification unit 31a may determine whether the sensor 13, the brain wave measurement unit 41A, and the sensor 43 mounted on the vehicle 50 coincide with a sensor for monitoring the driver 1 included in the certification information of the driver 1. The certification unit 31a may transmit an error signal to the output unit 33 when the sensor included in the certification information of driver 1 does not match the sensor 13, the brain wave measurement unit 41A, and the sensor 43 mounted on the vehicle 50.

<A determination method of a state of a Driver>

In one embodiment, the safe driving assistance in-vehicle device 30 may determine whether the driver 1 is ready to drive after certificating the driver 1. The safe driving assistance in-vehicle device 30 requests permissible information of the driver 1 to the server 101 (S201). The server 101 transmits the stored permissible information to the safe driving assistance in-vehicle device 30 (S203). The safe driving assistance in-vehicle device 30 receives the pulse rate as the heart rate from the sensor 13, and receives the brain wave from the brain wave measurement unit 41A (S205). The safe driving assistance in-vehicle device 30 compares the permissible information with the pulse rate received from the sensor 13 and/or the brain wave received from the brain wave measurement unit 41A (S207). The subsequent processing may be performed in the same manner as in the above-described embodiment, and a detailed description thereof is omitted.

FIG. 13 is referred. The same treatment as in the above-described embodiment may be performed until the process S403. The criteria determination unit 31b receives the pulse rate as the heart rate from the sensor 13, and receives the brain wave from the brain wave measurement unit 41A (S405). The criteria determination unit 31b compares the permissible information with the pulse rate received from the sensor 13 and/or the brain wave received from the brain wave measurement unit 41A (S407). The criteria determination unit 31b allows the vehicle control unit 51 to start the engine of the vehicle 50 when these biometric information are within the permissible ranges.

In one embodiment, when the criteria determination unit 31b determines that the heart rate measured by the pulse meter is less than a predetermined number, a signal to allow the engine to start is transmitted to the vehicle control unit 51 (S409). On the other hand, when the heart rate measured by the pulse meter is equal to or higher than the predetermined number, or when the pattern of the brain wave characteristic of epileptic seizure selected from the group consisting of a sharp wave, a spike, a polyspikes, a spike-and-slow-wave complex, a polyspike-and-slow-wave complex, and a fourteen and six Hz positive spikes is detected in the brain wave measured by the brain wave measurement unit 41A, the criteria determination unit 31b does not transmit a signal for permitting the start of the engine to the vehicle control unit 51. In one embodiment, when the criteria determination unit 31b determines that the heart rate measured by the pulse meter is greater than or equal to a predetermined number, or when the brain wave measured by the brain wave measurement unit 41A matches or roughly matches a pattern of the brain wave characteristic of one epileptic seizure selected from the group consisting of a sharp wave, a spike, a polyspikes, a spike-and-slow-wave complex, a polyspike-and-slow-wave complex, and a fourteen and six Hz positive spikes, the criteria determination unit 31b transmits an error signal to the output unit 33, and the display unit 33a indicates a certification error. In one embodiment, the audio output unit 33b may output an audible alarm in response to an error signal (S411).

<Safe Driving Assistance Method>

FIG. 14 is referred. When the driver 1 is driving the vehicle 50, the criteria determination unit 31b receives the pulse rate as the heart rate from the sensor 13, and receives the brain wave from the brain wave measurement unit 41A (S501). The criteria determination unit 31b compares the permissible information of the driver 1 stored in the permissible information storage unit 32a with the biometric information received from the sensor 13 and the brain wave measurement unit 41A (S503). The criteria determination unit 31b does not control the vehicle control unit 51 when the heart rate measured by the pulse meter is less than a predetermined number, and when a brain wave pattern specific to epileptic seizure selected from the group consisting of a sharp wave, a spike, a polyspikes, a spike-and-slow-wave complex, a polyspike-and-slow-wave complex, and a fourteen and six Hz positive spikes is not detected in the brain wave measured by the brain wave measurement unit 41A. That is, the driver 1 can normally operate the vehicle 50.

On the other hand, when the heart rate measured by the pulse meter is equal to or greater than the predetermined number, the criteria determination unit 31b transmits a signal for giving a stop recommendation to the output unit 33, and the display unit 33a displays the stop recommendation. In one embodiment, the audio output unit 33b may output an alert sound in response to a signal recommending a stop (S505). In one embodiment, the safe driving assistance in-vehicle device 30 may transmit the abnormal information of the driver 1 via the communication unit 34 to the server 101 (S507).

The criteria determination unit 31b determines that the biometric information is not greater than or equal to the dangerous value (S509). The criteria determination unit 31b transmits an emergency signal to the vehicle control unit 51 when the heart rate is equal to or higher than a predetermined number or when a pattern of the brain wave characteristic of epileptic seizure selected from the group consisting of a sharp wave, a spike, polyspikes, a spike-and-slow-wave complex, a polyspike-and-slow-wave complex, and a fourteen and six Hz positive spikes is detected in the brain wave measured by the brain wave measurement unit 41A, the vehicle control unit 51 blinks a hazard lamp of the vehicle 50, and the audio output unit 33b outputs a sound for calling attention to the surroundings to the outside of the vehicle when the vehicle 50 stops urgently (S511). In the subsequent process, the process explained in the embodiment described in detail may be performed, and a detailed description thereof is omitted.

In this way, since the safe driving assistance system 100 according to the embodiment of the present invention controls the operation status of the vehicle based on the determination result of the criteria determination unit, it is possible to support during the vehicle operation considering the health status of the driver. In particular, driving of a motor vehicle by an epileptic patient can be supported.

<Safely Stop Assistance Method>

FIG. 17 is referred. In one embodiment, when the criteria determination unit 31b detects a pattern of a brain wave characteristic of epileptic seizure selected from the group consisting of a sharp wave, a spike, a polyspikes, a spike-and-slow-wave complex, a polyspike-and-slow-wave complex, a fourteen and six Hz positive spikes, etc. in the brain wave measured by the brain wave measurement unit 41A, the control unit 31 requests the vehicle control unit 51 to slow down the vehicle 50 and adjust the inter-vehicle distances from the leading vehicle 60. The vehicle control unit 51 slows down the vehicle 50 according to a prescribed operating conditions in response to the request of the control unit 31 and adjusts the inter-vehicle distance from the leading vehicle 60 (S701). In the subsequent process, the process explained in the embodiment described in detail may be performed, and a detailed description thereof is omitted.

[Safe Driving Assistance System to Support Motor Vehicle Driving by Patients with Arrhythmias]

Examples of the use of the safe driving assistance system according to the present invention as a safe driving assistance system for supporting the driving of a motor vehicle by patients with arrhythmias will now be described. A detailed description of the configuration described in the above embodiment is omitted, and a characteristic configuration in the present embodiment will be specifically described.

The permissible information of the driver 1 is the biometric information based criterion for allowing the driver 1 to drive the vehicle. Since the permissible information is also a criterion for restricting the driving by the driver 1, type of the biometric information and an appropriate criterion for each type of the biometric information is set by the healthcare professional according to the illness or the like possessed by the driver 1. In one embodiment, when the driver 1 is a patient with a heart disorder, permissible information based on, for example, the heart rate and the electrocardiographic complex may be used. For example, it is preferable that the certification information of the driver 1 includes, for example, a code indicating that the driver 1 is permitted to drive the vehicle. It may include the information specifying a sensor for monitoring the driver 1 due to a disease or the like of the driver 1. The permissible information of the driver 1 is a criterion based on the biometric information for permitting the driver 1 to drive the vehicle. Since the permissible information is also a criterion for restricting the driving by the driver 1, type of the biometric information and an appropriate criterion for each type of the biometric information is set by the healthcare professional according to the illness or the like possessed by the driver 1. In one embodiment, when the driver 1 is a patient with arrhythmias, for example, permissible information based on the heart rate and the electrocardiographic complex may be used.

The use of permissible information based on the heart rate and the electrocardiographic complex may require a distinction between patients with arrhythmias and the structural and functional changes of the heart when sports is continued, the so-called athletic heart. Since the athletic heart is not necessarily in a pathological state, the permissible information of the patient with the arrhythmia is appropriately set for each driver 1 by the diagnosis by the healthcare professional in consideration of the individual difference. For example, when the heart rate is less than or equal to 50 beats per minute, the risk of bradycardic arrhythmias is increased and risk of fatal conditions such as cardiac arrest is increased. For example, when the heart rate is greater than or equal to 120 beats per minute, risk of tachycardic arrhythmia is increased. Although the heart rate indicating an arrhythmia is appropriately set for each driver 1 by diagnosis by a healthcare professional because there is a difference among individual patients, in one example, the permissible information (first range) may be that the heart rate is faster than 50 beats/minute and less than 120 beats/minute. In one example, a heart rate that is more likely to be a bradycardic arrhythmia may be set to 40 or less, and a heart rate that is more likely to be a tachycardic arrhythmia may be set to 200 or more beats per minute as a dangerous value (a second range). Also, it may be a permissible information that electrocardiographic complex acquired by the electrocardiograph is not classified as ventricular tachycardia or ventricular fibrillation because the risk of cardiac arrest is very high when the electrocardiographic complex acquired by the electrocardiograph is classified as ventricular tachycardia or ventricular fibrillation. Since the heart rate at which bradycardia arrhythmia or the tachycardia arrhythmia occurs differs from individual to individual and is influenced by the physical condition of the patient, it is preferable that the permissible information is periodically adjusted by the health care professional. The rest of the configuration of the safe driving assistance system 100 may have the same configuration as that described in the above embodiment, and a detailed explanation thereof is omitted.

<Wearable Devices>

FIG. 4 is referred. The wearable device 10 includes, for example, the storage unit 11, an electrode (first electrode) 12a, an electrode (second electrode) 12b, the sensor 13, the control unit 15, the communication unit 16, the power supply 17, and the input unit 18, but is not limited thereto. The storage unit 11 is, for example, a memory, and may temporarily store the biometric information acquired from the driver 1 measured by the first electrode 12a and the second electrode 12b and the biometric information acquired from the driver 1 measured by the sensor 13.

In one embodiment, the first electrode 12a and the second electrode 12b are electrodes of an electrocardiograph. For example, when the wearable device 10 is worn on the left wrist, it contacts the wrist of the first electrodes 12a. In this case, by bringing the finger of the right hand (e.g., a thumb or an index finger) into close contact with the second electrode 12b, the wearable device 10 can obtain an electrocardiogram from the driver 1. The wearable device 10 may obtain an electrocardiogram from the driver 1 by attaching the wearable device 10 to the right wrists and bringing the fingers of the left hand into close contact with the second electrodes 12b. The electrocardiograph of the wearable device 10 can obtain an electrocardiogram at a time other than the driving time of the driver 1. That is, an electrocardiogram before driving of the driver 1 can be obtained.

In one embodiment, the sensor 13 is a device for acquiring the biometric information from driver 1, e.g., the pulse meter. In the present embodiment, the pulse rate measured by the pulse meter is treated as substantially synonymous with the heart rate. Therefore, in the present embodiment, it is possible to determine whether the driver 1 is ready to operate the vehicle 50 by comparing the pulse rate measured by the sensor 13 with the permissible information of the driver 1, which will be described later. The sensor 13 may further include other sensors, for example, a sensor for measuring body temperature, blood pressure, oxygen saturation, and the like capable of measuring the biometric information of the driver 1 other than the pulse. The number, shapes, and arrangements of the sensors 13 included in the wearable device 10 can be arbitrarily selected and are not particularly limited. The rest of the configuration of the wearable device 10 may have the same configuration as that described in the above embodiment, and a detailed explanation thereof is omitted. The wearable device 10 may be configured not to include the sensor 13 when the pulse meter equivalent to the sensor 13 is used as the sensor 43 disposed in addition to the wearable device 10 described later.

<Safe Driving Assistance in-Vehicle Device 30B>

Figure 19:
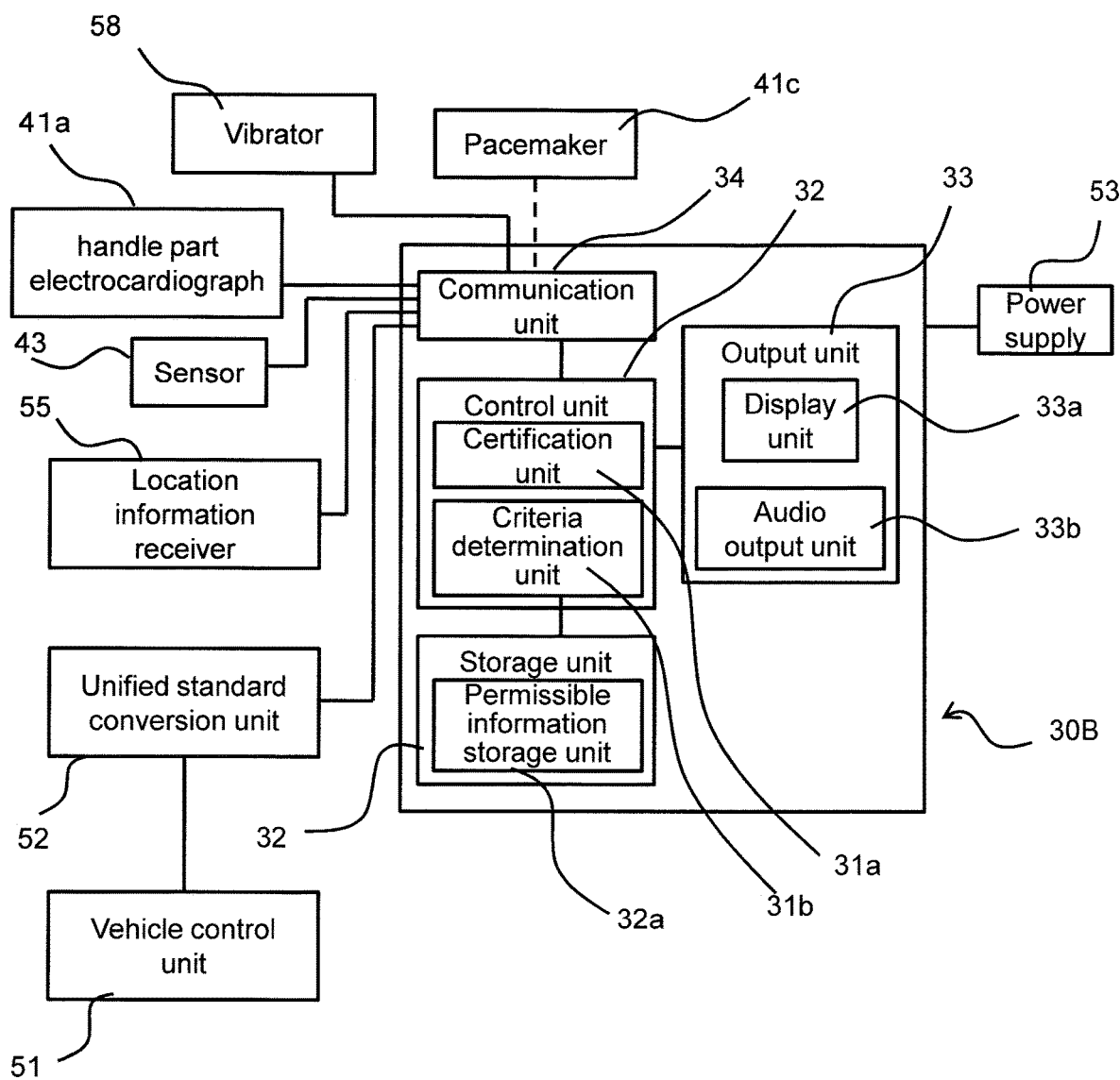
FIG. 19 is a block diagram illustrating a safe driving assistance in-vehicle device 30B according to an embodiment of the present invention.

In one embodiment, the safe driving assistance in-vehicle device 30B is mounted on the vehicle 50 and connects to the vehicle control unit 51 of the vehicle 50. FIG. 19 is a block diagram illustrating the safe driving assistance in-vehicle device 30B according to an embodiment of the present invention. A detailed description of the same configuration as that described in the above embodiment is omitted. The safe driving assistance in-vehicle device 30B includes, for example, a control unit 31 including a certification unit 31a and a criteria determination unit 31b, a storage unit 32 including a permissible information storage unit 32a, an output unit 33 including a display unit 33a and a audio output unit 33b, and a communication unit 34. A power is supplied to the safe driving assistance in-vehicle device 30B from the power supply 53 of the vehicle 50. The power supply 53 is, for example, a battery mounted on the vehicle 50. In one embodiment, the safe driving assistance in-vehicle device 30B connects the communication unit 34 to a handle part electrocardiograph 41a and the rest of the sensors 43. In one embodiment, the safe driving assistance in-vehicle device 30B may be connected to a pacemaker 41c worn by the driver 1 via wired or wireless communication. Instead of the handle part electrocardiograph 41a, a clothing type electrocardiograph may be used. In one embodiment, the safe driving assistance in-vehicle device 30B connects to a location information receiver 55. In one embodiment, the safe driving assistance in-vehicle device 30B is preferably connected to the vehicle control unit 51 via a unified standard conversion unit 52.

In one embodiment, the criteria determination unit 31b is an application program or module for comparing the permissible information of the driver 1 stored in the server 101 or the wearable device 10 with at least the biometric information measured from the sensor 13 and/or the handle part electrocardiograph 41a or pacemaker 41c to control the operating status of the vehicle 50.

In one embodiment, when the driver 1 is an arrhythmic patient, the criteria determination unit 31b, for example, may compare the measured biometric information with the heart rate and an electrocardiographic complex based on the permissible information. For example, when the heart rate falls outside the first range, there is an increased risk of subsequent bradycardia or tachycardia and resulting in unconsciousness state. Therefore, when the heart rate is in the first range as the permissible information stored in the permissible information storage unit 32a, the criteria determination unit 31b does not transmit a special signal to the vehicle control unit 51 or transmits a signal for permitting driving if the heart rate of the driver 1 measured by the sensor 13 is in the first range. On the other hand, when the heart rate of the driver 1 measured by the sensor 13 deviates from the first range, the criteria determination unit 31b transmits a signal to the output unit 33 to display and output a sound for alerting, as will be described later.

When the electrocardiographic complex acquired by the handle part electrocardiograph 41a or the pacemaker 41c is classified as ventricular tachycardia or ventricular fibrillation, there is a very high risk of cardiac arrest. Therefore, when the permissible information stored in the permissible information storage unit 32a indicates that the electrocardiographic complex is not classified as ventricular tachycardia or ventricular fibrillation, the criteria determination unit 31b does not transmit a special signal to the vehicle control unit 51 or transmits a signal for permitting driving if the electrocardiographic complex of the driver 1 measured by the handle part electrocardiograph 41a or the pacemaker 41c is not classified as ventricular tachycardia or ventricular fibrillation. On the other hand, when the electrocardiographic complex of the driver 1 measured by the handle part electrocardiograph 41a or the pacemaker 41c is classified as ventricular tachycardia or ventricular fibrillation, the criteria determination unit 31b transmits a signal for stopping the vehicle 50 to the vehicle control unit 51, as described later.

In one embodiment, when the heart rate is in the second range, the risk of unconsciousness or cardiac arrest is very high. Therefore, when the heart rate is in the second range as the permissible information stored in the permissible information storage unit 32a, the criteria determination unit 31b transmits a signal for stopping the vehicle 50 to the vehicle control unit 51.

In one embodiment, a vibrator 58 may be embedded in the backrest of the vehicle 50 on which the driver 1 sits. For example, when it is detected that the heart rate of the driver 1 is in the second range or when the electrocardiographic complex of the driver 1 measured by the handle part electrocardiograph 41a or the pacemaker 41c is classified as ventricular tachycardia or ventricular fibrillation, the control unit 31 of the safe driving assistance in-vehicle device 30 may drive the vibrator 58 and provide a vibrational stimulus to the back of the driver 1. The heart rhythm of the driver 1 may be restored by providing such a stimulus, and the safe driving of the driver 1 with the arrhythmia can be supported.

In one embodiment, the communication unit 34 includes, but is not limited to, a communication unit conforming to a wireless communication standard such as Wi-Fi or Bluetooth (registered trademark) for wireless communication with the wearable device 10 or the pacemaker 41c. The communication unit 34 may include communication means corresponding to a serial bus standard, such as a universal serial bus (USB) which connects to the handle part electrocardiograph 41a, the sensor 43, the location information receiver 55, the vehicle control unit 51, and the vibrator 58. The communication unit 34 may be connected to the wearable device 10 via the dedicated transceiver 20.

Figure 20A:
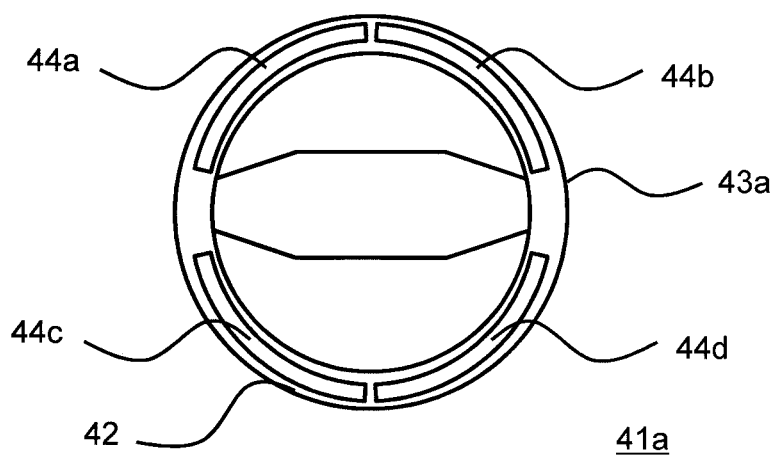
Figure 20B:
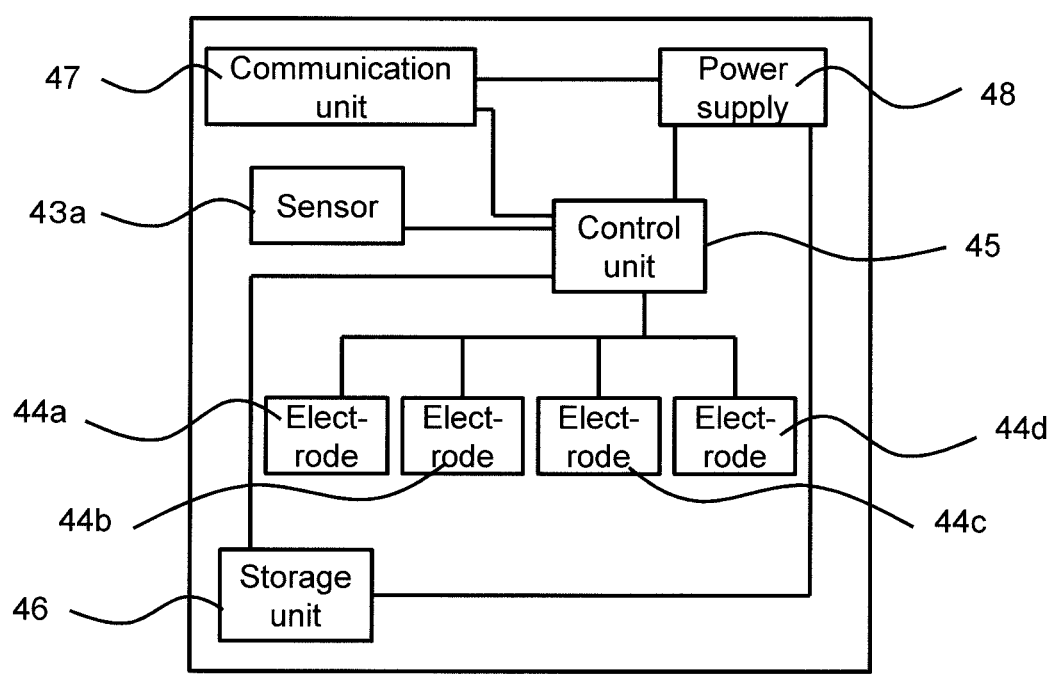
FIG. 20B is a block diagram of the handle part electrocardiograph 41a according to an embodiment of the present invention.

FIG. 20A is a schematic diagram illustrating the handle part electrocardiograph 41a according to an embodiment of the present invention. FIG. 20B is a block diagram illustrating the handle part electrocardiograph 41a according to an embodiment of the present invention. The handle part electrocardiograph 41a includes, for example, an electrode 44a, electrode 44b, electrode 44c, electrode 44d, the control unit 45, the storage unit 46, the communication unit 47, and the power supply 48. The electrodes 44a, 44b, 44c, and 44d are electrodes in contact with the driver's hand, and known electrocardiographic electrodes can be used. The control unit 45 processes signals detected by the electrode 44a, 44b, 44c, and 44d. The storage unit 46 is arranged as required, and is a memory for temporarily storing a signal detected by the electrode 44a, the electrode 44b, the electrode 44c, and the electrode 44d.

In one embodiment, the sensor 43 includes any sensor other than the pulse meter of the sensor 13, the handle part electrocardiograph 41a, and the pacemaker 41c (electrocardiograph). In one embodiment, the pressure gauge disposed in the driver's seat, the pressure gauge disposed in the handle, the fingerprint sensor disposed in the handle, the face certification sensor disposed opposite the driver's seat, and the like can be exemplified, but are not limited thereto.

When the pressure gauge is disposed on the handle as a sensor 43a, the criteria determination unit 31b may determine that an abnormality of the driver 1 has occurred from the change in the pressure measured by the pressure gauge if the driver 1 releases both hands from the handle during operation. The rest of the configuration of the safe driving assistance in-vehicle device 30B may have the same configuration as that described in the above embodiment, and a detailed explanation thereof will be omitted.

<A Certification Method of a Driver>

As the driver certification method, the certification method described in the above embodiment may be used. FIG. 12 is referred. The same process as in the above-described embodiment may be performed until the treatment (S303). The certification unit 31a receives the certification information of the driver 1 from the server 101 or the wearable device 10 (S305). The certification unit 31a may determine whether the sensor 13, the handle part electrocardiograph 41a or the pacemaker 41c, and the sensor 43 mounted on the vehicle 50 coincide with a sensor for monitoring the driver 1 included in the certification information of the driver 1. The certification unit 31a may transmit an error signal to the output unit 33 when the sensor 13, the handle part electrocardiograph 41a or the pacemaker 41c, and the sensor 43 mounted on the vehicle 50 do not match the sensor included in the certification information of the driver 1. As for the subsequent process, the same process as in the above-described embodiment may be performed.

<A Determination Method of a State of a Driver>

In one embodiment, the safe driving assistance in-vehicle device 30 may determine whether the driver 1 is ready to drive after certificating the driver 1. The safe driving assistance in-vehicle device 30 requests the permissible information of the driver 1 to the server 101 (S201). The server 101 transmits the stored permissible information to the safe driving assistance in-vehicle device 30 (S203). The safe driving assistance in-vehicle device 30 receives the pulse rate as the heart rate from the sensor 13, and receives the electrocardiogram from the handle part electrocardiograph 41a or the pacemaker 41c (S205). The safe driving assistance in-vehicle device 30 compares the permissible information with the pulse rate received from the sensor 13 and/or the electrocardiographic complex received from the handle part electrocardiograph 41a or pacemaker 41c (S207). As for the subsequent process, the same process as in the above-described embodiment may be performed.

FIG. 13 is referred. The criteria determination unit 31b of the safe driving assistance in-vehicle device 30 requests the server 101 or the wearable device 10 for the permissible information of the driver 1 (S401). The safe driving assistance in-vehicle device 30 receives the permissible information from the server 101 or the wearable device 10. The permissible information of the driver 1 may be stored in the permissible information storage unit 32a (S403). The criteria determination unit 31b receives the pulse rate as the heart rate from the sensor 13, and receives the electrocardiogram from the handle part electrocardiograph 41a or the pacemaker 41c (S405). The criteria determination unit 31b may receive the heart rate from the handle part electrocardiograph 41a or the pacemaker 41c. The criteria determination unit 31b compare the permissible information with the pulse rate received from the sensor 13 and/or the electrocardiographic complex received from the handle part electrocardiograph 41a or the pacemaker 41c (S407). The criteria determination unit 31b allows the vehicle control unit 51 to start the engine of the vehicle 50 when these biometric information are within the permissible ranges.

In one embodiment, when the criteria determination unit 31b determines that the heart rate measured by the pulse meter or the handle part electrocardiograph 41a or the pacemaker 41c is in the first range, it transmits a signal to the vehicle control unit 51 to allow the engine to start (S409). On the other hand, when the heart rate measured by the pulse meter is out of the first range, or when the electrocardiographic complex of the driver 1 measured by the handle part electrocardiograph 41a or the pacemaker 41c is classified as ventricular tachycardia or ventricular fibrillation, the criteria determination unit 31b does not transmit a signal to the vehicle control unit 51 to allow the engine to start. In one embodiment, when the heart rate measured in the pulse meter is out of the first range, the criteria determination unit 31b transmits an error signal to the output unit 33 and the display unit 33a indicates a certification error. In one embodiment, the audio output unit 33b may output an audible alarm in response to an error signal (S411).

In one embodiment, when the heart rate is in the second range, or when the electrocardiographic complex of the driver 1 as measured by the handle part electrocardiograph 41a or the pacemaker 41c is classified as ventricular tachycardia or ventricular fibrillation, an emergency signal may be sent to the vehicle control unit 51, the vehicle control unit 51 may flash a hazard lamp of the vehicle 50, and the audio output unit 33b may output a sound to inform the surroundings of the emergency to the outside of the vehicle. The server 101 may notify the terminal 111 for healthcare professionals of the abnormality of the driver 1 and may transmit the biometric information or the like of the driver 1. The server 101 may transmit the rescue signal of the driver 1 to the terminal 131 for administrative organ and transmit the biometric information or the like of the driver 1.

<Safe driving assistance method>

FIG. 14 is referred. When the driver 1 is driving the vehicle 50, the criteria determination unit 31b receives the pulse rate as the heart rate from the sensor 13 and receives the electrocardiogram from the handle part electrocardiograph 41a or the pacemaker 41c (S501). The criteria determination unit 31b compares the permissible information of the driver 1 stored in the permissible information storage unit 32a with the biometric information received from the sensor 13 and the handle part electrocardiograph 41a or the pacemaker 41c (S503). The criteria determination unit 31b does not control the vehicle control unit 51 when the heart rate measured by the pulse meter is in the first range and the electrocardiographic complex measured by the electrocardiograph is not classified as ventricular tachycardia or ventricular fibrillation. That is, the driver 1 can normally operate the vehicle 50.

On the other hand, when the heart rate measured by the pulse meter is out of the first range, the criteria determination unit 31b transmits a signal to the output unit 33 to make a stop recommendation, and the display unit 33a displays the stop recommendation. In one embodiment, the audio output unit 33b may output an alert sound in response to a signal recommending a stop (S505). In one embodiment, the safe driving assistance in-vehicle device 30 may transmit the abnormal information of the driver 1 via the communication unit 34 to the server 101 (S507).

In one embodiment, the server 101 may notify the terminal 111 for healthcare professionals of the abnormality of the driver 1 and transmit the biometric information of the driver 1 or the like. The server 101 may notify the terminal 131 for administrative organ of the abnormality of the driver 1 and may transmit the biometric information of the driver 1 or the like. In one embodiment, the server 101 may notify the abnormality of the driver 1 to the terminal 141 for company when the terminal 111 for healthcare professionals does not respond after notifying the abnormality of the driver 1 or when the operation of requesting the support or rescue of the driver 1 is not performed to the terminal 131 for administrative organ or the terminal 141 for company. The server 101 may notify the abnormality of the driver 1 to the terminal 151 for transportation facilities when the terminal 111 for healthcare professionals does not respond after notifying the abnormality of the driver 1 or when the terminal 111 for healthcare professionals does not perform operations for requesting the support or rescue of the driver 1 to the terminal 131 for administrative organ or the terminal 151 for transportation facilities.

The criteria determination unit 31b determines whether the biometric information is not greater than or equal to the dangerous value (S509). The criteria determination unit 31b transmits an emergency signal to the vehicle control unit 51 when the heart rate is in the second range or when the electrocardiographic complex of the driver 1 measured by the handle part electrocardiograph 41a or the pacemaker 41c is classified as ventricular tachycardia or ventricular fibrillation, the vehicle control unit 51 blinks the hazard lamp of the vehicle 50, and the audio output unit 33b outputs a sound to the outside of the vehicle to alert the surroundings when the vehicle 50 stops urgently (S511). The process thereafter may be performed in the same manner as in the above-described embodiment.

In this way, since the safe driving assistance system 100 according to the embodiment of the present invention controls the operation status of the vehicle based on the determination result of the criteria determination unit, it is possible to support during the vehicle operation considering the health status of the driver. In particular, driving of the vehicle by a patient with arrhythmia can be supported.

<Safely Stop Assistance Method>

FIGS. 15 and 16 are referred. In one embodiment, when the criteria determination unit 31b determines that the heart rate measured in the pulse meter is out of the first range, the control unit 31 requests the vehicle control unit 51 to slow down the vehicle 50 and adjust the distance to the leading vehicle 60. The vehicle control unit 51 slows down the vehicle 50 according to a prescribed operating conditions in response to the requirement of the control unit 31 and adjusts the inter-vehicle distance from the leading vehicle 60 (S601). The process thereafter may be performed in the same manner as in the above-described embodiment.

FIG. 17 is referred. In one embodiment, when the criteria determination unit 31b determines that the heart rate measured by the pulse meter is in the second range, or when the electrocardiographic complex acquired by the handle part electrocardiograph 41a or the pacemaker 41c is classified as ventricular tachycardia or ventricular fibrillation, the control unit 31 requests the vehicle control unit 51 to slow down the vehicle 50 and adjust the distance between the leading vehicle 60. The vehicle control unit 51 slows down the vehicle 50 according to a prescribed operating conditions in response to the requirement of the control unit 31 and adjusts the inter-vehicle distance from the leading vehicle 60 (S701). The process thereafter may be performed in the same manner as in the above-described embodiment.

[Safe Driving Assistance System to Support Motor Vehicle Driving by Patients with Dementia]

Examples of the use of the safe driving assistance system of the present application as a safe driving assistance system for supporting the driving of a motor vehicle by patients with dementia will now be described. A detailed description of the configuration described in the above embodiment is omitted, and a characteristic configuration in the present embodiment will be specifically described.

In one embodiment, when the driver 1 is a patient with dementia, for example, a permissible information based on a correct answer rate of answers input from the driver 1 to questions presented to the driver 1 can be used. For example, when the correct answer rate does not satisfy a predetermined correct answer rate by asking questions to be used for cognitive function test by the Tokyo Metropolitan Police Department or the Hasegawa dementia scale or the like, the cognitive function of the driver 1 deteriorates, and the risks of accidents are increased. Therefore, the permissible information may be that the answer input from the driver 1 is equal to or higher than the predetermined correct answer rate.

When the cognitive function of the driver 1 deteriorates, the driver 1 may not recognize that he or she is driving the vehicle 50. The driver 1 may release his or her hand from the handle under such circumstances. Therefore, the permissible information may be that the driver 1 is holding the handle part. In one embodiment, the permissible information based on that the driver 1 is gripping the handle may be used from the pressure detected by a handle part pressure sensor 41*d* disposed on the handle. The method of evaluation of dementia, for example, the setting of questions and the rate of correct answers, may be changed, and it is preferable that the permissible information is periodically adjusted by the health care professional.

The safe driving assistance system according to the present invention is not limited to the safe driving support for personal drivers. With the aging of the population, the elderly are increasingly required to drive in the transportation facilities in recent years. For example, the aging of taxi drivers is also expected, and there is a possibility that the deterioration of cognitive function at the time of driving becomes a problem. The safe driving assistance system according to the present invention is a system capable of supporting safe driving in transportation facilities by an elderly driver. The rest of the configuration of the safe driving assistance system 100 may have the same configuration as that described in the above embodiment, and a detailed explanation thereof is omitted.

<Wearable Devices>

FIG. 4 is referred. The wearable device 10 includes, but is not limited to, a storage unit 11, a control unit 15, a communication unit 16, a power supply 17, and an input unit 18. The wearable device 10 may include the sensor 13. The storage unit 11 is, for example, a memory, and may include a permissible information storage unit which is a region for storing the permissible information of the driver 1 in one embodiment. The storage unit 11 may include a permissible information storage unit which is a region where the certification information of the driver 1 is stored. When the wearable device 10 is equipped with the sensor 13, the storage unit 11 may temporarily store the biometric information obtained from the driver 1 measured by the sensor 13.

In one embodiment, the sensor 13 may be a device for obtaining the biometric information from the driver 1, and include a sensor capable of monitoring the driver 1, for example, a pulse meter, a thermometer, a sphygmomanometer, a sensor measuring an oxygen saturation, or the like. The number, shapes, and arrangements of the sensor 13 included in the wearable device 10 can be arbitrarily selected and are not particularly limited. In the wearable device 10, the sensor 13 is an optional configuration, but the biometric information of the driver 1 can be obtained to monitor the condition of the driver 1 by providing the sensor 13 in the wearable device 10. When the driver 1 is a patient with dementia, it is also assumed that the driver 1 removes the wearable device 10. In such cases, since the sensor 13 stops acquiring the biometric information, the wearable device 10 may emit a warning sound or the like to alert the driver 1 and notify the respective terminals of the abnormalities via the server 101.

The wearable device 10 is not limited to the above configuration. For example, the wearable device 10 may further include a vibration function and an audio output unit. When the safe driving assistance in-vehicle device 30 determines that the driver 1 is not grasping the handle part based on the pressure detected by the handle part pressure sensor 41*d*, the wearable device 10 may alert or warn the driver 1 by the vibration function or audio output unit.

In FIG. 4A, the wearable device 10 is illustrated as a watch-type device, but the device is not limited thereto. The wearable device according to the present invention may be of any shape as long as the device is wearable by the driver 1. FIG. 6 is a schematic diagram illustrating the wearable device 10A according to a modification of the present embodiment. The wearable device 10A is a flat, preferably sheet-shaped device. Although the wearable device 10A having a rectangular sheet structure is shown in FIG. 6A, the wearable device 10A may be a disk-shaped structure. The wearable device 10A is affixed to the body of the driver 1 (e.g., the chest) via the adhesive layer 19. In the case where the driver 1 is a patient with dementia, the wearable device 10A may be attached to the back or the like in which it is difficult to remove by the driver 1. The rest of the configuration of the wearable device 10 may have the same configuration as that described in the above embodiment, and a detailed explanation thereof is omitted.

<Safe Driving Assistance in-Vehicle Device 300>

Figure 21:
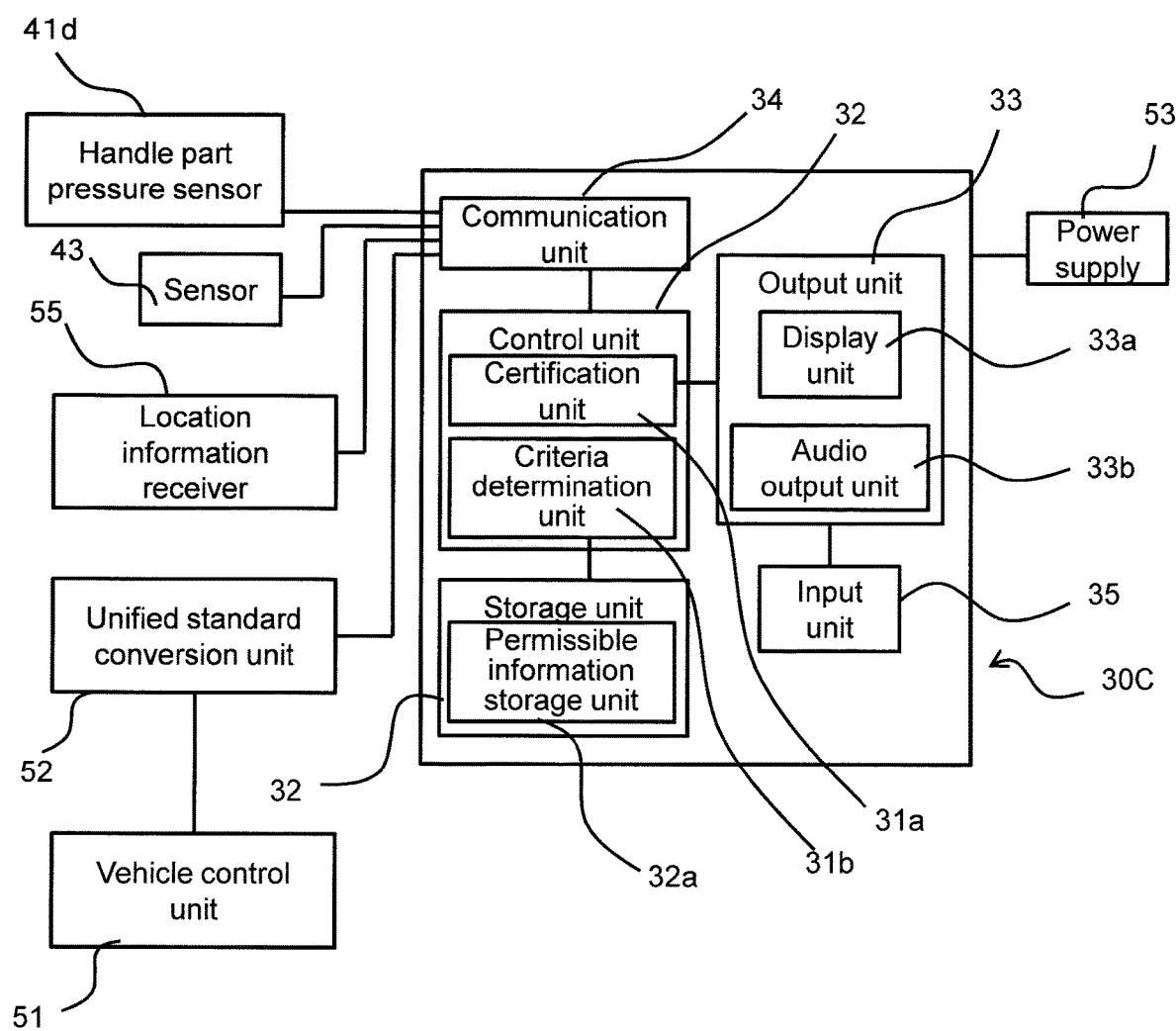
FIG. 21 is a block diagram illustrating a safe driving assistance in-vehicle device 30C according to an embodiment of the present invention.

FIG. 21 is a block diagram illustrating a safe driving assistance in-vehicle device 30C according to an embodiment of the present invention. The safe driving assistance in-vehicle device 30C includes, for example, a control unit 31 including a certification unit 31*a* and a criteria determination unit 31*b*, a storage unit 32 including a permissible information storage unit 32*a*, an output unit 33 including a display unit 33*a* and a audio output unit 33*b*, a communication unit 34, and an input unit 35. In one embodiment, the safe driving assistance in-vehicle device 30C connects the communication unit 34 to the handle part pressure sensor 41*d* and to the rest of the sensors 43.

In one embodiment, the criteria determination unit 31*b* is an application program or module for controlling a operating condition of the vehicle 50 by comparing the permissible information of the driver 1 stored in the server 101 or the wearable device 10 with at least the correct answer rate of the answer inputted from the driver 1 and/or the pressure detected from the handle part pressure sensor 41*d*.

In one embodiment, when the driver 1 is a patient with dementia, the criteria determination unit 31*b* can, for example, present questions to the driver 1, calculate a correct answer rate from answers inputted from the driver 1, and compare the permissible information of the driver 1 with the correct answer rate. For example, when the Hasegawa dementia scale is questioned, it is judged to be highly likely to be in a dementia status when the correct answer rate is below 20 points out of 30 points. For example, when the score is 24 or more, it may be judged as a state of non-dementia, when the score is 19 or less, it may be judged as a state of mild dementia, when the score is 15 or less, it may be judged as a state of moderate dementia, when the score is 10 or less, it may be judged as a state of rather severe dementia, and when the score is 4 or less, it may be judged as severe dementia. For this reason, when it is stored that the correct response rate is 24 points or more with respect to questions of the Hasegawa dementia scale as the permissible information stored in the permissible information storage unit 32*a*, the criteria determination unit 31*b* does not transmit a special signal or transmits a signal which allows driving to the vehicle control unit 51 if the correct response rate of the answers input from driver 1 is 24 points or more. On the other hand, when the correct answer rate of the answers inputted from the driver 1 is less than 24 points, the criteria determination unit 31b transmits a signal to the output unit 33 for displaying an alert and outputting a sound as described later. In one embodiment, when the correct answer rate of the answers input from the driver 1 does not satisfy a predetermined score, the questions may be presented to the driver 1 again, and the cognitive level of the driver 1 may be determined again by requesting the answers from the driver 1.

For example, when the driver 1 is determined that he or she is not holding the handle part, this indicates that symptoms of dementia have appeared, and it is very risky that the vehicle 50 is difficult to control. For this reason, when the permissible information stored in the permissible information storage unit 32a includes that the driver 1 is holding the handle part, the criteria determination unit 31b does not transmit a special signal or transmit a signal for permitting the driving to the vehicle control unit 51 if the criteria determination unit 31b detects that pressure is applied to the handle part by using the handle part pressure sensor 41d, that is, if the driver 1 is holding the handle part. On the other hand, when it is determined that the driver 1 is not gripping the handle from the pressure detected by the handle part pressure sensor 41d, the criteria determination unit 31b transmits a signal for stopping the vehicle 50 to the vehicle control unit 51 as will be described later.

In one embodiment, the display unit 33a displays the questions received from the criteria determination unit 31b, and the audio output unit 33b provides the questions received from the criteria determination unit 31b as sounds to the driver 1.

In one embodiment, the input unit 35 is a touch panel disposed on the display unit 33a. The driver 1 can input an answer to a question by touching the input unit 35. For example, a question and answer option may be displayed on the display unit 33a, and the answer selected by the driver 1 may be inputted from a location information in which the touch panel is pressed by touching the displayed answer option by the driver 1. The input unit 35 may be a microphone. For example, when the driver 1 answers verbally, the microphone may acquire the voice emitted by the driver 1, and the criteria determination unit 31b may recognize the answer of the driver 1 from the voice data.

The handle part pressure sensor 41d is disposed on the handle and is not particularly limited as long as it can be sensed that the driver 1 is gripping the handle. In one embodiment, the sensor 43 includes any sensor other than the handle part pressure sensor 41d. FIG. 9 is a schematic diagram of a handle part pressure sensor 41d and a sensor 43 according to an embodiment of the present invention. The handle part pressure sensor 41d and the sensor 43 include, for example, a sensor element 44, a control unit 45, a storage unit 46, a communication unit 47, and a power supply 48. The sensor element 44 is a device for detecting a biometric information, and a known sensor element can be used. The control unit 45 processes a signal detected by the sensor element 44. The storage unit 46 is arranged as required, and is a memory for temporarily storing the signal detected by the sensor element 44. The rest of the configuration included in the safe driving assistance in-vehicle device 30C may have the same configuration as that of the above-described embodiment, and a detailed explanation thereof will be omitted.

<A Certification Method of a Driver>

Figure 23:
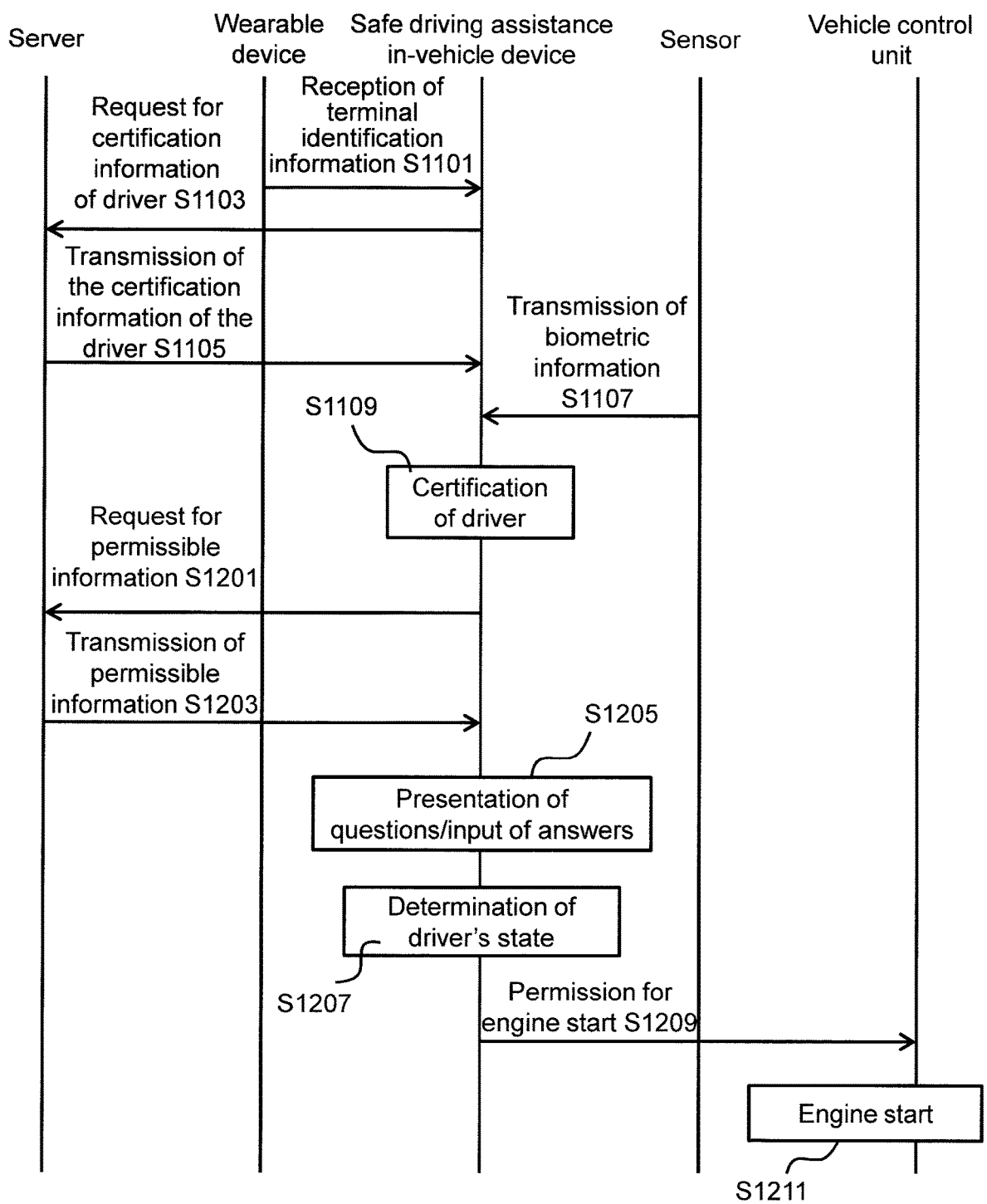
FIG. 23 is a flowchart illustrating a method of certification of the driver 1 using the safe driving assistance system 100 according to an embodiment of the present invention.

A certification method of the driver 1 using the safe driving assistance system 100 according to an embodiment of the present invention will be described. FIG. 23 is a flowchart illustrating a certification method of the driver 1 using the safe driving assistance system 100 according to an embodiment of the present invention. The safe driving assistance in-vehicle device 30 receives a terminal identification information of the wearable device 10 (S1101). The safe driving assistance in-vehicle device 30 requests the certification information to the server 101 (S1103). The server 101 transmits the stored certification information of the driver 1 to the safe driving assistance in-vehicle device 30 (S1105). In one embodiment, the certification information of the driver 1 includes a biometric information identifying the driver 1, such as weight, fingerprints, facial information, etc. of the driver 1, in addition to the name and ID of the driver 1. When the certification information of the driver 1 is stored in the wearable device 10, the safe driving assistance in-vehicle device 30 may request and receive the certification information of the driver 1 from the wearable device 10.

The safe driving assistance in-vehicle device 30 receive the biometric information of the driver 1, for example, from a sensor 43 arranged in the driver's seat (S1107). As the biometric information of the driver 1 acquired by the sensor 43, the weight, the fingerprint, and an image of the face of the driver 1 is exemplified but is not limited thereto. The safe driving assistance in-vehicle device 30 compares the weight, fingerprint information, or face information of the driver 1 included in the certification information with the weight, fingerprint, or face images of the driver 1 received from the sensor 43, and certificates the driver 1 when the weight, fingerprint, or face images match or roughly match (S1109).

The certification method of the driver 1 using the safe driving assistance system 100 according to the embodiment may be substantially the same as the certification method described in the above embodiment. In FIG. 12, the same certification methods as in the above embodiment can be used up to the process S303. The certification unit 31a receives the certification information of the driver 1 from the server 101 or the wearable device 10 (S305). The certification unit 31a may determine whether the sensor 13, the handle part pressure sensor 41d and the sensor 43 mounted on the vehicle 50 coincides with a sensor for monitoring the driver 1 included in the certification information of the driver 1. The certification unit 31a may transmit an error signal to the output unit 33 when the handle part pressure sensor 41d and the sensor 43 mounted on the vehicle 50 does not match the sensor included in the certification information of the driver 1. Since the certification methods described in the above embodiments can be used after the process S307, detailed descriptions thereof are omitted.

<A Determination Method of a State of a Driver>

The safe driving assistance in-vehicle device 30C requests a permissible information of the driver 1 to the server 101 (S1201). The server 101 transmits the stored permissible information to the safe driving assistance in-vehicle device 30C (S1203). The safe driving assistance in-vehicle device 30C presents questions to the driver 1 via the display unit 33a and/or the audio output unit 33b, answers from the driver 1 is inputted via the input unit 35 (S1205). The criteria determination unit 31b calculates a correct answer rate from the inputted answers and compares the permissible information of the driver 1 with the correct answer rate (S1207). The safe driving assistance in-vehicle device 30C allows the vehicle control unit 51 to start the vehicle 50 engine when the correct answer rate of the driver 1 is within the permissible ranges (S1209). Upon receiving a permissible signal from the safe driving assistance in-vehicle device 30, the vehicle control unit 51 can start the engine of the vehicle 50 (S1211).

Figure 24:
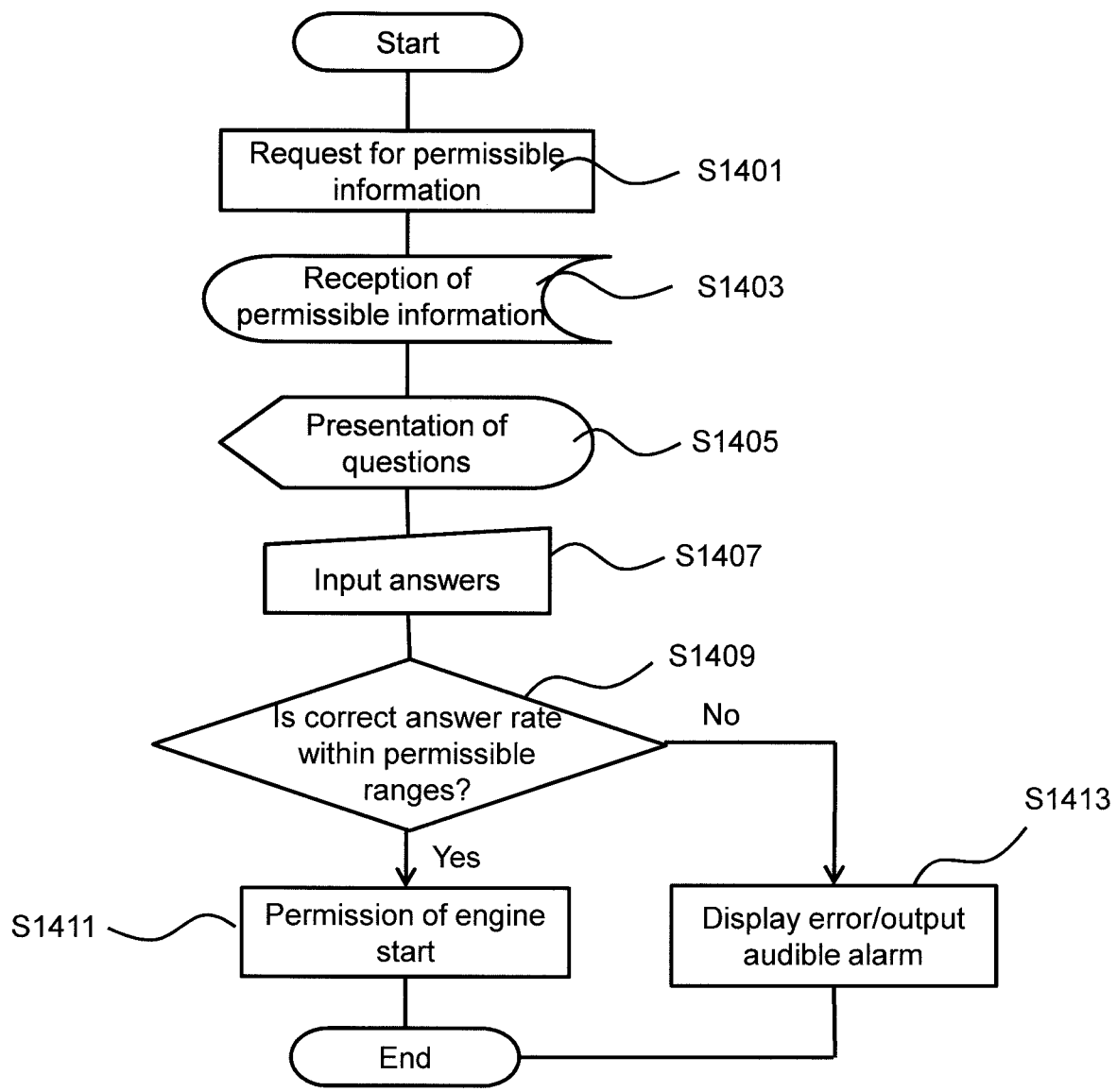
FIG. 24 is a flowchart illustrating a determination method of a state of the driver 1 in the safe driving assistance in-vehicle device 30 according to an embodiment of the present invention.

FIG. 24 is a flowchart illustrating a determination method of the state of the driver 1 in the safe driving assistance in-vehicle device 30. The criteria determination unit 31b of the safe driving assistance in-vehicle device 30C requests the permissible information of the driver 1 to the server 101 or the wearable device 10 (S1401). The safe driving assistance in-vehicle device 30C receives the permissible information from the server 101 or the wearable device 10. The permissible information of the driver 1 may be stored in the permissible information storage unit 32a (S1403). The criteria determination unit 31b presents the questions via the display unit 33a to the driver 1 and/or via the audio output unit 33b (S1405). The driver 1 inputs the answers to the questions through the input unit 35 (S1407). The criteria determination unit 31b calculates the correct answer rate from the answer input from the driver 1 via the input unit 35 and compares the permissible information of the driver 1 with the correct answer rate of the driver 1 (S1409). The criteria determination unit 31b allows the vehicle control unit 51 to start the engine of the vehicle 50 when these biometric information are within the permissible ranges.

In one embodiment, the criteria determination unit 31b transmits a signal to allow the engine to start to the vehicle control unit 51 when it is determined that the correct answer rate of the driver 1 is equal to or higher than a predetermined correct answer rate (S1411). On the other hand, when the correct answer rate of the driver 1 does not satisfy the predetermined correct answer rate, or when the driver 1 does not grip the handle part, the criteria determination unit 31b does not transmit a signal for permitting the vehicle control unit 51 to start the engine. In one embodiment, when the criteria determination unit 31b determines that the correct answer rate of the driver 1 does not satisfy the predetermined correct answer rate, or when the driver 1 does not grip the handle part, the criteria determination unit 31b transmits an error signal to the output unit 33, and the display unit 33a indicates a certification error. In one embodiment, the audio output unit 33b may output an audible alarm in response to an error signal (S1413).

<Safe Driving Assistance Method>

Figure 25:
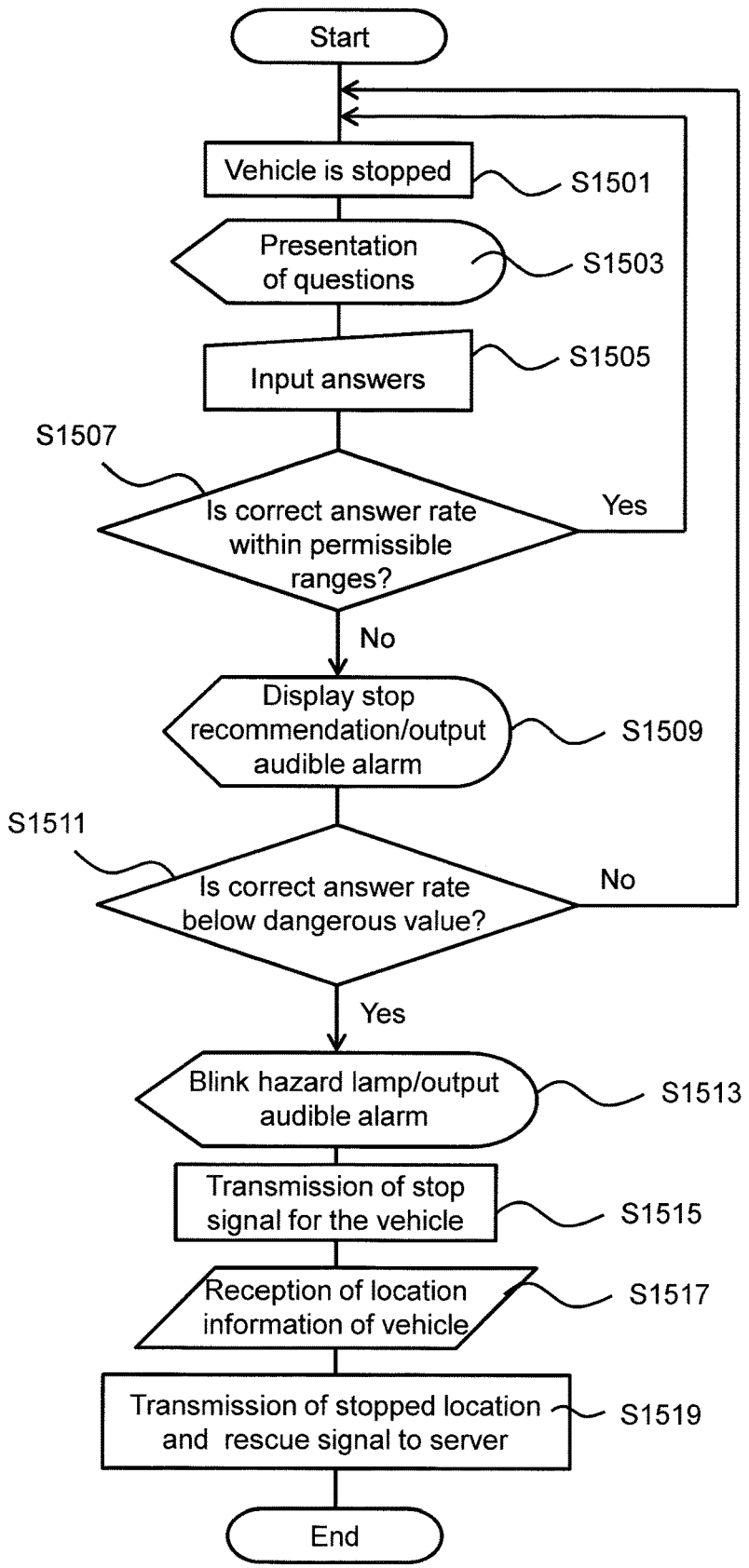
FIG. 25 is a flowchart illustrating a safe driving support method according to the safe driving assistance system 100 according to an embodiment of the present invention.

FIG. 25 is a flowchart illustrating a safe driving assistance process performed by the safe driving assistance system 100 according to an embodiment of the present invention. The driver 1 starts the operation of the vehicle 50, for example, when the vehicle 50 is stopped at a red light or the like, i.e., when the brake pedal is depressed (S1501), the criteria determination unit 31b presents questions to the driver 1 through the display unit 33a, and/or outputs the questions as a sound via the audio output unit 33b (S1503). The driver 1 inputs answers to the questions through the input unit 35 (S1505). The criteria determination unit 31b calculates a correct answer rate from the answers input from the driver 1 via the input unit 35, and compares the correct answer rate with the permissible information of the driver 1 stored in the permissible information storage unit 32a (S1507). When the criteria determination unit 31b determines that the correct answer rate of the driver 1 is equal to or higher than a predetermined correct answer rate, the criteria determination unit 31b does not control the vehicle control unit 51. That is, the driver 1 can normally operate the vehicle 50.

On the other hand, when it is determined that the correct answer rate of the driver 1 does not satisfy the predetermined correct answer rate, the criteria determination unit 31b transmits a signal for giving a stop recommendation to the output unit 33, and the display unit 33a displays the stop recommendation. In one embodiment, the audio output unit 33b may output an alert sound in response to a signal recommending a stop (S1509). In one embodiment, the safe driving assistance in-vehicle device 30 may transmit the abnormal information of the driver 1 to the server 101 via the communication unit 34.

The criteria determination unit 31b determines whether or not the biometric information is equal to or greater than the dangerous value, that is, whether or not the correct answer rate of the driver 1 is lower than a predetermined correct answer rate (S1511). The criteria determination unit 31b transmits an emergency signal to the vehicle control unit 51 when the correct answer rate of the driver 1 is lower than the predetermined correct answer rate or when the driver 1 does not grip the handle part, the vehicle control unit 51 blinks the hazard lamp of the vehicle 50, and the audio output unit 33b outputs a sound for calling attention to the surroundings to the outside of the vehicle when the vehicle 50 stops urgently (S1513).

The criteria determination unit 31b transmits a stop signal to the vehicle control unit 51 of the vehicle 50, and the vehicle control unit 51 stops the vehicle 50 (S1515). In one embodiment, the control unit 31 may receive a location information in which the vehicle 50 has stopped from the location information receiver 55 and send the location information in which the vehicle 50 has stopped to the server 101 via the communication unit 34 (S1517). The control unit 31 may transmit a rescue signal to the server 101 (S1519). The server 101 may notify the terminal 111 for healthcare professionals of the abnormality of the driver 1 and transmit the biometric information or the like of the driver 1. The server 101 may transmit the rescue signal of the driver 1 to the terminal 131 for administrative organ and transmit the biometric information or the like of the driver 1. In one embodiment, the server 101 may transmit the rescue signal of the driver 1 to the terminal 141 for company when the terminal 111 for healthcare professionals does not respond or the operation requesting rescue of the driver 1 is not performed to the terminal 131 for administrative organ or the terminal 141 for company after notifying the driver 1 of the abnormality. The server 101 may transmit the rescue signal of the driver 1 to the terminal 151 for transportation facilities when the terminal 111 for healthcare professionals does not respond or when the operation of requesting rescue of the driver 1 is not performed from the terminal 111 for healthcare professionals to the terminal 131 for administrative organ or the terminal 151 for transportation facilities after notifying the abnormality of the driver 1. Configurations other than these may have the same configuration as that of the above-described embodiment, and a detailed description thereof will be omitted.

<Safely Stop Assistance Method>

FIG. 15 is referred. In one embodiment, when the criteria determination unit 31b determines that the correct answer rate of the driver 1 does not satisfy the predetermined correct answer rate, the control unit 31 requests the vehicle control unit 51 to slow down the vehicle 50 and adjust the inter-vehicle distance from the leading vehicle 60. The vehicle control unit 51 slows down the vehicle 50 according to a prescribed operating conditions in response to the requirement of the control unit 31 and adjusts the inter-vehicle distance from the leading vehicle 60 (S601). The process S603 may be the same process as that of the above-described embodiment, and detailed descriptions thereof are omitted.

FIG. 17 is referred. In one embodiment, when the correct answer rate of the driver 1 falls below the predetermined correct answer rate of the driver 1, or when the driver 1 is not grasping the handle part, the control unit 31 requests the vehicle control unit 51 to slow down the vehicle 50 and adjust the inter-vehicle distance from the leading vehicle 60. The vehicle control unit 51 slows down the vehicle 50 according to the prescribed operating conditions in response to the requirement of the control unit 31 and adjusts the inter-vehicle distance from the leading vehicle 60 (S701). The process S703 may be the same process as that of the above-described embodiment, and detailed descriptions thereof are omitted.

[Safe Driving Assistance System to Support Motor Vehicle Driving Considering the Mental Condition of a Driver]

Examples of the use of the safe driving assistance system of the present invention as a safe driving assistance system for supporting the driving of a motor vehicle considering the mental condition of a driver will now be described. A detailed description of the configuration described in the above embodiment is omitted, and a characteristic configuration in the present embodiment will be specifically described.

In one embodiment, when the driver 1 has a sleep disorder, or is in a state easy to feel sleepy which is not up to sleep disorder, a permissible information based on, for example, skin temperature, pulse rate, brain wave pattern, or eye opening rate of the driver 1 may be used. For example, when the skin temperature is equal to or higher than a predetermined temperature, the pulse is less than a predetermined number, $\theta$ wave is included in the brain wave, or the eye opening ratio is less than a predetermined value, there is a high possibility that the driver 1 feels sleepy, and the risk of falling into the drowsy driving state is increased thereafter. Therefore, the permissible information may be that the skin temperature is less than the predetermined temperature, the pulse is the predetermined number or more, the $\theta$ wave is not detected in the brain wave, or the eye opening ratio is the predetermined value or more.

In one embodiment, when the driver 1 is a patient with schizophrenia or manic-depressive psychosis, a permissible information based on, for example, a skin temperature, a sweat volume, a pulse, a brain wave, or a rate of facial movement of the driver 1 can be used. In situations such as tailgating, the driver 1 is in an excited state and these criteria can be applied. For example, when the skin temperature is equal to or higher than a predetermined temperature, the sweat amount is increased, the pulse is equal to or higher than a predetermined number, continuous $\beta$ wave is included in the brain wave, or the ratio of the facial movement of the driver is equal to or higher than a predetermined value, there is a high possibility that the driver 1 has symptoms of schizophrenia and manic-depression psychosis, and the risk of the driver becoming in a state of being unable to drive thereafter increases. For this reason, the permissible information may be that the skin temperature is less than the predetermined temperature, the sweat amount is not significantly increased, the pulse is less than the predetermined number, the continuous $\beta$ wave is not detected in the brain wave, or the ratio of the facial movement of the driver is less than the predetermined value. In the present embodiment, the permissible information is determined in advance by the healthcare professional based on the diagnosis result of the driver 1 by the healthcare professional. Skin temperature, pulse rate, brain wave pattern, or eye opening rate, which is likely to feel sleepy, vary among individuals, and are affected by the patient's physical condition. Individual differences in the skin temperature, the sweating volume, the pulse, the brain wave, or the rate of the facial movement of patients with schizophrenia or manic-depressive psychosis or drivers in agitated states such as tailgating are also affected by the patient's physical condition. For this reason, the permissible information is preferably periodically adjusted by the health care professional. The rest of the configuration of the safe driving assistance system 100 may have the same configuration as that described in the above embodiment, and a detailed explanation thereof is omitted.

<Wearable Devices>

FIG. 4 is referred. The wearable device 10 includes, but is not limited to, a storage unit 11, a sensor (first sensor) 13, a control unit 15, a communication unit 16, a power supply 17, and an input unit 18.

In one embodiment, the sensor 13 is a device which acquires a biometric information from the driver 1, including, but not limited to, one or more sensors selected from the group consisting of, for example, a pulse meter 13a, a thermometer 13b, and a diaphoremeter 13c. In the present embodiment, the pulse rate measured by the pulse meter 13a is treated as substantially synonymous with the heart rate. In the present embodiment, it can be determined whether or not the driver 1 is ready to operate a vehicle 50 by comparing the skin temperature measured by thermometer 13b, the pulse rate measured by the pulse meter 13a, and the sweat rate measured by the diaphoremeter 13c with the permissible information of the driver 1 described later. The sensor 13 may further include other sensors capable of measuring the biometric information of the driver 1, e.g., sensors that measure blood pressure, oxygen saturation, and the like. The number, shapes, and arrangements of the sensors 13 included in the wearable device 10 can be arbitrarily selected and are not particularly limited. The wearable device 10 may be configured not to include the sensor 13 when the pulse meter equivalent to the sensor 13 is used as the sensor 43 disposed in other than the wearable device 10 described later. The rest of the configuration of the wearable device 10 may have the same configuration as that described in the above embodiment, and detailed descriptions thereof are omitted.

<Safe Driving Assistance in-Vehicle Device 30D>

Figure 22:
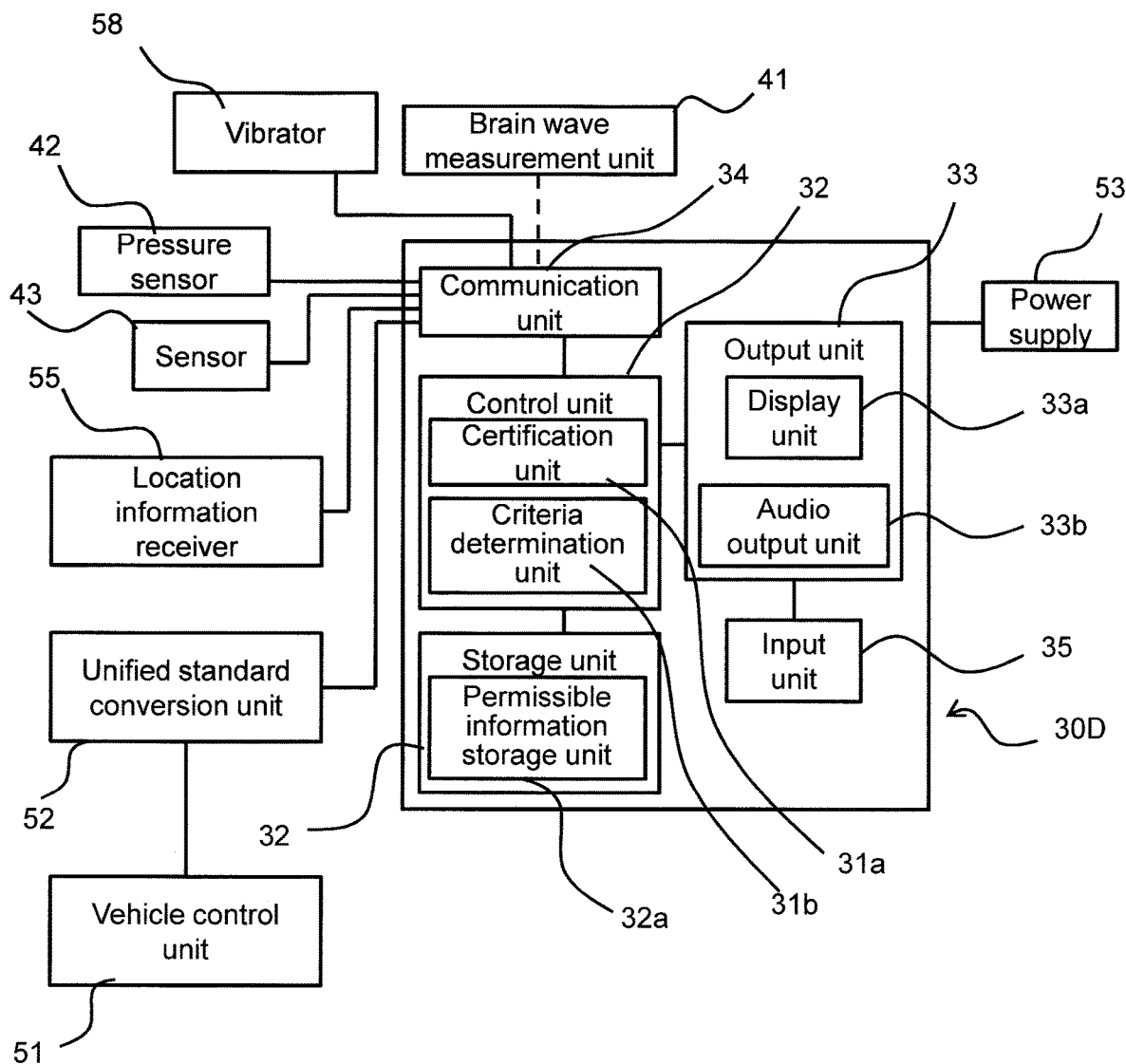
FIG. 22 is a block diagram illustrating a safe driving assistance in-vehicle device 30D according to an embodiment of the present invention.

In one embodiment, the safe driving assistance in-vehicle device 30D is mounted on the vehicle 50 and connects to the vehicle control unit 51 of the vehicle 50. FIG. 22 is a block diagram illustrating the safe driving assistance in-vehicle device 30 according to an embodiment of the present invention. The safe driving assistance in-vehicle device 30D includes, for example, a control unit 31 including a certification unit 31a and a criteria determination unit 31b, a storage unit 32 including a permissible information storage unit 32a, a output unit 33 including a display unit 33a and an audio output unit 33b, a communication unit 34, and an input unit 35. In one embodiment, the safe driving assistance in-vehicle device 30 includes a brain wave measurement unit 41A, a pressure sensor 42, and other sensors 43 (also referred to as the brain wave measurement unit 41A, the pressure sensor 42, and other sensors 43 are also referred to as second sensors), and is connected to these sensors via the communication unit 34. In one embodiment, the safe driving assistance in-vehicle device 30 connects to a location information receiver 55. In one embodiment, the safe driving assistance in-vehicle device 30 is preferably connected to the vehicle control unit 51 via the unified standard conversion unit 52. In one embodiment, the safe driving assistance in-vehicle device 30 connects to a vibrator 58 via the communication unit 34.

In one embodiment, the criteria determination unit 31b is an application program or module for comparing a permissible information of the driver 1 stored in the server 101 or the wearable device 10 with at least a biometric information measured from the sensor 13 and/or the brain wave measurement unit 41A of the wearable device 10 to control the operating status of the vehicle 50.

In one embodiment, when the driver 1 has a sleep disorder or is easy to feel sleepy that is not until a sleep disorder, the criteria determination unit 31b may compare the measured biometric information using, for example, the permissible information based on the skin temperature, pulse rate, brain wave patterns, or eye opening ratio of the driver 1. For example, when the skin temperature is equal to or higher than a predetermined temperature, the pulse is less than a predetermined number, the θ wave included is in the brain wave, or the eye opening ratio is less than a predetermined value, there is a high possibility that the driver 1 feels sleepy, and the risk of falling into the drowsy driving state is increased thereafter. Therefore, when the permissible information stored in the permissible information storage unit 32a is that the skin temperature is less than a predetermined temperature, the pulse is a predetermined number or more, the θ wave is not detected in the brain wave, or the eye opening ratio is a predetermined value or more, the criteria determination unit 31b does not transmit a special signal or transmits a signal for permitting the operation the vehicle to the vehicle control unit 51 if the skin temperature by the sensor 13 is less than the predetermined temperature, the pulse is the predetermined number or more, the θ wave is not detected in the brain wave, or the eye opening ratio is the predetermined value or more measured. On the other hand, when the skin temperature of the driver 1 measured by the sensor 13 is equal to or higher than the predetermined temperature, the pulse is less than the predetermined number, the θ wave included is in the brain wave, or the eye opening ratio is less than the predetermined value, the criteria determination unit 31b transmits a signal for displaying a warning and outputting a sound to the output unit 33, as described later.

The detection of the brain wave pattern of the driver 1 by the criteria determination unit 31b and the detection of the eye opening rate of the driver 1 can be realized by using a known pattern recognition technique. Further, the criteria determination unit 31b may detect the pattern of the brain wave of the driver 1 measured by the brain wave measurement unit 41A by combining the pattern recognition technology with the artificial intelligence technique. The criteria determination unit 31b may detect the closed eye condition of the driver 1 from the images of the face of the driver 1 measured by the face certification sensor included in the sensor 43. In this specification, the eye opening ratio is a ratio of an area of eyes detected in the image of the face of the driver 1 at the time of driving to the area of eyes detected in the image of the face of the driver 1 when the driver 1 is in the eye opening state, that is, the normal state or the state prior to driving.

For example, when the brain wave includes a δ wave, when the driver 1 is in the closed eyes state (not opened), or when the pressure sensor 42 does not detect the hand pressure of the driver 1, the driver is likely in the unconscious sleepy driving state. When the driver 1 releases both hands from the handle part while driving, the criteria determination unit 31b can judge that an abnormality has occurred to the driver 1 based on the change in pressure measured by the pressure gauge. Therefore, when the brain wave includes δ waves, the driver 1 is in the closed eyes state, or the pressure sensor 42 does not detect the hand pressure of the driver 1, as the permissible information stored in the permissible information storage unit 32a, the criteria determination unit 31b transmits a signal for stopping the vehicle 50 to the vehicle control unit 51, as described later.

In one embodiment, when the driver 1 is a patient with schizophrenia or manic-depressive psychosis, the criteria determination unit 31b may compare the measured biometric information with the permissible information based on, for example, the skin temperature, sweat amount, pulse rate, brain wave, or the rate of the facial movement of the driver 1. For example, when the skin temperature is equal to or higher than a predetermined temperature, the sweat rate is increased, the pulse is equal to or higher than a predetermined number, the continuous β wave is included in the brain wave, or the ratio of the facial movement of the driver is equal to or higher than a predetermined value, there is a high possibility that the driver 1 has symptoms of schizophrenia and manic-depressive psychosis, and the risk of the driver becoming in a state of being unable to drive thereafter increases. For this reason, when the permissible information stored in the permissible information storage unit 32a includes the information that the skin temperature is less than the predetermined temperature, the sweat rate does not increase significantly, the pulse is less than the predetermined number, the continuous β wave is not detected in the brain wave, or the ratio facial movement of the driver is less than the predetermined value, the criteria determination unit 31b does not transmit a special signal to the vehicle control unit 51 or transmits a signal which permits the driving, if the skin temperature of the driver 1 measured by the sensor 13 is less than the predetermined temperature, the sweat rate does not increase significantly, the pulse is less than the predetermined number, the continuous β wave is not detected in the brain wave, or the ratio of the facial movement of the driver is less than the predetermined value. On the other hand, when the skin temperature of the driver 1 measured by the sensor 13 is equal to or higher than the predetermined temperature, the sweat rate increases, the pulse rate is equal to or higher than the predetermined number, the continuous β wave is included in the brain wave, or the rate of the facial movement of the driver is equal to or higher than the predetermined value, the criteria determination unit 31b transmits a signal for displaying a warning and outputting a sound to the output unit 33, as will be described later.

In one embodiment, the communication unit 34 includes a communication unit conforming to a wireless communication standard such as, for example, but not limited to, Wi-Fi or Bluetooth (registered trademark) in order to perform wireless communication with the wearable device 10 or the brain wave measurement unit 41A.

In one embodiment, the sensors 43 include any sensors other than the pulse meter 13a, the thermometer 13b, the diaphoremeter 13c, the brain wave measurement unit 41A, and the pressure sensor 42. FIG. 9 is a block diagram of the brain wave measurement unit 41A and the sensor 43 according to an embodiment of the present invention. The brain wave measurement unit 41A, the pressure sensor 42, and the sensor 43 include, for example, a sensor element 44, a control unit 45, a storage unit 46, a communication unit 47, and a power supply 48.

In one embodiment, when an electrocardiogram is placed on the handle part as the sensor 43, the pulse rate measured by the sensor 43 may be used as the pulse rate for the biometric information of the driver 1, instead of the pulse meter 13a included in the wearable device 10.

In one embodiment, the vibrator 58 may be embedded in the backrest of the vehicle 50 on which the driver 1 sits. For example, when the criteria determination unit 31b detects either a δ wave contained in the brain wave measured by the brain wave measurement unit 41A, a closed eyes state of the driver 1, or a state in which the pressure sensor 42 does not detect the pressure of the hand of the driver 1, the control unit 31 of the safe driving assistance in-vehicle device 30 may drive the vibrator 58 to provide an vibration stimulus to the back of the driver 1. When the criteria determination unit 31b detects any abnormal value in which the skin temperature measured by thermometer 13b is equal to or higher than the predetermined temperature, the sweat rate measured by the diaphoremeter 13c is increased, the pulse rate measured by the pulse meter 13a is equal to or higher than the predetermined number, the continuous β wave is included in the brain wave measured by the brain wave measurement unit 41A, the rate of the facial movement of the driver 1 measured by the face recognition sensor is equal to or higher than the predetermined value, or the pressure of the hand of the driver 1 is not detected by the pressure sensor 42, the driver 1 can be awakened or the mental state of the driver 1 can be restored by providing such stimulus, and the safe driving of the driver 1 can be supported. The rest of the configuration of the safe driving assistance in-vehicle device 30D may have the same configuration as that described in the above embodiment, and a detailed explanation thereof will be omitted.

<A Certification Method of a Driver>

As for the certification method of the driver, a method schematically similar to the certification method described in the above-described embodiment can be used. FIG. 12 is referred. The same process as the process described in the above embodiment may be performed until the process S303, and a detailed explanation thereof is omitted. The certification unit 31a receives the certification information of the driver 1 from the server 101 or the wearable device 10 (S305). The certification unit 31a may determine whether the sensor 13, the brain wave measurement unit 41A and the sensor 43 mounted on the vehicle 50 coincide with a sensor for monitoring the driver 1 included in the certification information of the driver 1. When the sensor 13, the brain wave measurement unit 41A, the pressure sensor 42, and the sensor 43 mounted on the vehicle 50 do not match the sensor included in the certification information of the driver 1, the certification unit 31a may transmit an error signal to the output unit 33. Process after the process S307 may be performed in the same manner as the process described in the above embodiment, and detailed descriptions thereof are omitted.

<A Determination Method of a State of a Driver>

In one embodiment, the safe driving assistance in-vehicle device 30 may determine whether the driver 1 is ready to drive after certification the driver 1. The safe driving assistance in-vehicle device 30 requests the permissible information of the driver 1 to the server 101 (S201). The server 101 transmits the stored permissible information to the safe driving assistance in-vehicle device 30 (S203). The safe driving assistance in-vehicle device 30 receives a pulse rate from the pulse meter 13a, a skin temperature from the thermometer 13b, or a sweat rate from the diaphoremeter 13c, and receives a brain wave from the brain wave measurement unit 41A, a pressure at which the driver 1 grips the handle part from the pressure sensor 42 and an image of the face of the driver 1 from the sensor 43 (S205). The safe driving assistance in-vehicle device 30 compares the permissible information with the pulse rate, skin temperature, sweat amount, brain wave, the pressure to grip the handle part, and the percentage of opening and/or facial movements analyzed from the image of the face of the driver 1 (S207). The subsequent process of the process S209 may be the same processing as the process described in the above embodiment, and a detailed explanation thereof is omitted.

FIG. 13 is referred. The criteria determination unit 31b of the safe driving assistance in-vehicle device 30 requests the server 101 or the wearable device 10 for the permissible information of the driver 1 (S401). The safe driving assistance in-vehicle device 30 receives the permissible information from the server 101 or the wearable device 10. The permissible information of the driver 1 may be stored in the permissible information storage unit 32a (S403). The criteria determination unit 31b receives the pulse rate, skin temperature, or sweat rate of the driver 1 from the sensor 13, receives the brain wave from the brain wave measurement unit 41A, the pressure to grip the handle part from the pressure sensor 42, and receives the facial images from the sensor 43 (S405). The criteria determination unit 31b compares the permissible information with the pulse rate, skin temperature, or sweat rate of the driver 1 from the sensor 13, brain waves from the brain wave measurement unit 41A, pressures to grip the handle part from the pressure sensor 42, the eye opening rate and/or the rate of the facial movement analyzed from the facial images from the sensor 43 (S407). The criteria determination unit 31b allows the vehicle control unit 51 to start the engines of the vehicle 50 when these biometric information are within the permissible ranges.

In one embodiment, when the driver 1 has a sleep disorder, or when the driver 1 is easy to feel sleep which is not until the sleep disorder, the criteria determination unit 31b transmits a signal to the vehicle control unit 51 to allow the engine to start when it is determined that the skin temperature of the driver 1 measured by the sensor 13 is less than a predetermined temperature, the pulse rate is equal to or greater than a predetermined number, the θ wave is not detected in the brain wave, or the eye opening rate is equal to or greater than a predetermined value (S409). On the other hand, when the skin temperature of the driver 1 is greater than or equal to the predetermined temperature, the pulse rate is less than the predetermined number, the θ wave is included in the brain wave, or the eye opening ratio is less than the predetermined value, the criteria determination unit 31b does not transmit a signal for permitting the start of the engine to the vehicle control unit 51. In one embodiment, when the criteria determination unit 31b determines that the skin temperature of the driver 1 measured by the sensor 13 is greater than or equal to the predetermined temperature, the pulse rate is less than the predetermined number, the θ wave included in the brain wave, or the eye opening rate is less than the predetermined value, the criteria determination unit 31b transmits an error signal to the output unit 33, and the display unit 33a indicates a certification error. In one embodiment, the audio output unit 33b may output an audible alarm in response to an error signal (S411). In one embodiment, when the driver 1 is a patient with schizophrenia or manic-depressive psychosis, the criteria determination unit 31b transmits a signal to the vehicle control unit 51 to allow the engine to start when the skin temperature of the driver measured by the sensor 13 is less than a predetermined temperature, there is no significant increase in sweat rate, the pulse is less than a predetermined number, no continuous β wave is detected in the brain wave, or the rate of facial movement of the driver is less than a predetermined value. On the other hand, when the skin temperature is equal to or higher than the predetermined temperature, the sweat rate is increased, the pulse is equal to or higher than the predetermined number, the continuous β wave is included in the brain wave, or the rate of the face movement of the driver is equal to or higher than the predetermined value, the criteria determination unit 31b transmits an error signal to the output unit 33, and the display unit 33a displays a certification error.

<Safe Driving Assistance Method>

FIG. 14 is referred. When the driver 1 is driving the vehicle 50, the criteria determination unit 31b receives the pulse rate from the pulse meter 13a, the skin temperature from the thermometer 13b, or the sweat rate from the diaphoremeter 13c, and receives the brain wave from the brain wave measurement unit 41A, the pressure at which the driver 1 grips the handle part from the pressure sensor 42, and the facial image of the driver 1 from the sensor 43 (S501). The criteria determination unit 31b compares the permissible information of the driver 1 stored in the permissible information storage unit 32a with the pulse rate, the skin temperature, the sweat rate, the brain wave, the pressure to grip the handle part, the eye opening rate and/or the moving rate of the face analyzed from the facial images of the driver 1 (S503). The criteria determination unit 31b does not control the vehicle control unit 51 when these biometric information are within the permissible ranges. That is, the driver 1 can normally operate the vehicle 50.

On the other hand, when these biometric information are out of the range permitted by the permissible information, the criteria determination unit 31b transmits a signal for giving a stop recommendation to the output unit 33, and the display unit 33a displays the stop recommendation. In one embodiment, the audio output unit 33b may output an alert sound in response to a signal recommending a stop (S505). In one embodiment, the safe driving assistance in-vehicle device 30 may transmit the abnormal information of the driver 1 via the communication unit 34 to the server 101 (S507).

The criteria determination unit 31b determines whether the biometric information is not greater than or equal to the dangerous value (S509). That is, when detecting any abnormal value of δ waves included in the brain wave measured by the brain wave measurement unit 41A, the closed eye state of the driver 1, or a state in which the pressure sensor 42 does not detect the pressure of the hand of the driver 1, or when detecting any abnormal value of the skin temperature measured by the thermometer 13b being more than or equal to a predetermined temperature, the increased sweat rate measured by the sweat meter 13c, the pulse measured by the pulse meter 13a being more than or equal to the predetermined number, the continuous β waves included in the brain wave measured by the brain wave measurement unit 41A, the rate of the facial movement of the driver 1 measured by the face certification sensor being more than or equal to the predetermined number, or when not detecting the hand pressure of the driver 1, the criteria determination unit 31b transmits an emergency signal to the vehicle control unit 51, the vehicle control unit 51 transmits an emergency signal to the vehicle control unit 51, and the audio output unit 33b outputs the voice notify that the vehicle is urgently stopped to the outside of the vehicle (S511). Process after process S513 may be performed in the same manner as in the above-described embodiment, and detailed descriptions thereof are omitted.

In this manner, the safe driving assistance system 100 according to the embodiment of the present invention can support the driving of a vehicle that can cope with diseases such as schizophrenia, mania-depression psychosis, and sleep disorder, or psychiatric conditions of a driver such as sleepiness which do not extend to sleep disorder and dangerous driving.

<Safely Stop Assistance Method>

FIG. 15 is referred. In one embodiment, when the criteria determination unit 31b determines that the pulse rate, skin temperature, sweat rate, brain wave, and the rate of eye opening and/or the rate of facial movement analyzed from facial images of the driver's 1 are abnormal, the control unit 31 requests the vehicle control unit 51 to slow down the vehicle 50 and adjust the distance to a leading vehicle 60. The vehicle control unit 51 slows down the vehicle 50 according to a prescribed operating condition in response to the requirement of the control unit 31 and adjusts the inter-vehicle distance from the leading vehicle 60 (S601). Process after process S603 may be performed in the same manner as in the above-described embodiment, and detailed descriptions thereof are omitted.

FIG. 17 is referred. In one embodiment, when the criterion determination unit 31b detects a dangerous value of any of the δ wave included in the brain wave measured by the brain wave measurement unit 41A, the closed eyes state of the driver 1, or the state in which the pressure sensor 42 does not detect the hand pressure of the driver 1, or when the skin temperature measured by the thermometer 13b is equal to or higher than a predetermined temperature, the sweat rate measured by the sweat meter 13c is increased, the pulse measured by the pulse meter 13a is equal to or higher than a predetermined number, the continuous β wave is included in the brain wave measured by the brain wave measurement unit 41A, the rate of the facial movement of the driver 1 measured by the face certification sensor is equal to or higher than a predetermined value, or a state in which the pressure sensor 42 does not detect the hand pressure of the driver 1, the control unit 31 requests the vehicle control unit 51 to slow down the vehicle 50 and adjust the inter-vehicle distance from the leading vehicle 60. The vehicle control unit 51 slows down the vehicle 50 according to a prescribed operating condition in response to the requirement of the control unit 31 and adjusts the inter-vehicle distance from the leading vehicle 60 (S701). The process S703 may be the same process as that of the above-described embodiment, and detailed descriptions thereof are omitted.

In accordance with the methods of the present invention, a safe driving assistance system is provided that takes into account the health status of the driver and provides support when operating the vehicle. In one embodiment, a safe driving assistance system is provided for supporting driving of a vehicle by a hypoglycemic patient, an epilepsy patient, a heart disease patient, or a dementia patient, or driving of a vehicle in view of the psychiatric condition of the driver. In one embodiment, a safe driving assistance system is provided that identifies the driver to prevent unauthorized driving of the vehicle.

What is claimed is:

1. A safe driving assistance system, comprising:
   a wearable device including terminal identification information;
   a first sensor including at least one selected from a group consisting of a pulse meter, a thermometer, and a diaphoremeter;
   a second sensor including an interstitial fluid glucose concentration meter; and
   a safe driving assistance in-vehicle device including a criteria determination unit configured to compare permissible information for the driver against at least one of: first biometric information received from the first sensor and second biometric information received from the second sensor to determine whether a driver is in condition to drive a vehicle, wherein:
the permissible information comprises a minimum blood glucose level value and at least one of: a maximum heart rate value, a maximum skin temperature change value, and a maximum increase in sweat rate value,
the permissible information is preset based on a medical examination result of the driver,
the first biometric information and the second biometric information are acquired by the first and second sensors from the driver,
the permissible information is input from a terminal and configured to be rewritable only by a specialist,
the permissible information is stored in:
a server located outside the vehicle, the server being capable of communicating with the safe driving assistance in-vehicle device, or
a storage memory unit in the wearable device that is accessible only from the terminal,
the first biometric information includes one or more of: a heart rate, a skin temperature change, and a sweat rate change,
the second biometric information includes a blood glucose level,
the criteria determination unit is configured to determine whether:
the blood glucose level measured by the interstitial fluid glucose concentration meter is equal to or greater than the maximum blood glucose level value, and
at least one of: whether the heart rate measured by the pulse meter is less than the maximum heart rate value, whether the skin temperature change measured by the thermometer is less than the maximum skin temperature change value, and the increase in sweat rate measured by the diaphoremeter is less than the maximum increase in sweat rate value,
the safe driving assistance in-vehicle device is connected to a vehicle control unit of the vehicle driven by the driver, and
the safe driving assistance in-vehicle device is configured to cause the vehicle control unit to control the vehicle based on a determination made by the criteria determination unit with respect to whether the driver is in condition to drive the vehicle.

2. The safe driving assistance system according to claim 1, wherein the safe driving assistance in-vehicle device alerts the driver to sugar supplementation when the criteria determination unit determines that the blood glucose level measured by the interstitial fluid glucose concentration meter is less than the minimum blood glucose level, and at least one selected from the group consisting of: the heart rate measured by the pulse meter is the maximum heart rate value or higher, the skin temperature change measured by the thermometer is the maximum skin temperature change value or higher, and the increase in sweat rate measured by the diaphoremeter is the maximum increase in sweat rate value or higher.

3. The safe driving assistance system according to claim 2, further comprising:
a location information receiver capable of communicating with in-vehicle devices; and
the server located outside the vehicle and capable of communicating with the safe driving assistance in-vehicle device,
wherein the safe driving assistance in-vehicle device transmits an information of the driver, a location information of the vehicle received by the location information receiver, and a signal notifying the server of abnormality of the driver when the criteria determination unit determines that the blood glucose level measured by the interstitial fluid glucose concentration meter is less than the minimum blood glucose level value and at least one selected a group consisting of: that: the heart rate measured by the pulse meter is the maximum heart rate value or higher, the skin temperature change measured by the thermometer is the maximum skin temperature change value or higher, and the increase in sweat rate measured by the diaphoremeter is the maximum increase in sweat rate value or higher.

4. The safe driving assistance system according to claim 2, wherein:
the safe driving assistance in-vehicle device further includes an output unit having a display unit and an audio output unit,
the audio output unit outputs a voice notifying that the vehicle is urgently stopped to the outside of the vehicle, and
the vehicle control unit blinks at least one hazard lamp of the vehicle.

5. The safe driving assistance system according to claim 2, wherein:
the safe driving assistance in-vehicle device further includes an output unit having a display unit and an audio output unit,
the display unit configured to prompt the driver to supplement sugar or stop the vehicle, and
the audio output unit is configured to output a voice prompting the driver to supplement sugar or stop the vehicle to alert the driver to stop.

6. The safe driving assistance system according to claim 5, further comprising:
a location information receiver capable of communicating with in-vehicle devices, wherein:
the vehicle control unit slows down the vehicle and adjusts an inter-vehicle distance from the leading vehicle according to an operating conditions received from the safe driving assistance in-vehicle device when the criteria determination unit determines that the blood glucose level measured by the interstitial fluid glucose concentration meter is less than the minimum blood glucose level value and at least one selected from a group consisting of: the heart rate measured by the pulse meter is the maximum heart rate value or higher, the skin temperature change measured by the thermometer is the maximum skin temperature change value or higher, and the increase in sweat rate measured by the diaphoremeter is the maximum increase in sweat rate value or higher,
the location information receiver acquires a location information of the vehicle and searches for a location information at which the vehicle can stop,
the display unit indicates the location information at which the vehicle can stop when acquiring the location information at which the vehicle can stop, and
the audio output unit outputs a voice for guiding the vehicle to the driver.

7. The safe driving assistance system according to claim 1, wherein the safe driving assistance in-vehicle device alerts the driver to stop when the criteria determination unit determines that the blood glucose level measured by the interstitial fluid glucose concentration meter is less than the minimum blood glucose level value, and at least one selected from a group consisting of: the heart rate measured by the pulse meter is the maximum heart rate value or higher, the skin temperature change measured by the thermometer is the maximum skin temperature change value or higher, and the increase in sweat rate measured by the diaphoremeter is the maximum increase in sweat rate value or higher.

8. The safe driving assistance system according to claim 1, wherein:
   the permissible information includes a minimum blood glucose level value of 50 mg/dL, and
   the safe driving assistance in-vehicle device transmits a stop signal to the vehicle control unit to cause the vehicle to stop when the criteria determination unit determines that the blood glucose level measured by the interstitial fluid glucose concentration meter is less than 50 mg/dL.

9. The safe driving assistance system according to claim 8, further comprising:
   a location information receiver capable of communicating with in-vehicle devices; and
   the server located outside the vehicle and capable of communicating with the safe driving assistance in-vehicle device,
   wherein the safe driving assistance in-vehicle device transmits an information of the driver, the location information of the vehicle received by the location information receiver, and a rescue signal to the server when the criteria determination unit determines that a blood glucose level measured by the interstitial fluid glucose concentration meter is less than 50 mg/dL.

10. The safe driving assistance system according to claim 9, wherein:
    the vehicle control unit slows down the vehicle and adjusts an inter-vehicle distance from the leading vehicle according to an operating conditions received from the safe driving assistance in-vehicle device when the criteria determination unit determines that the blood glucose level measured by the interstitial fluid glucose concentration meter is less than 50 mg/dL,
    the location information receiver acquires a location information of the vehicle and searches for a location information at which the vehicle can stop, and
    the vehicle control unit stops the vehicle based on the position information at which the vehicle can be stopped when acquiring the location information at which the vehicle can stop.

11. The safe driving assistance system according to claim 1, further comprising:
    a third sensor capable of acquiring a third biometric information of the driver; and
    a certification unit included in the safe driving assistance in-vehicle device that is configured to certify the driver,
    wherein the certification unit carries out a first certification process to certify the driver based on the terminal identification information of the wearable device, and
    wherein a second certification process certifies the driver by comparing a second biometric information included in a certification information of the driver with the third biometric information received from the third sensor.

12. The safe driving assistance system according to claim 11, wherein:
    the safe driving assistance in-vehicle device transmits a signal permitting an engine to start to the vehicle control unit when the criteria determination unit determines that the blood glucose level measured by the interstitial fluid glucose concentration meter is more than the minimum blood glucose level value, and
    the vehicle control unit starts the engine in response to an engine starting operation by the driver.

13. The safe driving assistance system according to claim 11, wherein the safe driving assistance in-vehicle device does not transmit a signal permitting an engine to start to the vehicle control unit the criteria determination unit determines that the blood glucose level value measured by the interstitial fluid glucose concentration meter is less than the minimum blood glucose level value and at least one selected from a group consisting of: the heart rate measured by the pulse meter is the maximum heart value or higher, the skin temperature change measured by the thermometer is the maximum skin temperature change value or higher, and the increase in sweat rate measured by the diaphoremeter is the maximum skin temperature change value or higher.

* * * * *